United States Patent
Jimoh et al.

(10) Patent No.: US 10,112,189 B2
(45) Date of Patent: *Oct. 30, 2018

(54) TRANS-METALLATED MOF CATALYST

(71) Applicant: KING FAHD UNIVERSITY OF PETROLEUM AND MINERALS, Dhahran (SA)

(72) Inventors: Abiola Azeez Jimoh, Dhahran (SA); Abdul Malik Peedikakkal, Dhahran (SA)

(73) Assignee: King Fahd University of Petroleum and Minerals, Dhahran (SA)

( * ) Notice: Subject to any disclaimer, the term of this patent is extended or adjusted under 35 U.S.C. 154(b) by 0 days.

This patent is subject to a terminal disclaimer.

(21) Appl. No.: 15/966,784

(22) Filed: Apr. 30, 2018

(65) Prior Publication Data

US 2018/0280949 A1   Oct. 4, 2018

Related U.S. Application Data

(63) Continuation of application No. 15/458,437, filed on Mar. 14, 2017, now Pat. No. 9,975,114.

(60) Provisional application No. 62/335,954, filed on May 13, 2016.

(51) Int. Cl.
| | |
|---|---|
| *C07C 51/285* | (2006.01) |
| *B01J 31/12* | (2006.01) |
| *B01J 35/00* | (2006.01) |
| *B01J 35/10* | (2006.01) |
| *C07F 1/08* | (2006.01) |
| *C07F 3/06* | (2006.01) |
| *C07F 15/02* | (2006.01) |
| *C07C 27/16* | (2006.01) |
| *C07C 45/29* | (2006.01) |
| *C07C 29/48* | (2006.01) |
| *C07C 45/28* | (2006.01) |
| *C07C 47/54* | (2006.01) |

(52) U.S. Cl.
CPC ........... *B01J 31/123* (2013.01); *B01J 35/002* (2013.01); *B01J 35/1023* (2013.01); *B01J 35/1028* (2013.01); *B01J 35/1057* (2013.01); *B01J 35/1061* (2013.01); *C07C 27/16* (2013.01); *C07C 29/48* (2013.01); *C07C 45/28* (2013.01); *C07C 45/294* (2013.01); *C07C 47/54* (2013.01); *C07C 51/285* (2013.01); *C07F 1/08* (2013.01); *C07F 3/06* (2013.01); *C07F 15/025* (2013.01); *C07C 2601/14* (2017.05)

(58) Field of Classification Search
None
See application file for complete search history.

(56) References Cited

U.S. PATENT DOCUMENTS

| | | |
|---|---|---|
| 8,507,406 B2 | 8/2013 | Chen et al. |
| 2015/0173368 A1 | 6/2015 | Morris et al. |

FOREIGN PATENT DOCUMENTS

| | | |
|---|---|---|
| CN | 105312028 A | 2/2016 |
| WO | WO 2015/079229 A1 | 6/2015 |

OTHER PUBLICATIONS

Bhunia et al., Langmuir, 2013, 29, 8140-8145. (Year: 2013).*
Farhana Gul-E-Noor, et al., "Formation of Mixed Metal $Cu_{3-x}Zn_x(btc)_2$ Frameworks with Different Zinc Contents: Incorporation of $Zn^{2+}$ into the Metal-Organic Framework Structure as Studied by Solid-State NMR", The Journal of Physical Chemistry C, vol. 116, No. 39, 2012, pp. 20866-20873.
Bhunia, et al., Langmuir 2013, 29, 8140-8145.
Sun et al., Inorg. Chem. 2015, 54, 8639-8643.

* cited by examiner

*Primary Examiner* — Clinton A Brooks
*Assistant Examiner* — Kofi Adzamli
(74) *Attorney, Agent, or Firm* — Oblon, McClelland, Maier & Neustadt, L.L.P.

(57) ABSTRACT

A metal organic framework comprising zinc (II) ions and second metal ions, such as iron (II) ions, cobalt (II) ions, and copper (II) ions as nodes or clusters and coordinated 1,3,5-benzenetricarboxylic acid struts or linkers between them forming a porous coordination network in the form of polyhedral crystals that are isostructural to HKUST-1. Transmetallation processes for producing the metal organic frameworks, as well as methods for applications of the metal organic frameworks as catalysts, specifically catalysts for the oxidation of cyclic hydrocarbons, such as toluene, cyclohexane, and methylcyclohexane.

6 Claims, 34 Drawing Sheets

TRANS-METALLATED MOF CATALYST

CROSS-REFERENCE TO RELATED APPLICATIONS

This application is a Continuation of 15/458,437, pending, having a filing date of Mar. 14, 2017, which claims benefit of priority from U.S. Provisional Application No. 62/335,954 having a filing date of May 13, 2016, the entire contents of which are incorporated herein by reference.

BACKGROUND OF THE INVENTION

Technical Field

The present disclosure relates to metal organic frameworks comprising zinc (II) ions and second metal ions, such as iron (II) ions, cobalt (II) ions, and copper (II) ions as nodes or clusters and coordinated 1,3,5-benzenetricarboxylic acid struts or linkers between them. Additionally, the present disclosure relates to processes for producing the metal organic frameworks and their application as catalysts in methods for the oxidation of cyclic hydrocarbons, such as toluene, cyclohexane, and methylcyclohexane.

Description of the Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

Metal organic frameworks (MOFs) are crystalline, highly porous coordination polymers which are comprised of inorganic units (i.e. metals) coordinated to rigid organic fragments. They were built by a node linker approach that was first described by Robson [Hoskins, B. F.; Robson, R. *J. Am. Chem. Soc.* 1990, 112, 1546.—incorporated herein by reference in its entirety]. This method uses metal ions as nodes and organic ligands as linkers. In this case, a metal ion with a preferred coordination number and geometry combines with divergent ligand molecules to form an extended 1D, 2D or 3D network or networks. The metal linker interactions vary widely and have included ion-ion interactions, ion-dipole, dipole-dipole, hydrogen bonding, anion-$\pi$ interactions, $\pi$-$\pi$ interactions, as well as van-der Waals interactions [Burrows, A. D.; Chan, C. W.; Chowdhry, M. M.; McGrady, J. E.; Mingos, D. M. P. Chem. Soc. Rev. 1995, 329; and Classens, C. G.; Stoddart, J. F. *J. Phys. Org. Chem.* 1997, 10, 254.—each incorporated herein by reference in its entirety]. The strength of these interactions has been proven to directly influence the overall stability of the resulting framework [Braga, D. Chem. Comm. 2003, 2751-2754.—incorporated herein by reference in its entirety]. Extended networks can be developed from the basic principles guiding the formation of coordination complexes. FIG. 1 shows a representation of the formation of these coordination networks. Hence, the choice of metal center affects the resulting framework structure because a given metal has preference for a specific geometry and coordination environment.

A second approach to the synthesis of MOFs was described by Yaghi [Eddaoudi, M.; Li, H.; Reineke, T.; Fehr, M.; Kelley, D.; Groy, T. L.; Yaghi, O. M. *Topics in Catalysis* 1999, 9, 105.; and Eddaoudi, M.; Moler, D. B.; Li, H.; Chen, B.; Reineke, T. M.; O'Keeffe, M.; Yaghi, O. M. *Acc. Chem. Res.* 2001, 34, 319.—each incorporated herein by reference in its entirety]. This involves the use of multiple organic ligands and linkers and metal ions or clusters (secondary building units, SBUs) as nodes. FIG. 2 shows a schematic illustration of this MOF synthesis and structure. Most often, MOFs are easily synthesized by means of hydrothermal or solvothermal synthesis which involve high temperature self-assembly in a high boiling organic solvent or water in closed vessels [Yaghi, O. M.; O'Keeffe, M.; Ockwig, N. W.; Chae, H. K.; Eddaoudi, M.; Kim, J. M *Nature* 2003, 423, 705-714.; and Stock, N.; Biswas, S. *Chem. Rev.*, 2012, 112, 933-969.; and Yaghi, O. M.; Li, H. L. *J. Am. Chem. Soc.*, 1995, 117, 10401-10402.; and Lin, W. B.; Wang, Z. Y.; Ma, L. *J. Am. Chem. Soc.*, 1999, 121, 11249-11250.; and Chui, S. S. Y.; Lo, S. M. F.; Charmant, J. P. H.; Orpen, A. G.; Williams, I. D. *Science*, 1999, 283, 1148-1150.—each incorporated herein by reference in its entirety]. However, these methods typically require long reaction times, from several hours up to several days, depending upon the nature of the ligand, the reaction solvent, reagent concentrations and reaction temperature. They can also be produced using the microwave assisted process which allows the large scale synthesis of MOFs in a few minutes [Feldblyum, J.; Liu, M.; Gidley, D.; Matzger, A. J. Am. Chem. Soc. 2011, 133, 18257-18263.; and Dybtsev, D. N.; Nuzhdin, A. L.; Chun, H.; Bryliakov, K. P.; Talsi, E. P.; Fedin, V. P.; Kim, K. *Angew. Chem., Int. Ed.*, 2006, 45, 916-920.; and Ni, Z.; Masel, R. I.; *J. Am. Chem. Soc.*, 2006, 128, 12394-12395.—each incorporated herein by reference in its entirety].

MOF-5 is one of the first series of MOFs to be reported and fully characterized. It consists of an octahedral secondary building unit (SBU) which is made from $Zn_4O\ (CO_2)_6$ as an inorganic unit which is comprised of four $ZnO_4$ tetrahedra with a common vertex and six carboxylate groups. These octahedral SBUs are joined together by benzene linkers [Chalati, T.; Horcajada, P.; Gref, R.; Couvreur, P.; Serre, C. *J. Mater. Chem.*, 2011, 21, 2220-2227.—incorporated herein by reference in its entirety]. These unique units lead to a perfect cubic network whose vertices comprise the SBUs and the edges of which are made up of the benzene linkers. FIG. 3A shows the structure of MOF-5 in an extended 3D cubic framework. This compound was synthesized from Zn(II) and 1,4-benzenedicarboxylic acid (BDC) under organic conditions predetermined to form the SBU in situ. FIG. 3B shows the topology of the MOF structure as a ball-and-stick model. FIG. 3C shows the structure represented by $(OZn_4)O_{12}$ clusters (tetrahedrons) joined by BDC ions (connectors). Since the benzene links and the SBUs appear to be relatively rigid and large entities, the resulting structure has exceptionally high porosity (as indicated by its sorption) and stability [Yaghi, O. M., Sun, Z., Richardson, D. A. & Groy, T. L *J. Am. Chem. Soc.* 1994, 116, 802-808.—incorporated herein by reference in its entirety].

MOFs have been found to possess unique properties like high surface areas (up to 10400 $m^2/g$) and tunable pores that can be used in various potential applications such as gas storage, catalysis, separation, and drug delivery [Li, H., Eddaoudi, M., O'Keeffe, M. & Yaghi, O. M Nature 1999, 402, 276-279.; and Silva, P.; Valente, A. A.; Rocha, J.; Paz, F. A. A. *Cryst. Growth Des.*, 2010, 10, 2025-2028.; and Wang, Z.; Chen, G.; Ding, K. *Chem. Rev.*, 2009, 109, 322.; and Corma, A.; Garci'a, H.; Xamena, F. X. *Chem. Rev.*, 2010, 23, 1126.; and Li, J. R.; Kuppler, R. J.; Zhou, H. C. *Chem. Soc. Rev.*, 2009, 38, 1477.—each incorporated herein by reference in its entirety]. They have also been found to be candidates for other applications like microelectronics, sensing, optics, micromotors, molecular rotors, and bioreactors [Horcajada, P.; Chalati, T.; Serre, C.; Gillet, B.; Sebrie, C.; Baati, T.; Eubank, J. F.; Heurtaux, D.; Clayette, P.; Kreuz, C.; Chang, J. S.; Hwang, Y. K.; Marsaud, V.; Bories, P. N.; Cynober, L.; Gil, S.; Fe'rey, G.; Couvreur, P.; Gref, R. *Nat. Mater.,* 2010, 9, 172-178.; and Talin, A. A.; Centrone, A.; Ford, A. C.; Foster, M. E.; Stavila, V.; Haney, P.; Kinney, R. A.; Szalai, V.; Gabaly, F. E.; Yoon, H. P.; Le'onard, F.; Allendorf, M. D. *Science,* 2014, 343, 66.; and Kreno, L. E.; Leong, K.; Farha, O. K.; Allendorf, M.; Van Duyne, R. P.; Hupp, T. *Chem. Rev.,* 2012, 112, 1105.; and Cui, Y.; Yue, Y.; Qian, G.; Chen, B. *Chem. Rev.,* 2012,112, 1126.; and Ikezoe, Y.; Washino, G.; Uemura, T.; Kitagawa, S.; Matsui, H. *Nat. Mater.,* 2012, 11, 1081.; and Comotti, A.; Bracco, S.; Ben, T.; Qiu S.; Sozzani, P. *Angew. Chem., Int. Ed.,* 2014, 53, 6655.—each incorporated herein by reference in its entirety]. Presently, the most highly recognized applications of MOFs, however, have been in the areas of gas storage and separation. The strong interest in this research area stems from the urgent need to develop viable technologies for hydrogen fuel storage for commercial use as well as to control the concentration of $CO_2$ in the atmosphere.

High surface area and the possibility of varied structural modification amongst other desirable physical and chemical properties make it possible for MOFs to efficiently catalyze a broad range of reactions. The MOFs are usually modified by a method that is broadly known as post-synthetic-modification (PSM). PSM makes it possible to incorporate a highly diverse range of different functional groups making it largely free of the restrictions resulting from the synthetic conditions of the MOFs. PSM also allows the introduction of multiple metal ions into a single framework in a combinatorial manner, enabling an effective way to systematically fine tune and optimize MOF properties [Doherty, C. M.; Grenci, G.; Riccoo', R.; Mardel, J. I.; Reboul, J.; Furukawa, S.; Kitagawa, S.; Hill, A. J.; Falcaro, P. *Adv. Mater.,* 2013, 25, 4701.—incorporated herein by reference in its entirety]. The process in which new metal sites are incorporated into a MOF framework is known as transmetallation or post-synthetic metal exchange and the MOFs produced by this method can be described as isostructural MOFs with similar structural frameworks but different metal ions. FIG. 4 illustrates a general scheme for the post-synthetic modification of MOFs. This synthetic method can be used to obtain certain MOFs that cannot be obtained via conventional synthetic methods. Cation exchange also helps to enhance the properties of some MOFs by making it possible to incorporate a more useful metal site thereby improving some of their physical and chemical properties hence giving them more interesting applications. For example, HKUST-1 has a surface area of about 1500 $m^2/g$ and it contains $Cu^{2+}$ but the isostructure can be made by substituting the $Cu^{2+}$ with other metals. A unique property of transmetallation lies in the fact that new MOFs can be obtained by complete or partial substitution of metal ions within the framework without altering the morphology of the MOFs. FIG. 5 shows a schematic representation for post synthetic metal exchange or transmetallation. This process serves as an alternative, typically milder route for accessing new MOFs when conventional synthesis at high temperature fails [Wang, Z.; Cohen, S *Chem. Soc. Rev.,* 2009, 38, 1315-1329.—incorporated herein by reference in its entirety]. This substitution occurs at the metal nodes, often called the inorganic clusters or secondary building units (SBUs). Although the metal ions are integral parts of the MOFs' structures, they can be replaced either completely or partially within hours or days without necessarily affecting the MOFs' structures [Dinca, M.; Long, J. R. *J. Am. Chem. Soc.,* 2007, 129, 11172-11176.—incorporated herein by reference in its entirety]. Transmetallation changes the properties of the MOFs and also makes them useful for other important applications especially in catalysis. The transmetallated MOFs have multiple properties having separate metal sites that can be utilized for specific catalytic conversions of organic molecules.

The development of efficient new catalysts is still a serious challenge in chemical research. Hence the increasing demand for safer and energy saving reaction routes promotes the need to develop new materials towards the global aim of combating serious environmental challenges that stem from several industrial processes. Hence, catalyst development is an ever growing area of research. Recently, chemists have endorsed MOFs as viable heterogeneous catalysts to channel the course of new and existing chemical reactions to reduce industrial wastes and enable greener chemical processes. This work facilitates better understanding of physical and chemical processes such as surface interactions and facilitates novel concepts and ideas for the next generation of catalysts. The role of heterogeneous catalysts either in chemical or petrochemical industries cannot be overemphasized. They reduce the enormous wastes that are associated with homogeneous catalysts and also reduce cost due to their reusability. These heterogeneous catalysts occur in a different phase from the substrates and predominantly work base on an adsorption mechanism. The heterogeneous catalysts are mostly solids on which liquid or gaseous reaction mixtures are adsorbed. The active site may be either a planar exposed metal surface, a crystal edge with imperfect metal valence or a complicated combination of the two. Thus, not only most of the volume, but also most of the surface of a heterogeneous catalyst may be catalytically inactive. The dependence of catalytic activity on surface area and pore volume makes MOF catalysts a viable area of chemical research. Investigating the nature of the active sites requires technically challenging research. Thus, studies relating to new metal and ligand combinations for catalysis continue.

These highly porous, crystalline MOFs have some of the catalytically important properties of zeolites like uniform cavity and pore sizes as well as medium to large internal surface areas [Wang, L, J.; Deng, H.; Furukawa, H.; Gandara, 'F.; Cordova, K. E.; Peri, D.; Yaghi, O. M. *Inorg. Chem.* 2014, 53, 5881-5883.—incorporated herein by reference in its entirety]. Unlike zeolites, vast chemical varieties of MOFs can be synthesized due to the presence of infinite organic linkers. This suggests that the catalytic niche of MOFs is likely to be high value added reactions such as production of specific enantiomers, sensitive molecules, as well as production of fine chemicals, which require specific and tunable catalytic sites [Furukawa, H.; Ko, N.; Go, Y. B.; Aratani, N.; Choi, S. B.; Choi, E.; Yazaydin, A.; Snurr, R. Q.; O'Keeffe, M.; Kim, J.; Yaghi, O. M. *Science,* 2010, 329, 424.; and Pan, L.; Adams, K. M.; Hernandez, H. E.; Wang, X.; Zheng, C.; Hattori, Y.; Kaneko, K. *J Am. Chem. Soc.* 2003,125, 3062.—each incorporated herein by reference in its entirety]. Despite the various interesting and compelling recent developments in MOF catalysis, the area of MOF catalysis is still in an immature phase. Many researchers have likened MOF catalysis to enzyme catalysis, aiming towards the development of catalytic chemistry in the direction of an "artificial enzyme". Overall, the uniqueness of MOFs over other materials is yet to be fully illustrated since they have been reported to be of use as catalysts in the chemical or petrochemical industries.

Oxidation reactions are among the most important chemical conversions in industries and laboratories. Conversion of abundant and cheap hydrocarbons like toluene, cycloalkanes and methylcyclohexane into more valuable chemicals like aldehydes, ketones and acids stands as a significant process for consideration [Hayashi, H.; Cote, A. P.; Furukawa, H.; O'Keeffe, M.; Yaghi, O. M. *Nat. Mater.* 2007, 6,501.—incorporated herein by reference in its entirety]. Among these useful transformations, the direct oxidation of toluene to produce benzaldehyde is an attractive process. Toluene oxidation gives a mixture of oxygenated products like benzoic acid, benzyl alcohol, benzaldehyde and cresols. Commercially, benzaldehyde is mainly produced by the chlorination of toluene followed by the hydrolysis process, which generates large amounts of toxic acidic/basic discard solutions, leading to equipment corrosion and environmental pollution. Furthermore, the benzaldehyde produced by this route is not qualified to synthesize some high quality compounds such as perfumes or pharmaceuticals because the product contains chlorine [Friedrich Brühne and Elaine Wright "Benzaldehyde" in Ullmann's Encyclopedia of Industrial Chemistry, 2002, Wiley-VCH, Weinheim.—incorporated herein by reference in its entirety]. Therefore, there is a clear need to develop new materials to improve the selective oxidation of toluene as an alternative route to produce benzaldehyde and consequently benzoic acids.

Alkanes are naturally abundant and cheap carbon containing raw material which serve as attractive substrates for the production of value added organic chemicals (alcohols, ketones, aldehydes and carboxylic acids) [B. Retcher, J. S. Costa, J. Tang, R. Hage, P. Gamez, J. Reedijk, *J. Mol. Catal. A.* 2008, 286, 1-5.—incorporated herein by reference in its entirety]. Unfortunately, the chemical inertness of these compounds is a considerable limitation towards their vast application for direct syntheses of oxygenated products under relatively mild conditions. However, a proper metal catalyst and an appropriate oxidizing agent, as well as properly controlled reaction conditions, can lead to the development of a cleaner and more efficient chemical industry. Today, over a billion tons of cyclohexanone and cyclohexanol are produced every year and they are mostly used for the synthesis of Nylon-66 and Nylon-6 [M. Musser "Cyclohexanol and Cyclohexanone" in Ullmann's Encyclopedia of Industrial Chemistry, Wiley-VCH, Weinheim, 2005.—incorporated herein by reference in its entirety].

The structure of HKUST-1 and Zn-HKUST-1 metal organic frameworks has been investigated. Chui and coworkers were the first to synthesize HKUST-1 at the Hong Kong University of Science and Technology. HKUST-1 was discovered to be a highly porous metal coordination polymer $[Cu_3(BTC)_2(H_2O)_3]_n$ (where BTC is benzene-1,3,5-tricarboxylate) which has interconnected $[Cu_2(O_2CR)_4]$ units (where R is an aromatic ring), $C_{18}H_{12}O_{15}Cu_3$. It creates a 3-dimensional system of channels with a pore size of approximately 1 nm and an accessible porosity of about 40% in the solid. The single crystal structural analysis of HKUST-1 revealed that the polymer framework is composed of dimeric cupric tetracarboxylate building units, with a Cu-Cu inter-nuclear separation of 2.628(2) Å. FIG. 6 shows the crystal structure of the dicopper (II) tetracarboxylate building block containing two axial aqua ligands. The framework was found to be neutral because the twelve carboxylate oxygens from the two BTC ligands bind to four coordination sites for each of the three $Cu^{2+}$ ions of the formula unit. Hence each Cu atom completes is pseudo-octahedral coordination sphere with the presence of axial aqua ligands opposite to the Cu—Cu dimer. The tetracarboxylate unit provides a structural motif with potential four-fold symmetry, and the trimesic acid provides a three-fold symmetry element. FIG. 7 shows a HKUST-1 secondary building unit (SBU) demonstrating the tbo net topology and the paddlewheel structure. The origin of the nanochannels can be clearly considered to arise from the formation of larger octahedral secondary building units (SBUs). The main SBU in HKUST-1 is the octahedral unit with $Cu_2$ at its 6 vertices and 4 trimesate ions tetrahedrally disposed as "panels" for four of the eight triangular faces of the octahedron. FIG. 8 shows the $[Cu_3(TMA)_2(H_2O)_3]$ unit viewed along the cell body diagonal, demonstrating a hexagonal-n shaped window at the intersection of the nanopores. FIG. 9 shows the polymer framework and nanochannels with four-fold symmetry.

The Zn-HKUST-1 that contains $Zn^{2+}$ions is analogous to HKUST-1. Analysis of Zn-HKUST-1 by powder X-ray diffraction and gas sorption shows the retention of crystalline structure but negative nitrogen uptake at 77 K due to a dense surface layer that prevents the passage of small molecular species into the crystal framework [Bhunia, M. K, Hughes, J. T. Fettinger, J. C. and Navrotsky, A. *Langmuir* 2013, 29, 8140-8145.—incorporated herein by reference in its entirety]. The prevalence of zinc paddlewheels in a variety of MOFs, such as the previously discussed HKUST-1 suggests that Zn I a promising metal with which an isostructural analog to Cu-HKUST-1 can be constructed.

The application of metal organic frameworks has been investigated. Over the past decades, transition metal complexes comprising mainly phosphine ligands, salen or salophen ligands, pincer ligands and N-heterocyclic carbenes (NHCs) have had a remarkable impact on catalysis. Examples include the Nobel prize winning Noyori asymmetric hydrogenation, Sharpless oxidations (Sharpless epoxidation, Sharpless asymmetric dihydroxylation, and Sharpless oxyamination) as well as Jacobsen epoxidation [Noyori, R *Adv. Synth. Catal* 2003, 345, 12, 15-41.; and Katsuki, T.; Sharpless, K. B *J. Am. Chem. Soc.,* 1980, 102, 5974-5976.; and Jacobsen, E. N.; Marko, I.; Mungall, W. S.; Schroeder, G.; Sharpless, K. B. *J. Am. Chem. Soc.,* 1988, 110 1968-1970.; and Sharpless, K. B; Patrick, D. W.; Truesdale, L. K.; Biller, S. A. *J. Am. Chem. Soc.,* 1975, 97, 2305 2307.; and Zhang, W.; Loebach, J. L.; Wilson, S. R.; Jacobsen, E. N. *J. Am. Chem. Soc.,* 1990, 112, 7, 2801-2803.—each incorporated herein by reference in its entirety]. Most of these metal complexes have only been successful as homogeneous catalysts which have significant disadvantages like the difficulty of product separation, poor reusability and toxicity. Relatively insoluble and stable materials like zeolites, metals and metal oxides are widely used as heterogeneous catalyst on the industrial scale. Notable conversions like the Harber-Bosch, Contact process, Ostwald process, steam reforming, petrochemical reactions Ziegler Natta polymerization make use of these insoluble materials. In terms of easy post reaction separation, these materials have largely been successful. However, there is still an urgent need for the development of new materials that will be more energy efficient, more tunable, and more environmentally friendly.

MOFs have shown great catalytic prospects for a wide range of reactions due to the diversity in their structures, low toxicity, reusability and cost effectiveness. In fact MOFs are among the best candidates in bridging the gap between homogeneous and heterogeneous catalysis. The metals in the MOF structure often act as Lewis acids especially when the frameworks are activated by removing the coordinated labile solvent molecules or counter ions [Han, J. W.; Hill, C. L.; *J. Am. Chem. Soc.,* 2007, 129, 15094.—incorporated herein by reference in its entirety]. Fujita, et al. first reported the catalytic activity of a 2D Cd(II) based MOF for the cyanosilylation of aldehydes. Thy obtained the unsaturated metal cluster by removing two water molecules from the octahedral structure of [Cd(4,4'-bpy)$_2$(H$_2$O)$_2$].(NO$_3$)$_2$.4H$_2$O [Fujita, M.; Kwon, Y. J.; Washizu, S.; Ogura, K. *J. Am. Chem. Soc.* 1994, 116, 1151-1152.—incorporated herein by reference in its entirety]. Fe(BTC) has also been used as a heterogeneous catalyst for the selective methylation of primary aromatic amines using dimethyl carbonate, efficient oxidation of benzylic compounds using t-butyl-hydroperoxide as oxidizing agent, and oxidation of thiols to disulfides [Dhakshinamoorthy, A.; Alvaro, M.; Garcia, H. *Appl. Catal. A: General* 2010, 378, 19-25.; and Dhakshinamoorthy, A.; Alvaro, M.; Garcia, H. *J. Catal.* 2009, 267, 1-4.; and Dhakshinamoorthy, A.; Alvaro, M.; Garcia, H. *Chem. Commun.,* 2010, 46, 6476-6478.—each incorporated herein by reference in its entirety]. Seo, et al. first reported asymmetric catalysis using a homochiral MOF, [Zn(μ$_3$-O)(1-H)$_6$.2H$_3$O.12H$_2$O] for trans-esterification reactions. It was also the first MOF demonstrating that the organic linker embedded into a pore can catalyze an asymmetric reaction [Seo, J. S.; Whang, D.; Lee, H.; Jun, S. I.; Oh, J.; Jeon, Y. J.; Kim, K. *Nature,* 2000, 404, 982-986.—incorporated herein by reference in its entirety]. Lin, et al. also reported the activity of a homochiral non-interpenetrating MOF which was constructed in finite 1-dimensional [Cd(μ-Cl)$_2$]$_n$ zigzag chains with axial bipyridine bridging ligands containing orthogonal secondary functional groups [Wu , C.; Hu, A.; Zhang, L.; Lin, W. *J. Am. Chem. Soc.,* 2005, 127, 8940-8941.—incorporated herein by reference in its entirety]. The chiral secondary functional groups were used to generate a heterogeneous asymmetric catalyst for the addition of diethyl zinc to aromatic aldehydes to afford chiral secondary alcohols at up to 93% enantiomeric excess (ee).

More specifically, the catalytic activity of HKUST-1 has been investigated. HKUST-1 has been particularly well recognized for its high catalytic activity especially when the axial aqua ligands are removed via activation. FIG. 10 illustrates schematically the activation of HKUST-1. Activation gives unsaturated metal sites without affecting the rigid framework of the MOF [Schlichte, K.; Kratzke, T.; Kaskel, S.; *Microporous and Mesoporous Materials.* 2004, 73: 81-85.; and Lien T. L. Nguyen, Tung T. Nguyen, Khoa D. Nguyen, Nam T. S. Phan *Applied Catalysis A: General,* 2012, 425, 44-52.—each incorporated herein by reference in its entirety]. Schlichte, et al. first reported the catalytic activity of HKUST-1 when they used the HKUST-1 MOF for the trimethylcyanosilation of benzaldehyde. The open framework of this MOF was activated by removing the two water molecules from axial positions in the octahedral framework. The activated MOF afforded up to 57% conversion of benzaldehyde reaching a selectivity of 89% at 313 K. Nguyen, et al. studied the activity of HKUST-1 for the aza-michael reaction in which amines were reacted with α,β-unsaturated carbonyl groups to prepare β-amino carbonyl compounds and their derivatives. They achieved excellent conversions up to 100% under relatively mild conditions in the presence of 5 mol % activated catalyst. Fourier transform infrared spectroscopy (FT-IR) and powder X-ray diffraction (PXRD) analysis revealed that the catalyst could be reused several times without a significant reduction in its catalytic potency. Atomic absorption spectroscopy showed that the reaction was not influenced by homogeneous catalysis resulting from leached active species.

Using the same material, Phan, et al. was able to react phenols and aryl iodides to form diaryl ethers in an Ullman-type coupling reaction. The heterogeneous reaction leads to high conversion using 5 mol % catalyst in the presence of MeONa as a base. The used catalyst was facilely recovered from the reaction mixture using simple filtration and could be reused without significant degradation [Nam T. S. Phan, Tung T. Nguyen, Chi V. Nguyen, Thao T. Nguyen Applied Catalysis A: General., 2013, 457, 69-77.—incorporated herein by reference in its entirety]. Phan, et al. also reported the highly efficient activity of HKUST-1 for the C-arylation of acetylacetone in the presence of aryl iodides to obtain aryl ketones as major products. HKUST-1 was confirmed to be a true heterogeneous catalyst as there was no effect of homogeneous catalysis of active species leaching into the reaction mixture [Nam T. S. Phan, Tung T. Nguyen, Phuong Ho, and Khoa D. Nguyen *ChemCatChem.* 2013, 5, 1822-1831.—incorporated herein by reference in its entirety]. Dang, et al. studied the catalytic activity of HKUST-1 for the synthesis of propargylamine via direct oxidative C—C coupling reaction using C—H functionalization between phenylacetylene and N,N-dimethylaniline to give N-methyl-N-(3-phenylprop-2-ynyl)benzenamine as the principal product [Giao H. Dang, Duy T. Nguyen, Dung T. Le , Thanh Truong , Nam T. S. Phan *Journal of Molecular Catalysis A,* 2014, 300, 306.—incorporated herein by reference in its entirety]. The copper catalyzed reaction afforded 96% conversion after 180 minutes at 120° C. in the presence of 5 mol % copper-based catalyst. The used catalyst was recovered from the reaction medium by filtration and reused for the coupling reaction. Similarly, HKUST-1 has been used as a catalyst for the direct oxidative amination of sp$^2$ C—H bonds. The reaction involves the use of N-methylmorpholine oxide (NMO) as oxidizing agent in the presence of primary or secondary amine as coupling pairs with DMF as solvent at 90-100° C. [Nga T. T. Tran, Quan H. Tran, Thanh T. *Journal of Catalysis,* 2014, 320, 9-15.—incorporated herein by reference in its entirety].

In view of the forgoing, one object of the present disclosure is to provide relatively cheap and environmentally friendly metal organic framework catalysts designed towards laboratory and industrial scale catalytic applications as opposed to uses in gas storage and carbon capture. Metal organic framework catalysts provide great potential for new and existing chemical reactions for shortest route organic conversions that reduce industrial wastes and enable greener chemical processes through their high tunability, high surface area, stability, and reusability. Specifically, this disclosure is focused on isostructural HKUST-1 metal organic frameworks comprising zinc (II) metal ions and second metal ions, such as iron (II) ions, cobalt (II) ions, and copper (II) ions linked by 1,3,5-benzentricarboxylic acid to form a porous coordination network as polyhedral crystals. This disclosure provides the transmetallation preparation of these metal organic frameworks by post-synthetic metallic exchange of the solvothermally synthesized Zn-HKUST-1 metal organic framework. An additional aspect of the present disclosure is application of these metal organic frameworks as catalysts in methods for the liquid phase oxidation of cyclic hydrocarbons, such as, toluene, cyclohexane, and methylcyclohexane. It is envisioned that the metal organic frameworks of the present disclosure will exhibit strong activity in terms of conversion of the cyclic hydrocarbon, selectivity for a desired oxidized cyclic hydrocarbon product, and reusability. Overall, the metal organic frameworks are envisaged to exhibit strong potential utility as catalysts that aid the increasing demand for safer and energy saving reaction routes that additionally reduce and minimize the adverse environmental impact of industrial wastes.

BRIEF SUMMARY OF THE INVENTION

According to a first aspect, the present disclosure relates to a metal organic framework catalyst comprising i) zinc (II)

ions, ii) second metal ions which are not zinc (II) ions, and iii) benzene-1,3,5-tricarboxylic acid ligands, wherein the benzene-1,3,5-tricarboxylic acid ligands comprise carboxylate groups, each carboxylate group forming a coordinative bond to the zinc (II) ions or the second metal ions to form a coordination network in the form of porous polyhedral crystals that are isostructural to an HKUST-1 metal organic framework.

In one embodiment, the second metal ions are at least one selected from the group consisting of iron (II) ions, cobalt (II) ions, and copper (II) ions.

In one embodiment, the ratio of zinc (II) ions to the additional metal ions is in the range of 0.01 to 5.0.

In one embodiment, the porous polyhedral crystals have pores with an average diameter of 0.2-2.0 nm and a BET surface area in the range of 500-3000 $m^2/g$.

In one embodiment, the porous polyhedral crystals are octahedral or cubic with an average longest linear dimension in the range of 2-20 μm.

In one embodiment, the metal organic framework catalyst has a larger unit cell dimension a than the HKUST-1 metal organic framework.

In one embodiment, the second metal ions are copper (II) ions and the ratio of zinc (II) ions to copper (II) ions is in the range of 0.01 to 1.0.

In one embodiment, the second metal ions are at least one selected from the group consisting of iron (II) ions and cobalt (II) ions and the ratio of zinc (II) ions to the second metal ions is in the range of 0.5-5.0.

According to a second aspect, the present disclosure relates to a process for producing the metal organic framework in any of its embodiments comprising i) reacting 1,3,5-benzenetricarboxylic acid with a zinc (II) salt or hydrate in a solvent at a temperature greater than 25° C. to form a zinc modified metal organic framework and ii) transmetallating at least a portion of the zinc modified metal organic framework by immersing in a solution of a salt or hydrate of the second metal ions.

According to a third aspect, the present disclosure relates to a method for an oxidation of a cyclic hydrocarbon comprising contacting the cyclic hydrocarbon with the metal organic framework catalyst in any of its embodiments in the presence of a solvent and an oxidizing agent to form an oxidized cyclic hydrocarbon.

In one embodiment, the cyclic hydrocarbon is at least one selected from the group consisting of toluene, cyclohexane, and methylcyclohexane.

In one embodiment, the solvent is acetonitrile and the oxidizing agent is hydrogen peroxide.

In one embodiment, the contacting is performed at a temperature in the range of 40-100° C. for a time period of 2-36 hours.

In one embodiment, the cyclic hydrocarbon is toluene and 15-80% of the toluene is converted to the oxidized cyclic hydrocarbon at a reaction time of greater than 6 hours.

In one embodiment, the cyclic hydrocarbon is toluene and the method has a benzaldehyde selectivity in the range of 15-70% relative to a total amount of oxidized cyclic hydrocarbon products.

In one embodiment, the cyclic hydrocarbon is toluene and the method has a benzaldehyde selectivity relative to a total amount of oxidized cyclic hydrocarbon products greater than or equal to a benzaldehyde selectivity relative to a total amount of oxidized cyclic hydrocarbon products of a substantially similar method performed in a substantially similar manner with a substantially similar metal organic framework catalyst lacking the zinc (II) ions, the second metal ions, or both.

In one embodiment, the cyclic hydrocarbon is toluene and the second metal ions are iron (II) ions and the oxidation has a benzaldehyde selectivity of greater than 55% relative to a total amount of oxidized cyclic hydrocarbon products.

In one embodiment, the cyclic hydrocarbon is at least one selected from the group consisting of cyclohexane and methylcyclohexane and 10-60% of the cyclic hydrocarbon is converted to the oxidized cyclic hydrocarbon at a reaction time of greater than 12 hours.

In one embodiment, the cyclic hydrocarbon is cyclohexane and the method has a cyclohexane selectivity in the range of 45-80% relative to a total amount of oxidized cyclic hydrocarbon products.

In one embodiment, the method further comprises recovering and reusing the metal organic framework catalyst in at least 2 reaction iterations with a less than 20 percentage point decrease in conversion, selectivity, or both.

The foregoing paragraphs have been provided by way of general introduction, and are not intended to limit the scope of the following claims. The described embodiments, together with further advantages, will be best understood by reference to the following detailed description taken in conjunction with the accompanying drawings.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein.

DETAILED DESCRIPTION OF THE EMBODIMENTS

Figure 1:
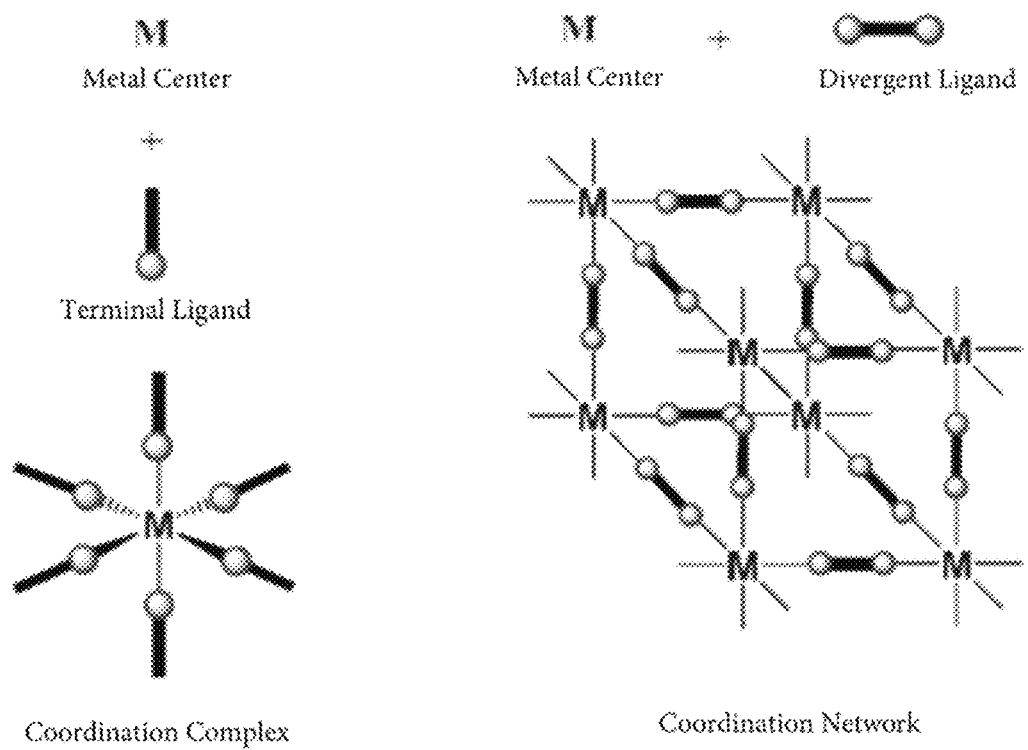
FIG. 1 is a schematic representation demonstrating the extension of the principles guiding the formation of metal coordination complexes to metal organic framework (MOF) coordination networks
Figure 2:
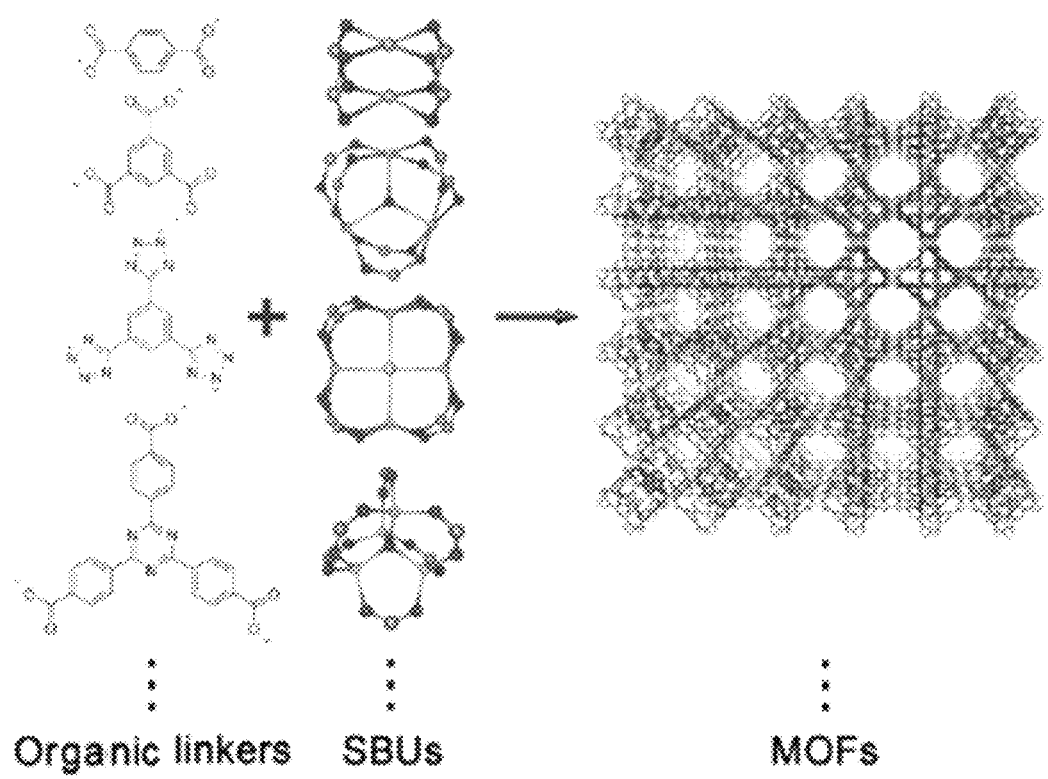
FIG. 2 is a schematic illustration of the synthesis and structure of metal organic frameworks (MOFs) from organic linkers and secondary building units (SBUs) comprising metal ions or clusters.
Figure 3A:
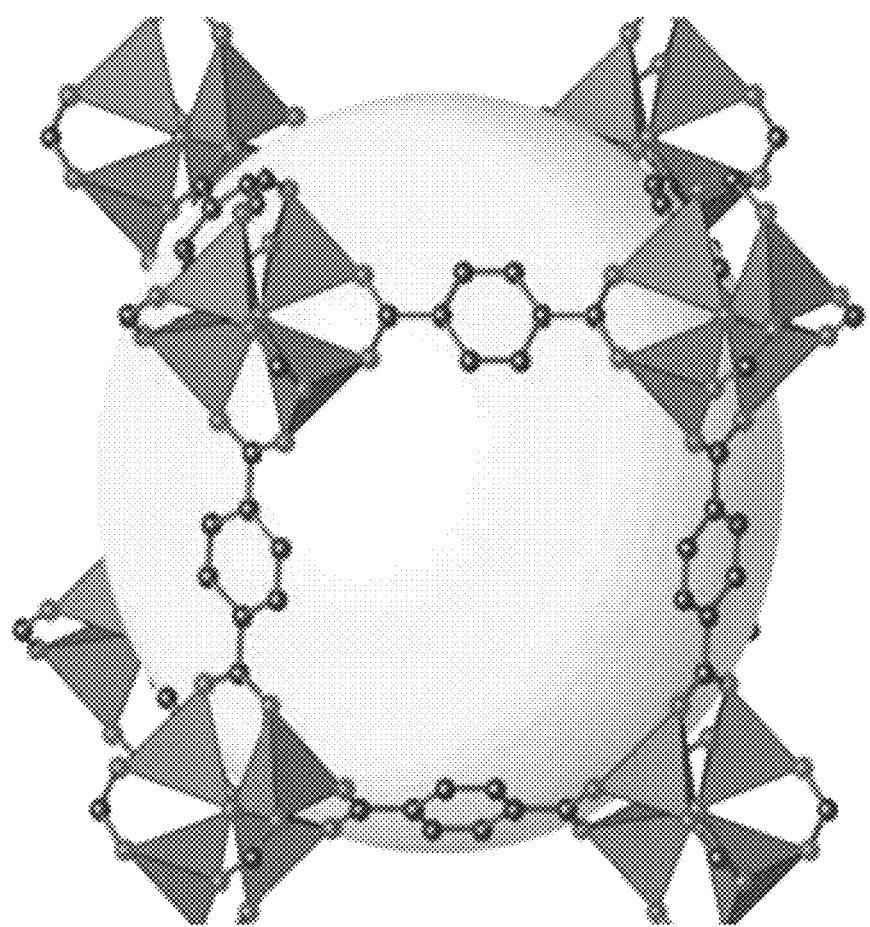
FIG. 3A is a schematic representation of MOF-5 represented as $ZnO_4$ tetrahedra linked by benzene dicarboxylate (BDC) organic linkers to form an extended 3D cubic framework with interconnected pores of approximately 8 Å aperture width and approximately 12 Å pore diameter as represented by the sphere.
Figure 3B:
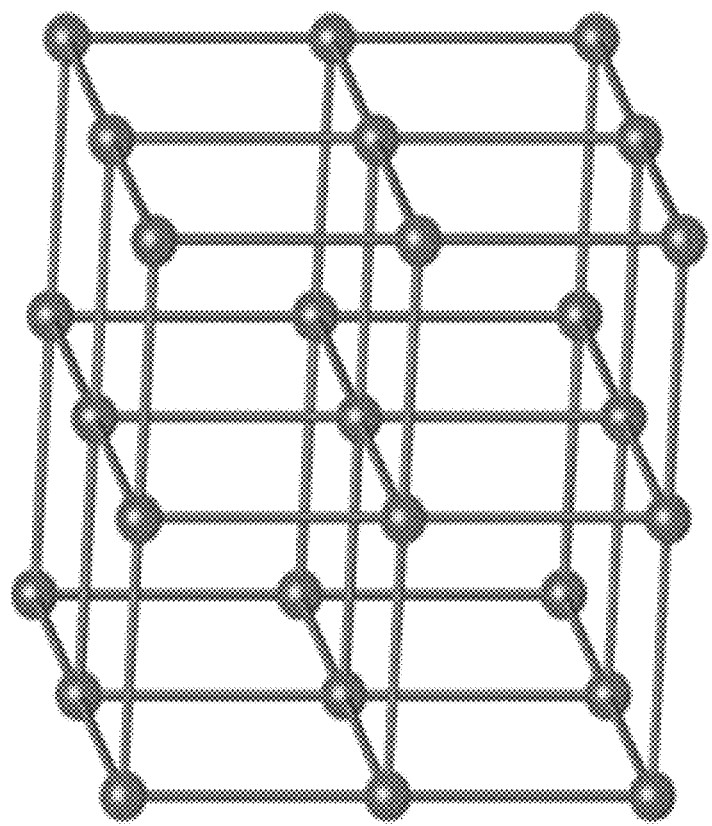
FIG. 3B is a schematic representation of the topology of the MOF-5 structure shown as a ball-and-stick model with $(OZn_4)O_{12}$ clusters as balls and benzene dicarboxylate (BDC) connectors as sticks.
Figure 3C:
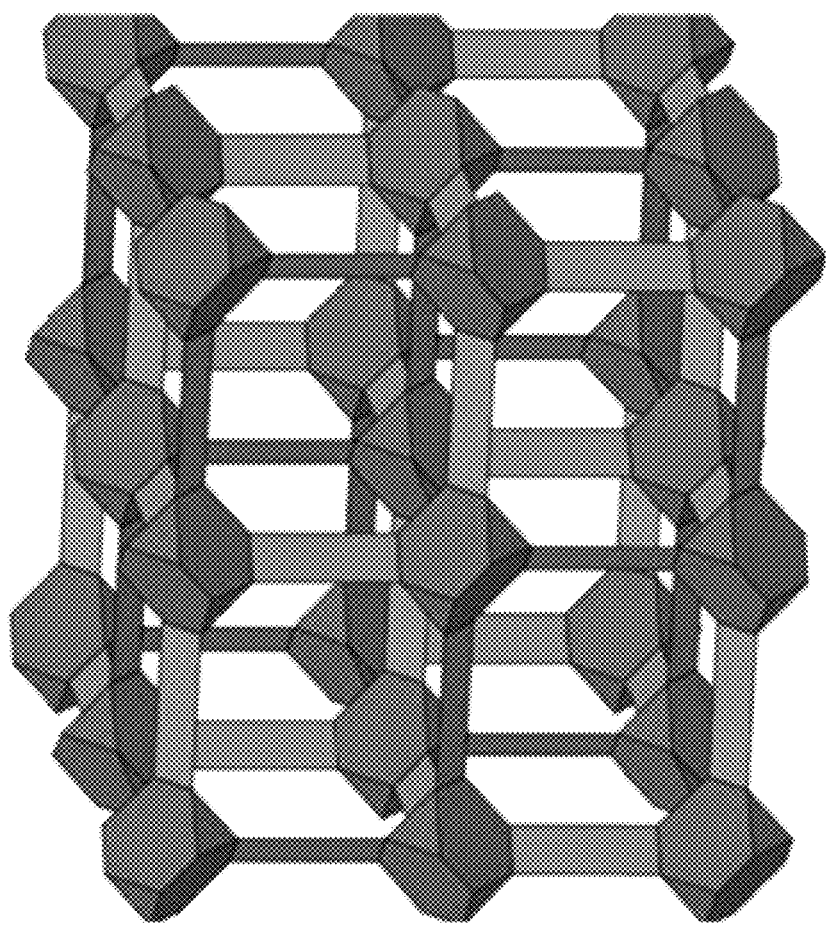
FIG. 3C is a schematic representation of the topology of the MOF-5 structure shown with tetrahedra representing $(OZn_4)O_{12}$ clusters and connections representing benzene dicarboxylate (BDC) ions where opposing lines are all at exactly 90°.
Figure 4:
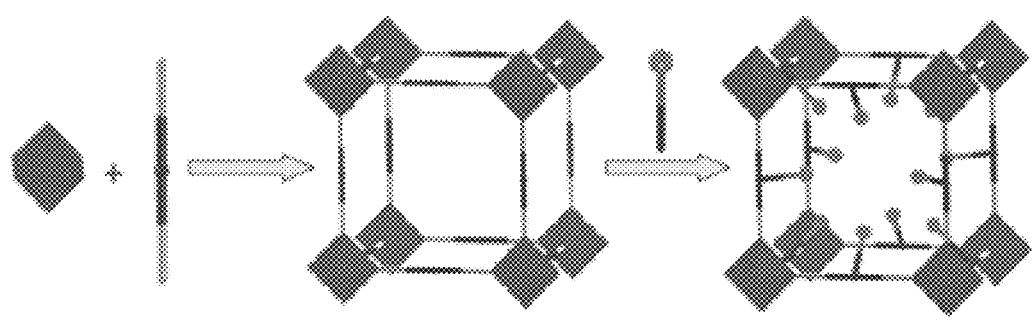
FIG. 4 is a general scheme for the post synthetic modification of MOFs.
Figure 5:
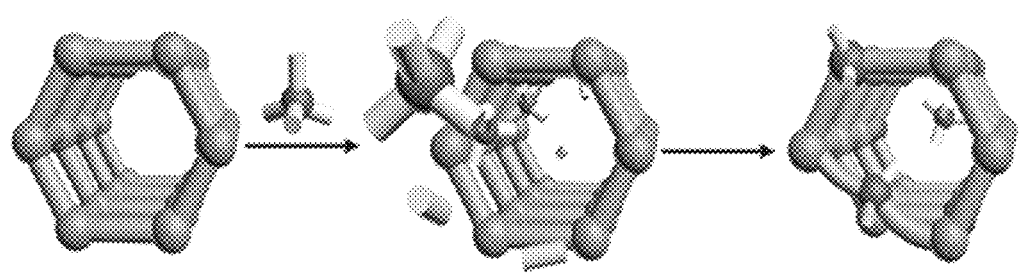
FIG. 5 is a general schematic diagram for post synthetic metal exchange of a MOF structure, or transmetallation of a MOF structure.
Figure 6:
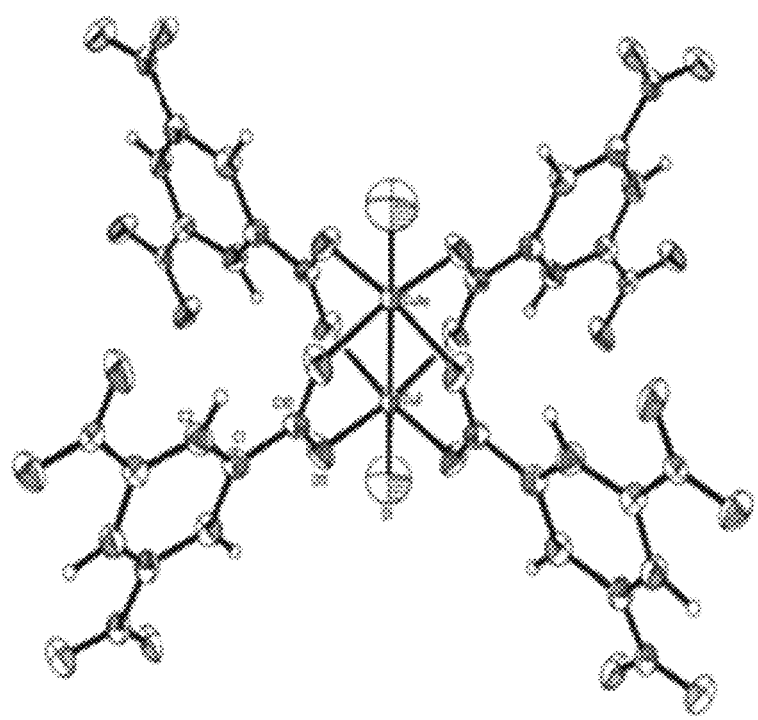
FIG. 6 is a single crystal structural analysis of a HKUST-1 dicopper (II) tetracarboxylate building block containing two axial aqua ligands.
Figure 7:
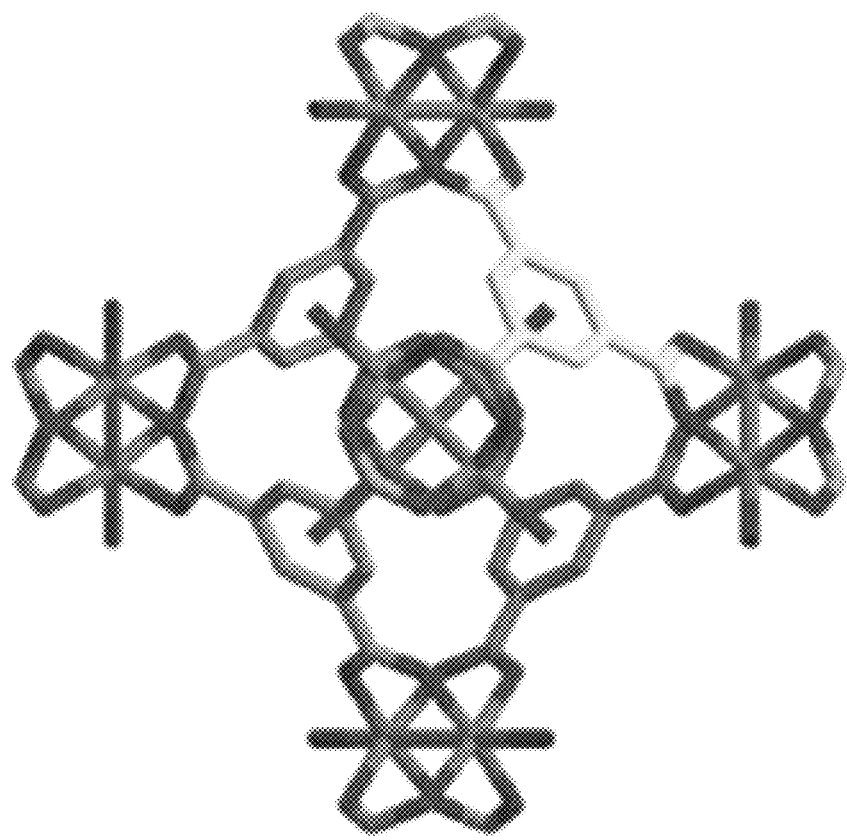
FIG. 7 is a schematic representation of a secondary building unit (SBU) of HKUST-1 showing the tbo net topology and paddlewheel structure where the tetracarboxylate unit provides a structural unit with four-fold symmetry and the trimesic acid provides a three-fold symmetry element.
Figure 8:
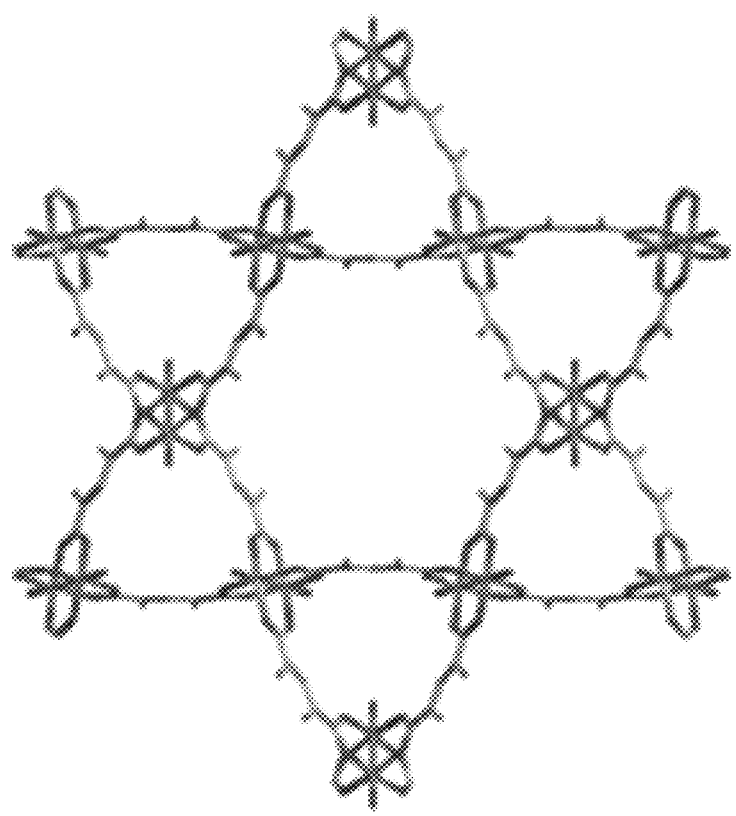
FIG. 8 is a schematic representation of the larger main octahedral secondary building unit (SBU) of HKUST-1 [$Cu_3(TMA)_2(H_2O)_3$] viewed along the cell body diagonal, showing a hexagonal-n shaped window at the intersection of the nanopores and giving rise to the nanochannels.
Figure 9:
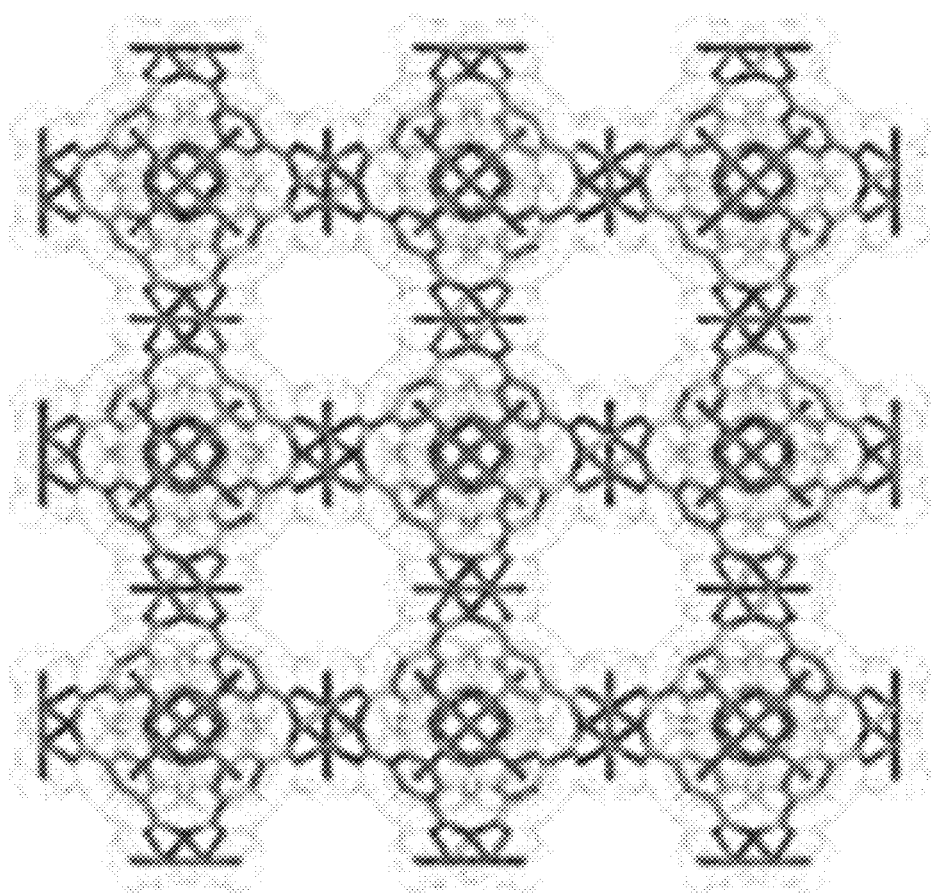
FIG. 9 is a schematic representation of the HKUST-1 polymer framework nanochannels with four-fold symmetry, formed from an octahedral secondary building unit (SBU) with $Cu_e$ at its 6 vertices and 4 trimesate ions tetrahedrally disposed as "panels" for four of the eight triangular faces of the octahedron
Figure 10:
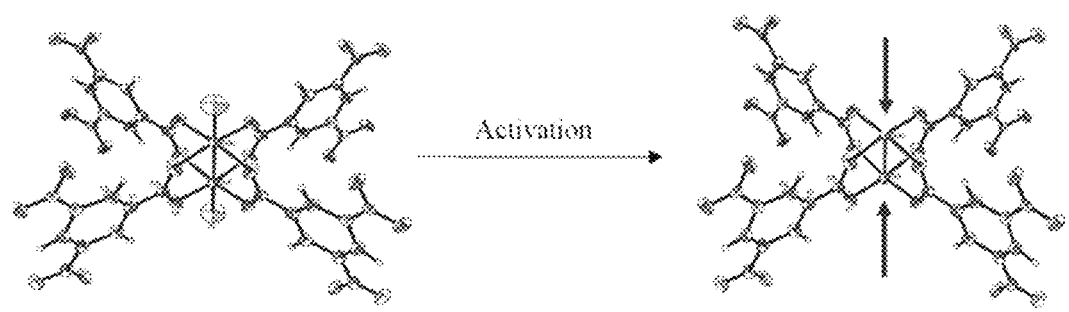
FIG. 10 is a general schematic representation of the activation of the HKUST-1 metal organic framework by removal of axial aqua ligands to give unsaturated metal sites without affecting the rigid framework of the MOF.

Referring now to the drawings, wherein, like reference numerals designate identical or corresponding parts throughout the several views. Embodiments of the present disclosure will now be described more fully hereinafter with reference to the accompanying drawings, in which some, but not all of the embodiments of the disclosure are shown.

Within the description of this disclosure, where a numerical limit or range is stated, the endpoints are included unless stated otherwise. Also, all values and subranges within a numerical limit or range are specifically included as if explicitly written out. As used herein, the words "a" and "an" and the like carry the meaning of "one or more". The phrases "selected from the group consisting of", "chosen from", and the like include mixtures of the specified materials. Terms such as "contain(s)" and the like are open terms meaning "including at least" unless otherwise specifically noted.

According to a first aspect, the present disclosure relates to a metal organic framework catalyst comprising i) zinc (II) ions, ii) second metal ions which are not zinc (II) ions, and iii) benzene-1,3,5-tricarboxylic acid ligands, wherein the benzene-1,3,5-tricarboxylic acid ligands comprise carboxylate groups, each carboxylate group forming a coordinative bond to the zinc (II) ions or the second metal ions to form a coordination network in the form of porous polyhedral crystals that are isostructural to an HKUST-1 metal organic framework.

As used herein, a metal organic framework (MOF) refers to compounds consisting of metal ions or clusters coordinated to organic ligands to form one, two, or three dimensional structures. They are a subclass of coordination polymers and are often porous. The organic ligands included are sometimes referred to as "struts", one preferable example being trimesic acid or benzene-1,3,5-tricarboxylic acid ($C_9H_6O_6$). More formally, a metal organic framework is a coordination network with organic ligands containing potential voids. As used herein, a coordination network is a coordination compound extending, through repeating coordination entities, in one dimension, but with cross-links between two or more individual chains, loops, or spirolinks, or a coordination compound extending through repeating coordination entities in two or three dimension; and finally a coordination polymer is a coordination compound with repeating coordination entities extending in one, two or three dimensions. In most cases, the pores are stable during elimination of the guest molecules (often solvents) and metal organic frameworks find use for the storage of gases such as hydrogen and carbon dioxide, gas purification, gas separation, catalysis, sensors, and supercapacitors.

Generally, metal organic frameworks (MOFs) are composed of two major components, (i) a metal ion or cluster of metal ions and (ii) an organic molecule called a linker. These materials may often be referred to as hybrid organic-inorganic materials. The organic units are typically mono-, di-, tri-, or tetravalent ligands. The choice of metal and linker dictates the structure and hence properties of the MOF. For example, the metal's coordination preference influences the size and shape of pores by dictating how many ligands can bind to the metal and in which orientation.

As used herein, catalysis is an increase in the rate of a chemical reaction due to the participation of an additional substance termed a catalyst. Reactions tend to occur faster with a catalyst because the reaction requires less activation energy. Furthermore, since they are not consumed in the catalyzed reaction, catalysts can continue to act repeatedly, and often only tiny amounts are require. As used herein, heterogeneous catalyst refers to catalysts where the phase of the catalyst differs from that of the reactants or substrates. As used herein, homogeneous catalyst refers to catalysts where the phase of the catalyst is the same as that of the reactants. In terms of the present disclosure, the metal organic framework in any of its embodiments may function as a heterogeneous catalyst, a homogeneous catalyst, or have components that function and have properties of both a heterogeneous catalyst and a homogeneous catalyst. In a preferred embodiment, the metal organic framework catalyst of the present disclosure in any of its embodiments functions as a heterogeneous catalyst. Preferably the metal organic framework catalyst composition is employed in at least one chemical transformation, preferably an oxidation, preferably a selective oxidation Metal organic frameworks (MOFs) may often be employed as heterogeneous catalysts. Their high surface area, tunable porosity, diversity in metal and functional groups make them especially attractive for use as catalysts. Similarly, zeolites are often employed in catalysis; however, zeolites are limited by the fixed tetrahedral coordination of the Si/Al connecting points and the two-coordinated oxide linkers and only approximately 200 zeolites are known. In contrast with this limited scope, MOFs exhibit more diverse coordination geometries, polytopic linkers, and ancillary ligands (i.e. $F^-$, $OH^-$, $H_2O$ among others). It is also challenging to obtain zeolites with pore sizes larger than 1 nm, which limits the catalytic applications of zeolites to relatively small organic molecules (typically no larger than xylenes). Furthermore, mild synthetic conditions typically employed for MOF synthesis allow direct incorporation of delicate functionalities into the framework structures. Such a process would not be possible with zeolites or other microporous crystalline oxide-based materials because of the harsh conditions typically used for their synthesis (e.g. calcination at high temperatures to remove organic templates).

Additionally, zeolites still cannot be obtained in enantiopure form, which precludes their applications in catalytic asymmetric synthesis, essential for use in the pharmaceutical, agrochemical and fragrance industries. Enantiopure chiral ligands or their metal complexes have been incorporated into MOFs leading to efficient asymmetric catalysts. Even some MOF materials may bridge the gap between zeolites and enzymes when they combine isolated polynuclear sites, dynamic host-guest responses, and a hydrophobic cavity environment. Theoretical calculations show that MOFs are semiconductors or insulators with band gaps between 1.0 and 5.5 eV which can be altered by changing the degree of conjugation in the ligands indicating the further possibility of their use as photocatalysts. Like other heterogeneous catalysts, MOFs may allow for easier post-reaction separation and recyclability than homogeneous catalysts. In several cases, they also give highly enhanced catalyst stability. Further, MOFs typically offer substrate-size selectivity.

Generally, the metal ions, preferably transition metal ions, used can generate a wide range of structures. The properties of these metals, including the oxidation state and coordination number, preferably 2 to 7, produce a linear, trigonal, square planar, tetrahedral, trigonal pyramidal, trigonalbipyramidal, octahedral, and pentagonal bipyramidal geometries as well as some distorted forms. In a preferred embodiment, the metal organic framework of the present disclosure in any of its embodiments comprises zinc (II) ions and second metal ions which are not zinc (II) ions. Exemplary suitable second metal ions include, but are not limited to, Ag, Ca, K, Zn, Na, Pb, Mn, Fe, Co, Ni, Al, Cu, Sn, Cd, Hg, Cr, Fe, Bi, Ga, Ge, Au, In, Tl, Rb, Cs, As, Sb, Cr, Zn, V, Pt, Pd, Rh, and mixtures thereof. Further, these metal ions may be of any oxidation state $M^{+1}$, $M^{+2}$, $M^{+3}$, etc., preferably $M^{+2}$. In a preferred embodiment, the second metal ions are at least one selected from the group consisting of $Ag^+$, $Al^{3+}$, $Bi^{3+}$, $Ce^{4+}$, $Cr^{3+}$, $Co^{2+}$, $Cu^{2+}$, $Fe^{3+}$, $Mn^{2+}$, $Mg^{2+}$, $Pd^{2+}$, $Sc^{3+}$, $V^{4+}$, $Zn^{2+}$, and $Zr^{4+}$. In a most preferred embodiment the second metal ions are at least one selected from the group consisting of iron (II) ions, cobalt (II) ions, and copper (II) ions. It is equally envisaged that the metal organic framework of the present disclosure may be adapted to further comprise one or more additional metal ions in addition to or in lieu of the zinc (II) metal ions and second metal ions. Exemplary additional metal ions include, but are not limited to, an alkali metal (Li, Na, K, etc.), an alkaline earth metal (Mg, Ca, Sr, etc.) a lanthanide metal (La, Ce, Eu, Yb, etc.), an actinide metal (Ac, Th, etc.), or a post-transition metal (Al, Sn, Pb, In, etc.).

In the formation of a metal organic framework, the organic linkers must meet certain requirements to form coordination bonds, primarily being multidentate, having at least two donor atoms (i.e. N—, O—, and/or S—) and being neutral and being neutral or anionic. The structure of the metal organic framework is also affected by the shape, length, and functional groups present in the organic linker. In certain embodiments, the metal organic framework of the present disclosure comprises anionic ligands as organic linkers, preferably polycarboxylates including, but not limited to, di-, tri-, tetra-, and/or hexacarboxylates. In a preferred embodiment, the metal organic framework of the present disclosure in any of its embodiments comprises benzene-1,3,5-tricarboxylic acid (trimesic acid, $C_9H_6O_6$) ligands as the ligands, linkers, or struts. The benzene-1,3, 5-tricarboxylic acid ligands comprise carboxylate groups, with each carboxylate groups forming a coordinative bond to the zinc (II) metal ions or the second metal ions as the nodes, metal ions, or clusters of metal ions to form a coordination network. It is equally envisaged that the metal organic framework of the present disclosure may be adapted to further comprise one or more additional organic ligands in addition to or in lieu of the benzene-1,3,5-tricarboxylic acid ligands including, but not limited to, bidentate carboxylics, tridentate carboxylates, azoles, neutral ligands, and squaric acid (3,4-dihydroxy-3-cyclobutene-1,2-dione, $C_4H_2O_4$). Exemplary suitable bidentate carboxylics include, but are not limited to oxalic acid (ethanedioic acid, HOOC—COOH), malonic acid (propanedioic acid, HOOC—$(CH_2)$—COOH), succinic acid (butanedioic acid, HOOC—

(CH$_2$)$_2$—COOH), glutaric acid (pentanedioic acid, HOOC—(CH$_2$)$_3$—COOH), phthalic acid (benzene-1,2-dicarboxylic acid, o-phthalic acid, C$_6$H$_4$(COOH)$_2$), isophthalic acid (benzene-1,3-dicarboxylic acid, m-phthalic acid, C$_6$H$_4$(COOH)$_2$), terephthalic acid (benzene-1,4-dicarboxylic acid, BDC, p-phthalic acid, C$_6$H$_4$(COOH)$_2$), biphenyl-4,4'-dicarboxylic acid, BPDC, HOOC—(C$_6$H$_4$)$_2$—COOH), and the like. Exemplary tridentate carboxylates include, but are not limited to, citric acid (2-hydroxy-1,2,3-propanetricarboxylic acid, (HOOC)CH$_2$C(OH(COOH)CH$_2$(COOH), trimesic acid, and the like. Exemplary azoles include, but are not limited to, 1,2,3-triazole (1H-1,2,3-triazole, C$_2$H$_3$N$_3$), pyrrodiazole (1H-1,2,4-triazole, C$_2$H$_3$N$_3$), and the like. Exemplary suitable neutral ligands included, but are not limited to, piperazine and 4,4'-bipyridine.

In a preferred embodiment, 5-80% of the total metal ions present in the metal organic framework catalyst of the present disclosure in any of its embodiments are zinc (II) ions, preferably 6-75%, preferably 7-70%, preferably 8-68%, preferably 10-66%, preferably 15-50%, preferably 20-40% of the total metal ions present in the metal organic framework catalyst of the present disclosure in any of its embodiments are zinc (II) ions. In a preferred embodiment, 20-95% of the total metal ions present in the metal organic framework catalyst of the present disclosure in any of its embodiments are not zinc (II) ions, preferably 25-94%, preferably 30-92%, preferably 32-91%, preferably 34-90%, preferably 50-85%, preferably 60-80% of the total metal ions present in the metal organic framework catalyst of the present disclosure in any of its embodiments are not zinc (II) ions. In a preferred embodiment, the second metal ions are copper (II) ions and 60-95% of the total metal ions present in the metal organic framework catalyst of the present disclosure in any of its embodiments are copper (II) ions, preferably 65-94%, preferably 70-93%, preferably 75-92%, preferably 80-91%, preferably 85-90% of the total metal ions present in the metal organic framework catalyst of the present disclosure in any of its embodiments are copper (II) ions. In a preferred embodiment, the second metal ions are at least one selected from the group consisting of iron (II) ions and cobalt (II) ions and 5-60% of the total metal ions present in the metal organic framework catalyst of the present disclosure in any of its embodiments are at least one selected from the group consisting of iron (II) ions and cobalt (II) ions, preferably 10-55%, preferably 15-50%, preferably 20-45%, preferably 25-40%, preferably 30-38%, preferably 32-36% of the total metal ions present in the metal organic framework catalyst of the present disclosure in any of its embodiments are at least one selected from the group consisting of iron (II) ions and cobalt (II) ions.

In a preferred embodiment, the ratio of zinc (II) ions to the additional metal ions is in the range of 0.01 to 5.0, preferably 0.02 to 4.0, preferably 0.04 to 3.5, preferably 0.06 to 3.0, preferably 0.08 to 2.5, preferably 0.1 to 2.0. In a preferred embodiment, the second metal ions are copper (II) ions and the ratio of zinc (II) ions to copper (II) ions is in the range of 0.01 to 1.0, preferably 0.02 to 0.9, preferably 0.03 to 0.8, preferably 0.04 to 0.7, preferably 0.05 to 0.6, preferably 0.06 to 0.5, preferably 0.07 to 0.4, preferably 0.08 to 0.3, preferably 0.09 to 0.2, preferably 0.095 to 0.15, preferably 0.1 to 0.125. In a preferred embodiment, the second metal ions are at least one selected from the group consisting of iron (II) ions and cobalt (II) ions and the ratio of zinc (II) ions to the second metal ions is in the range of 0.5 to 5.0, preferably 0.75 to 4.5, preferably 1.0 to 4.0, preferably 1.25 to 3.5, preferably 1.5 to 3.0, preferably 1.75 to 2.5, preferably 1.8 to 2.25, preferably 1.9 to 2.20.

In a preferred embodiment, the benzene-1,3,5-tricarboxylic acid ligands comprise carboxylate groups, with each carboxylate groups forming a coordinative bond to the zinc (II) metal ions or the second metal ions to form a coordination network in the form of porous polyhedral crystals that are isostructural to an HKUST-1 metal organic framework. As used herein, isostructural refers to chemical compounds having similar chemical structures. As used herein, isomorphous when used in relation to crystal structures is essentially synonymous. Two crystals are said to be isostructural if they have the same structure, but not necessarily the same cell dimensions not the same chemical composition, and with a "comparable" variability in the atomic coordinates to that of the cell dimensions and chemical composition. Isostructural may further refer to isostructural series of isostructural polymorphs or isostructural phase transitions. Many minerals are isostructural when they differ only in the nature of a cation. The term isotypic may be used as synonymous with isostructural. For example, borazine is isostructural with benzene, indium (I) bromide is isostructural with β-thallium (I) iodide, and I-Gold (I) bromide is isostructural with gold (I) chloride. Additionally, isostructural may further refer to compounds which are isoelectronic which usually have similar chemical structures, such as, for example methane, CH$_4$, and the ammonium ion, NH$_4^+$, which are both isoelectric and isostructural as both have a tetrahedral structure, the C—H and N—H bond lengths are different and crystal structures are different.

In a preferred embodiment, the metal organic framework forms a highly porous metal-coordination polymer [M$_3$(BTC)$_2$(H$_2$O)$_3$]$_n$ (wherein BTC is benzene-1,3,5-tricarboxylate and M is zinc (II) and/or the second metal, preferably iron (II), copper (II), and cobalt (II)0 which has interconnected [M$_2$(O$_2$CR)$_4$] units, C$_{18}$H$_{12}$O$_{15}$M$_3$ (wherein R is an aromatic ring). Preferably, this creates a 3-dimensional system of channels with a pore size of 0.2-2.0 nm, preferably 0.3-1.9 nm, preferably 0.4-1.8 nm, preferably 0.5-1.7 nm, preferably 0.6-1.8 nm, preferably 0.7-1.6 nm, preferably 0.8-1.5 nm, preferably 0.9-1.4 nm, preferably 1.0-1.3 nm, preferably 1.1-1.2 nm and an accessible porosity of greater than 30% in the solid. The polymer framework is composed of dimeric metallic tetracarboxylate building units with a metal ion inter nuclear separation of 2-3 Å, preferably 2.2-2.8 Å, preferably 2.4-2.7 Å, preferably 2.5-2.65 Å. The framework is preferably neutral because the twelve carboxylate oxygens from the two BTC ligands bind to four coordination sites for each of the three M$^{2+}$ ions of the formula unit. Hence teach metal atom completes its pseudo-octahedral coordination sphere with the presence of axial aqua ligands opposite to the M-M dimer. The tetracarboxylate unit provides a structural motif with potential four-fold symmetry, and the trimesic acid provides a three-fold symmetry element. The origin of the nano-challels can be considered to arise from the formation of larger octahedral secondary building units (SBUs). Preferably, the main SBU in the metal organic framework catalyst of the present disclosure is the octahedral unit with M$_2$ at its 6 vertices and 4 trimesate ions tetrahedrally disposed as "panels" for four of the eight triangular faces of the octahedron. The framework may be composed of an array of 32 M-M paddlewheels per crystallographic unit cell, connected in three dimensions by 1,3,5-benzene tricarboxylate. This ligand arrangement results in two coordinatively unsaturated M sites per paddlewheel which polar molecules can interact with. The paddlewheels are preferably stable in both the coordinatively saturated and unsaturated arrangements. It is possible to prepare the metal organic framework of the present disclosure that crystallizes with stoichiometric amounts of water coordinated to each $M^{2+}$ ion. Anhydrous (or "activated") metal organic framework catalyst where the axial aqua ligands are removed giving unsaturated metal sites by gentle heating under low pressure and or by soaking in a polar protic solvent or non-polar solvent, preferably dichloromethane or methanol resulting in the chemically activated metal organic framework catalyst with exposed $M^{2+}$ sites.

In certain embodiments, the metal organic framework of the present disclosure may be considered a Lewis acid solid or to possess Lewis character, especially at the metal sites $M^{2+}$ of the trinuclear networks. The structure of such metal organic frameworks is composed of the secondary building unit with tetracoordinate metal centers in axial position of easy access offering a high concentration of Lewis acidic sites and $M^{2+}$ ions that are exposed on the surface of the framework and might serve as potent Lewis acids. As used herein, a Lewis acid catalyst or Lewis acid catalysis refers to organic reactions wherein a metal-based Lewis acid acts as an electron pair acceptor to increase the reactivity of a substrate. Common Lewis acid catalyst are based on main group metals including, but not limited to, aluminum, boron, silicon, and tin, as well as many early (i.e. titanium, zirconium) and late (i.e. iron, copper, zinc) d-block metals. Generally, the metal atom forms an adduct with a lone-pair bearing electronegative atom in the substrate such as oxygen (both $sp^2$ or $sp^3$), nitrogen, sulfur, and/or halogens. The complexation generally has partial charge-transfer character and makes the lone-pair donor effectively more electronegative, activating the substrate toward nucleophilic attack, heterocyclic bond cleavage, or cycloaddition. Many reactions, such as for example, selective oxidation, involving carbon-carbon or carbon-heteroatom bond formation can be catalyzed by Lewis acids.

In a preferred embodiment, the metal organic framework of the present disclosure forms porous polyhedral crystals, the polyhedral crystals are preferably octahedral or cubic in shape with an average diameter or longest linear dimension of 2-20 µm, preferably 4-18 µm, preferably 6-16 µm, preferably 8-14 µm, preferably 9-13 µm, preferably 10-12 µm, preferably 11.1-11.9 µm.

In crystallography, crystal structure is a description of the ordered arrangement of atoms, ions or molecules in a crystalline material. Ordered structures occur from the intrinsic nature of the constituent particles to form symmetric patterns that repeat along the principal directions of three dimensional space in matter. The smallest group of particles in the material that constitutes the repeating pattern is the unit cell of the structure. The unit cell completely defines the symmetry and structure of the entire crystal lattice, which is built up by repetitive translation of the unit cell along its principal axes. The repeating pattern is said to be located at the points of the Bravais lattice. The lengths of the principal axes, or edges, of the unit cell and the angles between them are the lattice constants, or lattice parameters, the symmetry properties of the crystal are described by the concept of space groups. The crystal structure and symmetry play a critical role in determining many physical properties. Subunits of metal organic frameworks, termed secondary building units (SBU) can be described by topologies common to several structures. Each topology, also called a net, is assigned a symbol, consisting of three lower-case letters. In a preferred embodiment, the metal organic framework catalyst of the present disclosure in any of its embodiments crystallizes with a structural topology referred to as the tbo type in space group Fm3m which relates to "twisted" boracite.

The crystal structure of a material (the arrangement of atoms within a given type of crystal) can be described in terms of its unit cell. The unit cell is a box containing one or more atoms arranged in three dimensions. The unit cells stacked in three dimensional space describe the bulk arrangement of atoms of the crystal. The unit cell is represented in terms of its lattice parameters, which are the lengths of the cell edges (a, b, and c) and the angles between them (alpha, beta and gamma), while the positions of the atoms inside the unit cell are described by the set of atomic positions ($x_i$, $y_i$, $z_i$) measured from a reference lattice point. Commonly atomic positions are represented in terms of fractional coordinates, relative to the unit cell lengths. In a preferred embodiment, the metal organic framework catalyst of the present disclosure in any of its embodiments has a larger unit cell dimension a (length of cell edge) than the HKUST-1 metal organic framework, preferably at least a 0.025 Å larger unit cell dimension a, preferably at least 0.05 Å larger, preferably at least 0.075 Å larger, preferably at least 0.10 Å larger, preferably at least 0.125 Å larger, preferably at least 0.15 Å larger, preferably at least 0.175 Å larger, preferably at least 0.2 Å larger, preferably at least 0.25 Å larger, preferably at least 0.3 Å larger unit cell dimension a.

Porosity is defined as the percentage of void space in a solid. As used herein, porous materials are those where the void space is deliberately introduced to fulfill certain functions. Total porosity (volume fraction of pores) is defined as $\phi=1-\rho_r$, where $\rho_r=\rho/\rho_0$ and is the relative density of the solid phase matrix or skeleton ($\rho$=bulk density and $\rho_0$=theoretical density). It is expressed as a percentage of the theoretical density (TD) of the solid as a whole. In a preferred embodiment, the metal organic framework catalyst of the present disclosure has a percent porosity of at least 30%, preferably at least 35%, preferably at least 40%, preferably at least 45%, preferably at least 50%, preferably at least 55%, preferably at least 60%, preferably at least 65%, preferably at least 70%.

In a preferred embodiment, the metal organic framework catalyst of the present disclosure in any of its embodiments forms porous polyhedral crystals having pores with an average diameter or aperture of 0.2-2.0 nm, preferably 0.3-1.9 nm, preferably 0.4-1.8 nm, preferably 0.5-1.7 nm, preferably 0.6-1.8 nm, preferably 0.7-1.6 nm, preferably 0.8-1.5 nm, preferably 0.9-1.4 nm, preferably 1.0-1.3 nm, preferably 1.1-1.2 nm. In certain embodiments, the metal organic framework catalyst of the present disclosure features three distinct internal pores, two of comparable size (0.8-1.6 nm, preferably 0.9-1.4 nm) and a smaller pore (0.2-1.4 nm, preferably 0.8-1.2 nm, or about). One of the two larger pores preferably features metal ion bonds to metal ions (M-M) directed into the pores. In certain embodiments, the metal organic framework may comprise square shaped pores of 0.2-2.0 nm by 0.2-2.0 nm.

As used herein, bulk density is a property of powders, granules and other "divided" solids, especially used in reference to mineral components and chemical substances or any other masses of corpuscular or particulate matter. It is defined as the weight of many particles of the material divided by the total volume they occupy. The total volume includes particle volume, inter-particle void volume, and internal pore volume. In a preferred embodiment, the metal organic framework of the present disclosure in any of its embodiments has a bulk density of 0.1-1.0 g/cm$^3$, preferably 0.15-0.8 g/cm$^3$, preferably 0.2-0.6 g/cm$^3$, preferably 0.25-0.4 g/cm$^3$, preferably 0.3-0.35 g/cm$^3$.

The Brunauer-Emmet-Teller (BET) theory aims to explain the physical adsorption of gas molecules on a solid surface and serves as the basis for an important analysis technique for the measurement of the specific surface area of a material. Specific surface area is a property of solids which is the total surface area of a material per unit of mass, solid or bulk volume, or cross sectional area. In a preferred embodiment the metal organic framework catalyst of the present disclosure in any of its embodiments has a BET surface area in the range of 500-3000 m$^2$/g, preferably 750-2500 m$^2$/g, preferably 1000-2000 m$^2$/g, preferably 1250-1750 m$^2$/g, preferably 1400-1600 m$^2$/g, or about 1500 m$^2$/g.

According to a second aspect, the present disclosure relates to a process for producing the metal organic framework in any of its embodiments comprising i) reacting 1,3,5-benzenetricarboxylic acid with a zinc (II) salt or hydrate in a solvent at a temperature greater than 25° C. to form a zinc modified metal organic framework and ii) transmetallating at least a portion of the zinc modified metal organic framework by immersing in a solution of a salt or hydrate of the second metal ions.

The physicochemical characteristics of metal organic frameworks can be modulated and many of these properties can be modified in the material from the synthesis process. In a preferred embodiment, the metal organic framework of the present disclosure is produced by a solvothermal method. Typically the solvothermal synthesis comprises the reaction of one or more metal salts and one or more organic ligands in the presence of preferably organic solvents or mixtures, preferably involving formamide, alcohols, or pyrrolidones. Important parameters in the solvothermal synthesis include, but are not limited to, temperature, concentration of reactants (which can be varied over a wide range) and pH of the reaction solution. It is equally envisaged that the present process in any of its embodiments may be adapted to produce the metal organic framework of the present disclosure in any of its embodiments by other methods of synthesis which may be used to tailor the properties of the metal organic framework. Exemplary suitable methods that may be used in addition to or in lieu of a solvothermal method include, but are not limited to, mechanochemical methods, electrochemistry methods, assisted synthesis methods (i.e. by ultrasound or microwave), and subcritical water methods.

In one step of the process, 1,3,5-benzentricarboxylic acid is reacted with a zinc (II) salt or hydrate in a solvent at a temperature greater than 25° C. to form a zinc modified metal organic framework.

As used herein, the term "solvent" refers to and includes, but is not limited to, water (e.g. tap water, distilled water, deionized water, deionized distilled water), organic solvents, such as ethers (e.g. diethyl ether, tetrahydrofuran, 1,4-dioxane, tetrahydropyran, t-butyl methyl ether, cyclopentyl methyl ether, di-iso-propyl ether), glycol ethers (e.g. 1,2-dimethoxyethane, diglyme, triglyme), alcohols (e.g. methanol, ethanol, trifluoroethanol, n-propanol, i-propanol, n-butanol, i-butanol, t-butanol, n-pentanol, i-pentanol, 2-methyl-2-butanol, 2-trifluoromethyl-2-propanol, 2,3-dimethyl-2-butanol, 3-pentanol, 3-methyl-3-pentanol, 2-methyl-3-pentanol, 2-methyl-2-pentanol, 2,3-dimethyl-3-pentanol, 3-ethyl-3-pentanol, 2-methyl-2-hexanol, 3-hexanol, cyclopropylmethanol, cyclopropanol, cyclobutanol, cyclopentanol, cyclohexanol), aromatic solvents (e.g. benzene, o-xylene, m-xylene, p-xylene, mixtures of xylenes, toluene, mesitylene, anisole, 1,2-dimethoxybenzene, α,α,α-trifluoromethylbenzene, fluorobenzene), chlorinated solvents (e.g. chlorobenzene, dichloromethane, 1,2-dichloroethane, 1,1-dichloroethane, chloroform), ester solvents (e.g. ethyl acetate, propyl acetate), amide solvents (e.g. dimethylformamide, dimethylacetamide, N-methyl-2-pyrrolidone), urea solvents, ketones (e.g. acetone, butanone), acetonitrile, propionitrile, butyronitrile, benzonitrile, dimethyl sulfoxide, ethylene carbonate, propylene carbonate, 1,3-dimethyl-3,4,5,6-tetrahydro-2(1H)-pyrimidinone, and mixtures thereof As used herein solvent may refer to non-polar solvents (e.g. hexane, benzene, toluene, diethyl ether, chloroform, 1,4-dioxane), polar aprotic solvents (e.g. ethyl acetate, tetrahydrofuran, dichloromethane, acetone, acetonitrile, dimethylformamide, dimethyl sulfoxide) and polar protic solvents (e.g. acetic acid, n-butanol, isopropanol, n-propanol, ethanol, methanol, formic acid, water) and mixtures thereof.

In a preferred embodiment, the reacting is performed in a non-polar solvent. Exemplary suitable non-polar solvents include, but are not limited to, pentane, cyclopentane, hexane, cyclohexane, benzene, toluene, 1,4-dioxane, chloroform, diethyl ether, dichloromethane and mixtures thereof, preferably the solvent is dichloromethane. It is equally envisaged that the present process may be adapted to incorporate polar protic solvent including, but not limited to, formic acid, n-butanol, isopropanol, n-propanol, ethanol, methanol, acetic acid, and water, as well as polar aprotic solvents including, but not limited to, tetrahydrofuran, ethyl acetate, acetone, dimethylformamide, acetonitrile, dimethyl sulfoxide, nitromethane, propylene carbonate and mixtures thereof.

As used herein, a salt refers to an ionic compound resulting from the neutralization reaction of an acid and a base. Salts are composed of related numbers of cations (positively charged ions) and anions (negative ions) such that the product is electrically neutral (without a net charge). These component ions can be inorganic (i.e. chloride, $Cl^-$) or organic (i.e. acetate, $CH_3CO_2^-$) and can be monoatomic (i.e. fluoride, $F^-$) or polyatomic (i.e. sulfate, $SO_4^{2-}$). Exemplary conventional salts include, but are not limited to, those derived from inorganic acids including, but not limited to, hydrochloric, hydrobromic, sulfuric, sulfamic, phosphoric, and nitric; and those derived from organic acids including, but not limited to, acetic, propionic, succinic, glycolic, stearic, lactic, malic, tartaric, citric, ascorbic, pamoic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isethionic, and mixtures thereof and the like.

As used herein, a solvate refers to a physical association of a compound with one or more solvent molecules, whether organic or inorganic, preferably water in a hydrate. This physical association may include hydrogen bonding. In certain instances the solvent molecules may be incorporated in the crystal lattice of the crystalline solid. The solvent molecules may be present in a regular arrangement and/or a non-ordered arrangement. The solvate may comprise either a stoichiometric or nonstoichiometric amount of the solvent molecules. Solvate encompasses both solution phase and isolable solvates. As used herein, a hydrate is a substance that contains water or its constituent elements. The chemical state of the water varies widely between different classes of hydrates. In organic chemistry, a hydrate is a compound formed by the addition of water or its elements to another molecule. Many organic molecules, as well as inorganic molecules, form crystals that incorporate water into the crystalline structure without chemical alteration of the organic molecule. In inorganic chemistry, hydrates are inorganic salts containing water molecules combined in a definite ratio as an integral part of the crystal that are either bound to a metal center or that have crystallized with the metal complex. The notation of a hydrated compound (n-$H_2O$) where n is a number of water molecules per formula unit of the salt is commonly used to show that a salt is hydrated. The n is usually a low integer, though it is possible for fractional values to occur.

Exemplary zinc salts or hydrates include, but are not limited to, zinc nitrate ($Zn(NO_3)_2$), zinc chlorate $Zn(ClO_3)_2$, zinc sulfate ($ZnSO_4$), zinc phosphate ($Zn_3(PO_4)_2$) zinc molybdate ($ZnMoO_4$), zinc chromate ($ZnCrO_4$), zinc arsenite ($Zn(AsO_2)_2$), zinc arsenate octahydrate ($Zn(AsO_4)_2.8H_2O$), zinc acetate ($Zn(O_2CCH_3)_2$), zinc bromide, zinc bromide dehydrate, zinc chloride, zinc citrate dihydrate, zinc cyanide, zinc fluoride, zinc hexafluorosilicate, zinc iodide, zinc methacrylate, zinc nitrate hydrate, zinc oxalate hydrate, zinc perchlorate hexahydrate, zinc selenite, zinc sulfate heptahydrate, zinc tetrafluoroborate hydrate, zinc p-toluenesulfonate hydrate, and the like. In a preferred embodiment, the zinc (II) salt or hydrate is $Zn(NO_3)_2.6H_2O$.

In a preferred embodiment, the zinc (II) salt or hydrate is the limiting reagent in the process. In certain embodiments, an amount of the zinc (II) salt or hydrate is in a range of 0.01-100 mmol, preferably 0.1-20 mmol, preferably 0.15-10 mmol, preferably 0.175-5 mmol. In a preferred embodiment, the zinc (II) salt or hydrate is present at a concentration of 0.001-10 M in the solvent of the reaction mixture, preferably 0.01-5M, preferably 0.1-1 M in the solvent of the reaction mixture. In a preferred embodiment, the 1,3,5-benzenetricarboxylic acid may be present in an excess of 1.5-20 molar equivalents of the zinc (II) salt or hydrate, preferably 2-15 molar equivalents, preferably 4-12 molar equivalents, preferably 6-10 molar equivalents of the zinc (II) salt or hydrate.

In a preferred embodiment the reacting may be performed at a temperature of 25-140° C., preferably 40-120° C., preferably 45-110° C., preferably 50-100° C., preferably 60-95° C., preferably 70-90° C., or about 85° C. In a preferred embodiment, the reacting may be performed for a time period of 2-36 hours, preferably 4-30 hours, preferably 6-24 hours, preferably 8-20 hours, preferably 10-18 hours, preferably 12-16 hours. The zinc modified metal organic framework may be isolated and purified by methods known to those of ordinary skill in the art, such a filtration, decantation, aqueous work-up, extraction with organic solvents, distillation, crystallization, column chromatography, and high pressure liquid chromatography (HPLC) on normal phase or reversed phase.

In a preferred embodiment, the obtained zinc modified metal organic framework crystals are washed or rinsed with a polar aprotic solvent, preferably dimethylformamide 1-10 times, preferably 2-5 times, or about 3 times to obtain preferably colorless cubic crystals. In certain embodiments, the reacting may further comprise activating the zinc modified metal organic framework. As used herein, activation refers to removal of axial aqua ligands from a metal organic framework, the activation giving unsaturated metal sites without affecting the rigid framework of the metal organic framework. In a preferred embodiment, the zinc modified metal organic framework is activated by soaking in a polar protic solvent or non-polar solvent, preferably dichloromethane or methanol, most preferably methanol for 1-10 days, preferably 2-5 days, or about 3 days optionally with decanting and replenishment of fresh solvent. The obtained zinc modified metal organic framework may further be dried under preferably reduced pressure (i.e. vacuum) at a temperature of 50-300° C., preferably 100-250° C., preferably 125-200° C., preferably 150-180° C.

In another step of the process, at least a portion of the zinc modified metal organic framework is transmetallated by being immersed in a solution of a salt or hydrate of the second metal ions.

As used herein transmetallating or transmettalation refers to a type of organometallic reaction that involves the transfer of ligands from one metal to another. Generally the reaction is an irreversible process due to thermodynamic and kinetic reasons. Thermodynamics will favor the reaction based on the electronegativities of the metals and kinetics will favor the reaction if there are empty orbitals on both metals. In terms of the present disclosure, the transmetallation may be redox-transmetallation and/or redox-transmetallation/ligand exchange, preferably redox-transmetallation/ligand exchange.

In a preferred embodiment, the second metal ions are at least one selected from the group consisting of iron (II) ions, cobalt (II) ions, and copper (II) ions. Exemplary suitable salts or hydrates of the second metal ions include, but are not limited to, copper (II) bromide, copper (II) chloride, copper (II) chloride dihydrate, copper (II) cyclohexanbutyrate, copper (II) fluoride, copper (II) fluoride hydrate, copper (II) hydroxide, copper (II) hydroxide phosphate, copper (II) molybdate, copper (II) nitrate, copper (II) nitrate hemi (pentahydrate), copper (II) nitrate hydrate, copper (II) perchlorate, copper (II) pyrophosphate hydrate, copper (II) selenite dehydrate, copper (II) sulfate, copper (II) sulfate pentahydrate, copper (II) tartrate hydrate, copper (II) tetrafluoroborate hydrate, tetraamminecopper (II) sulfate monohydrate, ammonium cobalt (II) sulfate hexahydrate, cobalt (II) bromide, cobalt (II) carbonate hydrate, cobalt (II) chloride, cobalt (II) chloride hydrated, cobalt (II) cyanide dehydrate, cobalt (II) fluoride, cobalt (II) fluoride tetrahydrate, cobalt (II) hydroxide, cobalt (II) iodide, cobalt (II) nitrate hexahydrate, cobalt (II) oxalate dehydrate, cobalt (II) perchlorate hexahydrate, cobalt (II) phosphate hydrate, cobalt (II) sulfate heptahydrate, cobalt (II) sulfate hydrate, cobalt (II) tetrafluoroborate hexahydrate, cobalt (II) thiocyanate, ammonium iron (II) sulfate hexahydrate, iron (II) bromide, iron (II) chloride, iron (II) chloride tetrahydrate, iron (II) fluoride, iron (II) iodide, iron (II) molybdate, iron (II) oxalate dehydrate, iron (II) perchlorate hydrate, iron (II) sulfate hydrate, iron (II) tetrafluoroborate hexahydrate, potassium hexacyanoferrate (II) trihydrate, and the like. In a preferred embodiment, the salt or hydrate of the second metal ions is at least one selected from the group consisting of $Cu(NO_3)_2.3H_2O$, $Co(NO_3)_2.6H_2O$, and $FeCl_2.6H_2O$.

In a preferred embodiment, the zinc modified metal organic framework is the limiting reagent and is immersed in a 0.01-10 M solution of a salt or hydrate of the second metal ions, preferably 0.05-5.0 M, preferably 0.1-1.0 M, preferably 0.25-0.75 M solution of a salt or hydrate of the second metal ions. In a preferred embodiment the immersion is performed at a temperature of 10-100° C., preferably 20-80° C., preferably 25-70° C., preferably 30-60° C., preferably 35-50° C., or about 40° C. In a preferred embodiment the immersion is performed for a time period of 1-120 hours, preferably 12-96 hours, preferably 24-84 hours, preferably 36-78 hours, preferably 48-72 hours. In a preferred embodiment, the solution of a salt or hydrate of the second metal ions comprises a polar protic solvent or non-polar solvent, preferably dichloromethane or methanol, most preferably methanol as a solvent. The thereby obtained metal organic framework catalyst may be isolated and purified by methods known to those of ordinary skill in the art, such a filtration, decantation, aqueous work-up, extraction with organic solvents, distillation, crystallization, column chromatography, and high pressure liquid chromatography (HPLC) on normal phase or reversed phase.

In a preferred embodiment, the obtained metal organic framework catalyst crystals are washed or rinsed with a polar protic solvent, preferably methanol. In certain embodiments, the transmetallating may further comprise activating the metal organic framework catalyst. In a preferred embodiment, the metal organic framework catalyst is activated or washed tor remove any residual metal ions by soaking in a polar protic solvent or non-polar solvent, preferably dichloromethane or methanol, most preferably methanol. The obtained cation-exchanged metal organic framework may further be dried under preferably reduced pressure (i.e. vacuum) at a temperature of 10-100° C., preferably 15-80° C., preferably 20-60° C., preferably 25-40° C.

According to a third aspect, the present disclosure relates to a method for an oxidation of a cyclic hydrocarbon comprising contacting the cyclic hydrocarbon with the metal organic framework catalyst of the present disclosure in any of its embodiments in the presence of a solvent and an oxidizing agent to form an oxidized cyclic hydrocarbon.

As used herein, oxidation refers to the loss of electrons or the increase in oxidation state by a molecule, atom, or ion (i.e. the cyclic hydrocarbon). Redox (short for reduction-oxidation reaction) is a chemical reaction in which the oxidation states of atoms are changed. Any such reaction involves both a reduction process and a complimentary oxidation process, two key concepts involved with electron transfer processes. Redox reactions include all chemical reactions in which atoms have their oxidation state changed; in general, redox reactions involve the transfer of electrons between chemical species. The chemical species from which the electron is stripped is said to have been oxidized, while the chemical species to which the electron is added is said to have been reduced. The processes of oxidation and reduction occur simultaneously and cannot happen independently of one another. Although oxidation and reduction properly refer to change in oxidation state, the actual transfer of electrons may not actually occur. The oxidation state of an atom refers to the fictitious change that an atom would have if all bonds between atoms of different elements were 100% ionic. Thus, oxidation can best be defined as an increase in oxidation, and reduction as a decrease in oxidation state. In practice, the transfer of electrons will always cause a change in oxidation state; however, many reactions may be classified as redox even though no electron transfer occurs (i.e. those involving covalent bonds). As used herein, catalytic oxidations are processes that oxidize compounds using catalysts.

In terms of the present disclosure, the oxidations may be classified into groups depending on the type of bond change involved. These groups may include, but are not limited to, eliminations of hydrogen, reactions involving cleavage of carbon-carbon bonds, reaction involving replacement of hydrogen by oxygen, reactions in which oxygen is added to the substrate, and oxidative coupling, preferably reactions involving replacement of hydrogen by oxygen. In inorganic chemistry, where ionic bonds are common, an oxidation may be defined as the loss of one or more electrons by an atom. In organic chemistry, however, where polar covalent bonds are common, an oxidation is a reaction that results in a loss of electron density by carbon. This loss is usually caused either by bond formation between carbon and a more electronegative atom (usually oxygen, nitrogen, or a halogen) or by bond breaking between carbon and a less electronegative atom (usually hydrogen). Thus, oxidation refers to a decrease of electron density of carbon by forming for example C—O, C—N, and/or C—X bonds or breaking C—H bonds.

The practice in organic chemistry is to designate a series of functional groups, in a qualitative way, arranged in order of increasing oxidation state, and then to define an oxidation as a conversion of a functional group in a molecule from one category to another. Alkanes are at the lowest oxidation level in that they have the maximum possible number of C—H bonds, and $CO_2$ is at the highest level because it has the maximum possible number of C—O bonds. As used herein, any reaction that converts a compound from a lower level to a higher level is an oxidation. It is noted that this classification applies generally to only a single carbon atom or two adjacent carbon atoms. For example, $CH_3CH_3$ or RH can be thought to have a low oxidation state (~−4), $H_2C{=}CH_2$ or —C=C—, $CH_3OH$ or ROH, $CH_3Cl$ or RCl, and $CH_3NH_2$ or $RNH_2$ can be thought to have an increased oxidation state (~−2), HC≡CH or —C≡C—, $H_2C{=}O$ or $R_1R_2C{=}O$, $CH_2Cl_2$ or $R_1R_2CCl_2$, $H_2C{=}NH$, and HO—C—C—OH can be thought to have a further increased oxidation state (~0), $HCO_2H$ or RCOOH, $CHCl_3$ or $CRCl_3$, HC≡N or RC≡N and $RCONH_2$ can be thought to have an even further increased oxidation state (~+2), and $CO_2$ and $CCl_4$ can be though to have a highest oxidation state (~+4). As used herein, oxidation refers to loss of bonds to a hydrogen atom and/or gain of bonds to a more electronegative element such as oxygen, nitrogen, and/or the halogens, preferably oxygen. In a preferred embodiment, the oxidation is a transition of a $CH_3$ group to a HC=O or COOH group, or a $CH_2$ group to a HC—OH or CO=group, or a CH group to a C—OH group.

As used herein, a hydrocarbon is an organic compound consisting entirely of hydrogen and carbon and which are thus group 14 hydrides. Hydrocarbons from which one hydrogen atom has been removed are functional groups referred to as hydrocarbyls. Aromatic hydrocarbons (arenes), alkanes, alkenes, cycloalkanes and alkyne-based compounds are different types of hydrocarbons. As used herein a cyclic compound (ring compound) is a term for a compound in the field of chemistry in which one or more series of atoms in the compound is connected to form a ring. Rings may vary in size from three to many atoms, and preferably refer to examples where all the ring atoms are carbon (i.e. are carbocycles). Depending on the ring size, the bond order of the individual links between ring atoms, and their arrangement within the rings the cyclic hydrocarbon may be aromatic or aliphatic (non-aromatic). In terms of the present disclosure, the cyclic hydrocarbon may be aromatic or aliphatic.

In certain embodiments, the cyclic hydrocarbon is an alicyclic compound or carbocycle. As used herein an alicyclic compound is an organic compound that is both aliphatic and cyclic. They may contain one or more all-carbon rings which may be either saturated or unsaturated, but do not have aromatic character. Alicyclic compounds may have one or more aliphatic side chains attached, such as for example, methylcyclohexane. In certain embodiments, the cyclic hydrocarbon may be a simple alicyclic compound such as a monocyclic cycloalkane. Exemplary suitable monocyclic cycloalkanes include, but are not limited to, cyclopropane, cyclobutane, cyclopentane, cyclohexane, cycloheptane, cyclooctane, cyclotridecane, and the like, preferably cyclohexane. In certain embodiments, the cyclic hydrocarbon may be a bicyclic or polycyclic alkane. Exemplary bicyclic or polycyclic alkanes include, but are not limited to, bicycloundecane, norbornane, decalin, cubane, basketane, housane, and the like. In certain embodiments, the cyclic hydrocarbon may be a spiro compound. As used herein, spiro compounds have two or more rings that are connected through only one carbon atom. In certain embodiments, the cyclic hydrocarbon may be a monocyclic cycloalkene (cycloolefin) or bicyclic cycloalkene. Exemplary monocyclic or bicyclic cycloalkenes include, but are not limited to, cyclopropene, cyclobutene, cyclopentene, cyclohexene, cycloheptene, cyclooctene, 1,3-cyclohexadiene, 1,4-cyclohexadiene, 1,5-cyclooctadiene, norbornene, norbornadiene, methylenecyclohexane, 1-methylcyclohexene, and the like. In certain embodiments, the cyclic hydrocarbon may comprise one or more exocyclic double bonds, such as for example, the isotoluenes.

In certain embodiments, the cyclic hydrocarbon is an aromatic hydrocarbon or arene. As used herein, an aromatic hydrocarbon or arene is a hydrocarbon with sigma bonds and delocalized pi electrons between carbon atoms forming a circle. In contrast, aliphatic hydrocarbons lack this delocalization. The configuration of six carbon atoms in aromatic compounds is known as a benzene ring, after the simplest possible such hydrocarbon, benzene. In terms of the present disclosure, the aromatic hydrocarbon may be monocyclic (MAH) or polycyclic (PAH). In certain embodiments, the cyclic hydrocarbon is benzene or a benzene derivative. As used herein, benzene derivatives refer to from one to six substituents attached to a central benzene core. Exemplary suitable benzene derivatives include, but are not limited to, toluene, ethylbenzene, o-xylene, m-xylene, p-xylene, mixed xylenes, mesitylene, durene, 2-phenylhexane, biphenyl, and the like, preferably toluene.

In certain embodiments, the cyclic hydrocarbon is a polycyclic aromatic hydrocarbon (PAH). As used herein a polycyclic aromatic hydrocarbon is an aromatic hydrocarbon that consists of fused aromatic rings and does not contain heteroatoms or carry substituents. Exemplary suitable polycyclic hydrocarbons include, but are not limited to, naphthalene, naphthenes, anthracene, phenathrene, tetracene, chrysene, triphenylene, pyrene, pentacene, benzo[a]pyrene, corannulene, benzo[g,h,i]perylene, coronene, ovalene, benzo[c]fluorene, acenaphthene, acenaphthylene, benzo[a]anthracene, benzo[b]fluoranthene, benzo[j]fluoranthene, benzo[k]fluoranthene, benzo[e]pyrene, cyclopenta[c,d]pyrene, dibenz[a,h]anthracene, dibenzo[a,e]pyrene, dibenzo[a,h]pyrene, dibenzo[a,i]pyrene, dibenzo[a,l]pyrene, fluoroanthene, fluorene, indeno[1,2,3-c,d]pyrene, 5-methylchrysene and the like.

It is equally envisaged that the method of the present disclosure may be adapted to additional optionally substituted alkyl, cycloalkyl, aryl, or heterocyclic substrates or similar moieties of larger and/or more complex compounds.

As used herein, the term "substituted" refers to at least one hydrogen atom that is replaced with a non-hydrogen group, provided that normal valencies are maintained and that the substitution results in a stable compound. When a compound or substituent (-R group denoted as $R_1$, $R_2$, $R_3$ and so forth) is noted as "optionally substituted", the substituents are selected from the exemplary group including, but not limited to, halo, hydroxyl, alkoxy, oxo, alkanoyl, aryloxy, alkanoyloxy, amino, alkylamino, arylamino, arylalkylamino, disubstituted amines (e.g. in which the two amino substituents are selected from the exemplary group including, but not limited to, alkyl, aryl or arylalkyl), alkanylamino, aroylamino, aralkanoylamino, substituted alkanoylamino, substituted arylamino, substituted aralkanoylamino, thiol, alkylthio, arylthio, arylalkylthio, alkylthiono, arylthiono, aryalkylthiono, alkylsulfonyl, arylsulfonyl, arylalkylsulfonyl, sulfonamide (e.g. —SO$_2$NH$_2$), substituted sulfonamide, nitro, cyano, carboxy, carbamyl (e.g. —CONH$_2$), substituted carbamyl (e.g. —CONHalkyl, —CONHaryl, —CONHarylalkyl or cases where there are two substituents on one nitrogen from alkyl, aryl, or alkylalkyl), alkoxycarbonyl, aryl, substituted aryl, guanidine, heterocyclyl (e.g. indolyl, imidazoyl, furyl, thienyl, thiazolyl, pyrrolidyl, pyridyl, pyrimidiyl, pyrrolidinyl, piperidinyl, morpholinyl, piperazinyl, homopiperazinyl and the like), substituted heterocyclyl and mixtures thereof and the like. The substituted moiety may be either protected or unprotected as necessary, and as known to those skilled in the art.

As used herein, the term "alkyl" unless otherwise specified refers to both branched and straight chain saturated aliphatic primary, secondary, and/or tertiary hydrocarbons or hydrocarbon fragments of typically $C_1$ to $C_{10}$, and specifically includes, but is not limited to, methyl, trifluoromethyl, ethyl, propyl, isopropyl, cyclopropyl, butyl, isobutyl, t-butyl, pentyl, cyclopentyl, isopentyl, neopentyl, hexyl, isohexyl, cyclohexyl, cyclohexylmethyl, 3-methylpentyl, 2,2-dimethylbutyl, and 2,3-dimethylbutyl. As used herein, the term optionally includes substituted alkyl groups. Exemplary moieties with which the alkyl group can be substituted may be selected from the group including, but not limited to, hydroxyl, amino, alkylamino, arylamino, alkoxy, aryloxy, nitro, cyano, sulfonic acid, sulfate, phosphonic acid, phosphate, or phosphonate or mixtures thereof The substituted moiety may be either protected or unprotected as necessary, and as known to those skilled in the art.

As used herein, the term "cycloalkyl" refers to cyclized alkyl groups. Exemplary cycloalkyl groups include, but are not limited to, cyclopropyl, cyclobutyl, cyclopentyl, cyclohexyl, norbornyl, and adamantyl. Branched cycloalkyl groups such as exemplary 1-methylcyclopropyl and 2-methylcyclopropyl groups are included in the definition of cycloalkyl as used in the present disclosure.

As used herein, the term "aryl" unless otherwise specified refers to functional groups or substituents derived from an aromatic ring including, but not limited to, phenyl, biphenyl, napthyl, thienyl, and indolyl. As used herein, the term optionally includes both substituted and unsubstituted moieties. Exemplary moieties with which the aryl group can be substituted may be selected from the group including, but not limited to, hydroxyl, amino, alkylamino, arylamino, alkoxy, aryloxy, nitro, cyano, sulfonic acid, sulfate, phosphonic acid, phosphate or phosphonate or mixtures thereof The substituted moiety may be either protected or unprotected as necessary, and as known to those skilled in the art.

As used herein, the term "heterocyclyl" unless otherwise specified refers to a 3-8, preferably 4-8, more preferably 4-7 membered monocyclic ring or a fused 8-12 membered bicyclic ring which may be saturated or partially unsaturated, which monocyclic or bicyclic ring contains 1 to 4 heteroatoms selected from oxygen, nitrogen, silicon or sulfur. Examples of such monocyclic rings include oxaziridinyl, homopiperazinyl, oxiranyl, dioxiranyl, aziridinyl, pyrrolidinyl, azetidinyl, pyrazolidinyl, oxazolidinyl, piperidinyl, piperazinyl, morpholinyl, thiomorpholinyl, thiazolidinyl, hydantoinyl, valerolactamyl, oxiranyl, oxetanyl, dioxolanyl, dioxanyl, oxathiolanyl, oxathianyl, dithianyl, dihydrofuranyl, tetrahydrofuranyl, dihydropyranyl, tetrahydropyranyl, tetrahydropyridyl, tetrahydropyrimidinyl, tetrahydrothiophenyl, tetrahydrothiopyranyl, diazepanyl and azepanyl. Examples of such bicyclic rings include indolinyl, isoindolinyl, benzopyranyl, quinuclidinyl, 2,3,4,5-tetrahydro-1,3,benzazepine, 4-(benzo-1,3,dioxol-5-methyl)piperazine, and tetrahydroisoquinolinyl. Further, "substituted heterocyclyl" may refer to a heterocyclyl ring which has one or more oxygen atoms bonded to the ring (i.e. as ring atoms). Preferably, said atom which is bonded to the ring selected from nitrogen or sulphur. An example of a heterocyclyl substituted with one or more oxygen atoms is 1,1-dioxido-1,3-thiazolidinyl.

The general nature of the cyclic hydrocarbon substrate is not viewed as particularly limiting to the oxidation process described herein in any of its embodiments. In a preferred embodiment, the cyclic hydrocarbon is at least one selected from the group consisting of toluene, cyclohexane, and methylcyclohexane.

As used herein, an oxidizing agent (oxidant, oxidizer) refers to a substance that has the ability to oxidize other substances (i.e. cause them to lose electrons). Substances that have the ability to oxidize other substances (cause them to lose electrons) are said to be oxidative or oxidizing and are known as oxidizing agents, oxidants, or oxidizers. That is, the oxidant (oxidizing agent) removes electrons from another substance, and is thus itself reduced. Because it "accepts" electrons, the oxidizing agent may also be called an electron acceptor. Oxygen is a quintessential oxidizer. Common oxidizing agents include, but are not limited to, oxygen, hydrogen peroxide, and the halogens. Oxidants are usually chemical substances with elements in high oxidation states (e.g. $H_2O_2$, $MnO_4^-$, $CrO_3$, $Cr_2O_7^{2-}$, $OsO_4$) or else highly electronegative elements ($O_2$, $F_2$, $Cl_2$, $Br_2$) that can gain extra electrons by oxidizing another substance. In one sense, an oxidizing agent is a chemical species that undergoes a chemical reaction that removes one or more electrons from another atom. In that sense, it is one component in an oxidation-reduction (redox) reaction. In another sense, an oxidizing agent is a chemical species that transfers electronegative atoms, usually oxygen, to a substrate. Combustion, many explosives, and organic redox reactions typically involve atom-transfer reactions.

In certain embodiments, the oxidizing agent may be an electron acceptor. Electron acceptors participate in electron-transfer reactions. In this context, the oxidizing agent is called an electron acceptor and the reducing agent is called an electron donor. Extensive tabulations and rankings of the electron accepting properties of various reagents (redox potentials) are available. The mechanism and details of the electron transfer event can be described as inner sphere or outer sphere. Exemplary electron acceptor oxidizing agents include, but are not limited to, tetracyanoquinodimethane, the ferrocenium ion $Fe(C_5H_5)^{2+}$, which accepts an electron to form $Fe(C_5H_5)_2$, the radical cation derived from $N(C_6H_4$—$4$—$Br)_3$ ("Magic blue"), and the like.

In a preferred embodiment, the oxidizing agent is an atom-transfer reagent. Commonly, an oxidizing agent as an atom-transfer reagent transfers oxygen atoms to a substrate. In this context, the oxidizing agent can be termed an oxygenation reagent or an oxygen-atom transfer (OAT) agent. Exemplary oxygen-atom transfer agents include, but are not limited to, $MnO^{4-}$ (permanganate), $CrO_4^{2-}$ (chromate), $OsO_4$ (osmium tetroxide), and $ClO^{4-}$ (perchlorate). In some instances, these oxide species can also serve as electron acceptors, as illustrated by the conversion of $MnO_4^-$ to $MnO_4^{2-}$, manganite. In a preferred embodiment, the oxidizing agent is an oxygen-atom transfer agent. Exemplary suitable oxygen-atom transfer agent oxidizing agents include, but are not limited to, oxygen ($O_2$), ozone ($O_3$), hydrogen peroxide ($H_2O_2$), tent-butyl hydroperoxide (TBHP) and other inorganic peroxides, Fenton's reagent, fluorine ($F_2$), chlorine ($Cl_2$), bromine ($Br_2$), iodine ($I_2$) and other halogens, nitric acid ($HNO_3$) and nitrate compounds, sulfuric acid ($H_2SO_4$), peroxydisulfuric acid ($H_2S_2O_8$), peroxymonosulfuric acid ($H_2SO_5$), chlorite, chlorate ($ClO_3^-$), perchlorate and other analogous halogen compounds, hypochlorite ($ClO^-$) and other hypohalite compounds, sodium hypochlorite (NaClO) hexavalent chromium compounds (i.e. chromic and dichromic acids and chromium trioxide ($CrO_3$), pyridinium chlorochromate (PCC) and chromate/dichromate ($CrO_4^{2-}/Cr_2O_7^{2-}$) compounds), permanganate compounds (i.e. potassium permanganate), sodium perborate, nitrous oxide ($N_2O$), potassium nitrate ($KNO_3$), sodium bismuthate, sulfur dioxide ($SO_2$), and the like. In a most preferred embodiment, the oxidizing agent is hydrogen peroxide.

In a preferred embodiment, the contacting and reacting is performed in a polar aprotic solvent. Exemplary suitable polar aprotic solvents include, but are not limited to, tetrahydrofuran, ethyl acetate, acetone, dimethylformamide, acetonitrile, dimethyl sulfoxide, nitromethane, propylene carbonate and mixtures thereof, preferably the solvent is acetonitrile or dimethylformamide, most preferably the solvent is acetonitrile. It is equally envisaged that the present method may be adapted to incorporate polar protic solvents including, but not limited to, formic acid, n-butanol, isopropanol, n-propanol, ethanol, methanol, acetic acid, and water, as well as non-polar solvents including, but not limited to, pentane, cyclopentane, hexane, cyclohexane, benzene, toluene, 1,4-dioxane, chloroform, diethyl ether, dichloromethane, and mixtures thereof.

In a preferred embodiment, the cyclic hydrocarbon is the limiting reagent in the oxidation method. In certain embodiments, an amount of the cyclic hydrocarbon may be in a range of 0.1-100 mmol, preferably 0.5-25 mmol, preferably 1.0-10 mmol, preferably 1.0-5 mmol. In a preferred embodiment, the cyclic hydrocarbon is present at a concentration of 0.01-20 M in the solvent of the reaction mixture, preferably 0.1-10 M, preferably 1.0-5.0 M in the solvent of the reaction mixture. In a preferred embodiment, the oxidizing agent may be present in an excess of 1.1-50 molar equivalents of the cyclic hydrocarbon, preferably 2-40 molar equivalents, preferably 4-30 molar equivalents, preferably 5-20 molar equivalents of the cyclic hydrocarbon.

In a preferred embodiment, an amount of the metal organic framework catalyst may range from 1-200 grams of catalyst per mole of the cyclic hydrocarbon, preferably 5-150 g/mol, preferably 10-100 g/mol, preferably 15-80 g/mol, preferably 20-75 grams of catalyst per mole of the cyclic hydrocarbon. In certain embodiments, the amount of the metal organic framework catalyst may range from 0.001-10 mol % of a number of moles of the cyclic hydrocarbon, preferably 0.05-5 mol %, preferably 0.01-2 mol %, preferably 0.1-1.0 mol % of a number of moles of the cyclic hydrocarbon, although higher catalyst loadings (e.g. up to 20 mol %, 30 mol %, 40 mol %, 80 mol %) may be used and the method will still proceed as intended. In certain embodiments, the molar ratio of the cyclic hydrocarbon to the metal organic framework catalyst is greater than 100, preferably greater than 200, preferably greater than 400, preferably greater than 500.

In a preferred embodiment, the contacting may be performed at a temperature in the range of 40-100° C., preferably 45-95° C., preferably 50-90° C., preferably 55-85° C., preferably 60-80° C., preferably 65-75° C., or about 70° C. An external heat source, such as a water bath or an oil bath, an oven, microwave, or a heating mantle, may be employed to heat the reaction mixture. In a preferred embodiment, the external heat source is a thermostatted thermocirculator. In one embodiment, the aqueous solution is not heated with microwave irradiation. Preferably, the reacting is performed under air, preferably in a sealed container. In another embodiment, the reacting and contacting is performed in an inert atmosphere provided by an inert gas (i.e. nitrogen and/or argon).

In a preferred embodiment, the contacting and reacting may be performed for a time period of 2-36 hours, preferably 4-30 hours, preferably 6-24 hours, preferably 8-20 hours, preferably 10-18 hours, preferably 12-16 hours. The reaction may be shaken/stirred throughout the duration of the contacting and reacting by employing a rotary shaker, a magnetic stirrer, or an overhead stirrer. In another embodiment, the reaction mixture is left to stand (i.e. not stirred). In one embodiment, the reaction mixture is preferably mixed in a centrifugal mixer with a rotational speed of at least 200 rpm, preferably at least 500 rpm, preferably at least 800 rpm, preferably at least 1000 rpm, even though it may also be mixed with a spatula. In one embodiment, the reaction mixture is sonicated during the mixing.

The reaction mixture is preferably heterogeneous and comprises suspended metal organic framework catalyst particles in the liquid reaction mixture. In certain embodiments, the metal organic framework catalyst particles may be dispersed within the reaction mixture, and may further be filtered, washed, reactivated, and/or recycled at the end of a reaction iteration. In one embodiment, the metal organic framework catalyst may be placed in a bag or semi-permeable membrane and the bag may be immersed in the reaction mixture. Accordingly, the metal organic framework catalyst remains in the bag or semi-permeable membrane through the contacting and reaction until the oxidation is completed. Preferably, the membrane that is required for this technique shall allow easy transportation of both reactants and products yet have a pore size that ensures retention of the metal organic framework catalyst. In certain embodiments, the progress of each reaction iteration may be monitored by methods well known to those of ordinary skill in the art including, but not limited to, thin layer chromatography, gas chromatography, nuclear magnetic resonance, infrared spectroscopy, and high pressure liquid chromatography combined with ultraviolet detection or mass spectroscopy The general nature of the cyclic hydrocarbon substrate is not viewed as particularly limiting to the oxidation process described herein in any of its embodiments. In a preferred embodiment, the cyclic hydrocarbon is at least one selected from the group consisting of toluene, cyclohexane, and methylcyclohexane. In certain embodiments, the cyclic hydrocarbon is toluene and the formed oxidized cyclic hydrocarbon is at least one selected from the group consisting of benzaldehyde, benzoic acid, benzyl alcohol, and cresols (defined as mixed cresols or o,m,p-cresols including o-cresol, m-cresol, and p-cresol), preferably benzaldehyde. In certain embodiments, the cyclic hydrocarbon is cyclohexane and the formed oxidized cyclic hydrocarbon is at least one selected from the group consisting of cyclohexanone, cyclohexanol, 4-hydroxycyclohexanone, and 1,4-cyclohexadione, preferably cyclohexanone. In certain embodiments the cyclic hydrocarbon is methylcyclohexane and the formed oxidized cyclic hydrocarbon is at least one selected from the group consisting of methylcyclohexanol (defined as including 1-methylcyclohexan-1-ol, 2-methylcyclohexan-1-ol, 3-methylcyclohexan-1-ol, and 4-methylcyclohexan-1-ol), methylcyclohexanone (defined as including 2-methylcyclohexan-1-one, 3-methylcyclohexan-1-one, and 4-methylcyclohexan-1-one), cyclohexanemethanol, cyclohexanal, and 3-hepten-2-one, preferably methylcyclohexanol or methylcyclohexanone.

The definitions used in calculating the conversion and selectivity of the cyclic hydrocarbon to one or more oxidized cyclic hydrocarbons are represented for the method of the present disclosure using the metal organic framework catalyst in any of its embodiments are represented in formula (I) and formula (II) respectively.

$$\text{Conversion of cyclic hydrocarbon} = \frac{\text{Moles of cyclic hydrocarbon converted}}{\text{Moles of cyclic hydrocarbon fed}} \times 100\% \quad (I)$$

$$\text{Selectivity to oxidized product } i = \frac{\text{Moles of oxidized product } i}{\text{Moles of cyclic hydrocarbon converted}} \times 100\% \quad (II)$$

The conversion of cyclic hydrocarbon (i.e. toluene) (%) can be thought of as moles of cyclic hydrocarbon converted divided by moles of cyclic hydrocarbon fed multiplied by 100% and the selectivity (i.e. benzaldehyde, benzoic acid, cresols) to oxidized cyclic hydrocarbon product can be thought of as moles of oxidized cyclic hydrocarbon product divided by the moles of cyclic hydrocarbon converted multiplied by 100%.

In a preferred embodiment, the percent conversion from the cyclic hydrocarbon to oxidized cyclic hydrocarbon products is greater than 15%, preferably greater than 20%, preferably greater than 25%, preferably greater than 30%, preferably greater than 35%, preferably greater than 40%, preferably greater than 50%, preferably greater than 60%, preferably greater than 70%. In a preferred embodiment, the method has a percent selectivity for a single desired oxidized cyclic hydrocarbon of greater than 10% relative to a total amount of oxidized cyclic hydrocarbon products, preferably greater 15%, preferably greater than 20%, preferably greater than 25%, preferably greater than 30%, preferably greater than 35%, preferably greater than 40%, preferably greater than 50%, preferably greater than 60%, preferably greater than 70% relative to a total amount of oxidized cyclic hydrocarbon products.

In a preferred embodiment, the cyclic hydrocarbon is toluene and 15-80% of the toluene is converted to the oxidized cyclic hydrocarbon, preferably 20-70%, preferably 25-60%, preferably 30-50%, preferably 35-45% of the toluene is converted to the oxidized cyclic hydrocarbon at a reaction time of greater than 6 hours, preferably greater than 8 hours, preferably greater than 10 hours, preferably greater than 12 hours, preferably greater than 16 hours, preferably greater than 20 hours, preferably greater than 24 hours.

In a preferred embodiment, the cyclic hydrocarbon is toluene and the method has a benzaldehyde selectivity relative to a total amount of oxidized cyclic hydrocarbon products in the range of 15-70% relative to a total amount of oxidation products, preferably 20-65%, preferably 30-60%, preferably 35-55% relative to a total amount of oxidation products. In a preferred embodiment, the cyclic hydrocarbon is toluene and the method has a benzoic acid selectivity relative to a total amount of oxidized cyclic hydrocarbon products of less than 20%, preferably less than 15%, preferably less than 12%, preferably less than 10%, preferably less than 8%, preferably less than 6%, preferably less than 4%, preferably less than 2%. In a preferred embodiment, the cyclic hydrocarbon is toluene and the method has a cresols selectivity relative to a total amount of oxidized cyclic hydrocarbon products of 30-80%, preferably 33-70%, preferably 35-65%.

In a preferred embodiment, the cyclic hydrocarbon is toluene and the second metal ions are copper (II) ions and the oxidation has the percent conversion from the cyclic hydrocarbon to oxidized cyclic hydrocarbon products of greater than 55%, preferably greater than 60%, preferably greater than 62%, preferably greater than 64%, preferably greater than 66%, preferably greater than 68%, preferably greater than 70%, preferably greater than 72%, preferably greater than 75%.

In a preferred embodiment, the cyclic hydrocarbon is toluene and the second metal ions are iron (II) ions and the oxidation has a benzaldehyde selectivity relative to a total amount of oxidized cyclic hydrocarbon products of greater than 55% relative to a total amount of oxidation products, preferably greater than 56%, preferably greater than 57%, preferably greater than 58%, preferably greater than 59%, preferably greater than 60%, preferably greater than 61%, preferably greater than 62%, preferably greater than 63%, preferably greater than 64%, preferably greater than 65%, preferably greater than 70%, preferably greater than 75% benzaldehyde selectivity relative to a total amount of oxidized cyclic hydrocarbon products. In a preferred embodiment, the cyclic hydrocarbon is toluene and the second metal ions are iron (II) ions and the oxidation has a cresols selectivity relative to a total amount of oxidized cyclic hydrocarbon products of less than 40%, preferably less than 38%, preferably less than 36%, preferably less than 34%, preferably less than 32%, preferably less than 30%.

In a preferred embodiment, the cyclic hydrocarbon is toluene and the method has a benzaldehyde selectivity relative to a total amount of oxidized cyclic hydrocarbon products greater than or equal to a benzaldehyde selectivity relative to a total amount of oxidized cyclic hydrocarbon products of a substantially similar method performed in a substantially similar method performed in a substantially similar manner with a substantially similar metal organic framework catalyst lacking the zinc (II) ions, the second metal ions or both. In a preferred embodiment, the cyclic hydrocarbon is toluene and the method has a benzaldehyde selectivity relative to a total amount of oxidized cyclic hydrocarbon products that is at least 5 percentage points greater, preferably at least 10 percentage points, preferably at least 15 percentage points, preferably at least 20 percentage points, preferably at least 25 percentage points, preferably at least 30 percentage points, preferably at least 35 percentage points, preferably at least 40 percentage points, preferably at least 45 percentage points, preferably at least 50 percentage points, preferably at least 55 percentage points, preferably at least 60 percentage points, preferably at least 65 percentage points greater than a benzaldehyde selectivity relative to a total amount of oxidized cyclic hydrocarbon products of a substantially similar method performed in a substantially similar method performed in a substantially similar manner with a substantially similar metal organic framework catalyst lacking the zinc (II) ions, the second metal ions or both.

In a preferred embodiment, the cyclic hydrocarbon is cyclohexane and 10-60% of the cyclohexane is converted to the oxidized cyclic hydrocarbon, preferably 12-50%, preferably 15-40%, preferably 18-35%, preferably 20-33% of the cyclohexane is converted to the oxidized cyclic hydrocarbon at a reaction time of greater than 6 hours, preferably greater than 8 hours, preferably greater than 10 hours, preferably greater than 12 hours, preferably greater than 16 hours, preferably greater than 20 hours, preferably greater than 24 hours.

In a preferred embodiment, the cyclic hydrocarbon is cyclohexane and the method has a cyclohexanone selectivity relative to a total amount of oxidized cyclic hydrocarbon products in the range of 45-80% relative to a total amount of oxidation products, preferably 48-75%, preferably 50-70%, preferably 55-65% relative to a total amount of oxidation products. In a preferred embodiment, the cyclic hydrocarbon is cyclohexanone and the method has a cyclohexanol selectivity relative to a total amount of oxidized cyclic hydrocarbon products of less than 50%, preferably less than 45%, preferably less than 40%, preferably less than 35%, preferably less than 30%, preferably less than 25%, preferably less than 20%. In a preferred embodiment, the cyclic hydrocarbon is cyclohexane and the method has a 4-hydroxy cyclohexanone selectivity relative to a total amount of oxidized cyclic hydrocarbon products and a 1,4-cyclohexadione selectivity relative to a total amount of oxidized cyclic hydrocarbon products of 1-25%, preferably 2-20%, preferably 5-15%.

In a preferred embodiment, the cyclic hydrocarbon is methylcyclohexane and 10-60% of the methylcyclohexane is converted to the oxidized cyclic hydrocarbon, preferably 12-50%, preferably 15-45%, preferably 20-40%, preferably 25-35% of the methylcyclohexane is converted to the oxidized cyclic hydrocarbon at a reaction time of greater than 6 hours, preferably greater than 8 hours, preferably greater than 10 hours, preferably greater than 12 hours, preferably greater than 16 hours, preferably greater than 20 hours, preferably greater than 24 hours.

In a preferred embodiment, the cyclic hydrocarbon is methylcyclohexane and the method has a methylcyclohexanone selectivity relative to a total amount of oxidized cyclic hydrocarbon products in the range of 15-60% relative to a total amount of oxidation products, preferably 20-50%, preferably 30-45%, preferably 35-40% relative to a total amount of oxidation products. In a preferred embodiment, the cyclic hydrocarbon is methylcyclohexanone and the method has a methylcyclohexanol selectivity relative to a total amount of oxidized cyclic hydrocarbon products of greater than 30%, preferably greater than 35%, preferably greater than 40%, preferably greater than 45%, preferably greater than 50%, preferably greater than 55%, preferably greater than 60%, preferably greater than 65%, preferably greater than 70%. In a preferred embodiment, the cyclic hydrocarbon is methylcyclohexane and the method has a cyclohexanone methanol selectivity relative to a total amount of oxidized cyclic hydrocarbon products and a cyclohexanal selectivity relative to a total amount of oxidized cyclic hydrocarbon products of 1-20%, preferably 2-15%, preferably 5-10%.

In a preferred embodiment, the cyclic hydrocarbon is at least one selected from the group consisting of cyclohexane and methylcyclohexane and 10-60% of the cyclic hydrocarbon is converted to the oxidized cyclic hydrocarbon, preferably 12-50%, preferably 15-48%, preferably 20-45%, preferably 25-40% of the cyclic hydrocarbon is converted to the oxidized cyclic hydrocarbon at a reaction time of greater than 12 hours, preferably greater than 16 hours, preferably greater than 20 hours, preferably greater than 24 hours.

In a preferred embodiment, the method further comprises recovering and reusing the metal organic framework catalyst of the present disclosure in any of its embodiments in at least 2 reaction iterations with a less than 20 percentage point decrease in conversion, a less than 20 percentage point decrease in selectivity or both. In this manner the metal organic framework catalyst can be recovered and reused in at least 2 reaction iterations, preferably at least 3, preferably at least 4, preferably at least 5, preferably at least 6, preferably at least 8, preferably at least 10, preferably at least 15, preferably at least 20, preferably at least 30, preferably at least 50 reaction iterations.

In certain embodiments, the metal organic framework catalyst may be separated by removing the bag containing the metal organic framework catalyst, dialysis in a solvent, or using a micro-filter or a paper filter. The phrase recovering, reusing, and/or recycling the metal organic framework catalyst refers to a process whereby the metal organic framework catalyst is first washed by an organic solvent, reactivated, dried and then added to a new batch of reactants (either the same or a different type of cyclic hydrocarbon substrate). Preferred organic solvents for washing and/or reactivating the metal organic framework catalyst include, without limitation, methanol, acetone, ethanol, tetrahydrofuran, acetonitrile, dichloromethane, ether, glycol ether, acetamide, dimethyl acetamide, dimethyl sulfoxide, or combinations thereof. The metal organic framework catalyst may be dried in vacuum and/or with heating, for example, the metal organic framework catalyst may be dried in a vacuum oven. The dried metal organic framework catalyst may be optionally stored prior to an additional reaction iteration.

In a preferred embodiment, there is a less than 20 percentage point change in percent cyclic hydrocarbon (i.e. toluene, cyclohexane, methylcyclohexane) conversion between the first and second reaction iteration, preferably less than 15 percentage points, preferably less than 10 percentage points, preferably less than 5 percentage points, preferably less than 4 percentage points, preferably less than 3 percentage points, preferably less than 2 percentage points, preferably a less than 1 percentage point change in percent cyclic hydrocarbon (i.e. toluene, cyclohexane, methylcyclohexane) conversion between the first and second reaction iteration. In certain embodiments, there is a less than 20 percentage point change in percent cyclic hydrocarbon (i.e. toluene, cyclohexane, methylcyclohexane) conversion, preferably less than 15 percentage points, preferably less than 10 percentage points, preferably less than 5 percentage points, preferably less than a 2 percentage point change in percent cyclic hydrocarbon (i.e. toluene, cyclohexane, methylcyclohexane) conversion between the first and twentieth reaction iteration, preferably between the first and fifteenth reaction iteration, preferably between the first and tenth reaction iteration, preferably between the first and fifth reaction iteration, preferably between the first and fourth reaction iteration, preferably between, the first and third reaction iteration, preferably between the first and second reaction iteration.

In a preferred embodiment, there is a less than 20 percentage point change in percent single oxidized cyclic hydrocarbon product (i.e. benzaldehyde from toluene, cyclohexanone or cyclohexanol from cyclohexane, methylcyclohexanol or methyl cyclohexanone from methylcyclohexane) selectivity relative to a total amount of oxidized cyclic hydrocarbon products between the first and second reaction iteration, preferably less than 15 percentage points, preferably less than 10 percentage points, preferably less than 5 percentage points, preferably less than 4 percentage points, preferably less than 3 percentage points, preferably less than 2 percentage points, preferably a less than 1 percentage point change in percent single oxidized cyclic hydrocarbon product (i.e. benzaldehyde from toluene, cyclohexanone or cyclohexanol from cyclohexane, methylcyclohexanol or methyl cyclohexanone from methylcyclohexane) selectivity relative to a total amount of oxidized cyclic hydrocarbon products between the first and second reaction iteration. In certain embodiments, there is a less than 20 percentage point change in percent single oxidized cyclic hydrocarbon product (i.e. benzaldehyde from toluene, cyclohexanone or cyclohexanol from cyclohexane, methylcyclohexanol or methyl cyclohexanone from methylcyclohexane) selectivity relative to a total amount of oxidized cyclic hydrocarbon products, preferably less than 15 percentage points, preferably less than 10 percentage points, preferably less than 5 percentage points, preferably less than a 2 percentage point change in percent single oxidized cyclic hydrocarbon product (i.e. benzaldehyde from toluene, cyclohexanone or cyclohexanol from cyclohexane, methylcyclohexanol or methyl cyclohexanone from methylcyclohexane) selectivity relative to a total amount of oxidized cyclic hydrocarbon products between the first and twentieth reaction iteration, preferably between the first and fifteenth reaction iteration, preferably between the first and tenth reaction iteration, preferably between the first and fifth reaction iteration, preferably between the first and fourth reaction iteration, preferably between, the first and third reaction iteration, preferably between the first and second reaction iteration.

It is equally envisaged, that the method of the present disclosure and/or the metal organic framework catalyst of the present disclosure in any of their embodiments may be adapted to provide catalysis in a wide variety of chemical transformations. Exemplary suitable chemical transformations include, but are not limited to, reduction of carbon-carbon multiple bonds, 1,3-dipolar cycloaddition, hydroxymethylation, cyanosilylation of aldehydes, Knoevenagel condensation, alkylation of aldehydes, oxidation of olefins, cycloaddition of $CO_2$ and epoxides, ring opening of epoxides (oxidation of hydrocarbons), Heck coupling, oxidation of sulfides, aerobic oxidation of olefins, methanolysis of epoxides, epoxidation of olefins, oxidative self-coupling, aldol condensttion reactions, Mukaiyama aldol reaction, cyclizations, oxidation of thioethers, transesterification, Friedel-Crafts alkylation, Suzuki-Miyaura coupling, hydrogenation of olefins, intermolecular transfer of acyl, isomerization, rearrangements, Henry reaction, Click reaction, cross-dehydrogenative coupling, alcohol oxidation, and the like. It is equally envisaged, that the method of the present disclosure and/or the metal organic framework catalyst of the present disclosure in any of their embodiments may be adapted to provide a means of gas separation, gas sensing, and gas storage, in particular $H_2$ storage.

The examples below are intended to further illustrate protocols for preparing and characterizing the metal organic frameworks of the present disclosure. Further, they are intended to illustrate assessing the properties and applications of these metal organic frameworks. They are not intended to limit the scope of the claims.

EXAMPLE 1

Chemicals and Materials

All reagents were used as purchased without further purification. 1,3,5-benzene tricarboxylic acid (BTC), $Cu(NO_3)_2 \cdot 3H_2O$, $Co(NO_3)_2 \cdot 6H_2O$, $Ni(NO_3)_2 \cdot 6H_2O$, $Zn(NO_3)_2 \cdot 6H_2O$, $FeCl_2 \cdot 6H_2O$, N,N-dimethylformamide (DMF) and ethanol were obtained from Sigma-Aldrich. Acetonitrile was obtained from Sigma-Aldrich. Toluene, cyclohexane and methylcyclohexane were used as purchased from Sigma-Aldrich. New 10 mL and 20 mL kimble scintillation vials were used for the synthesis of various metal organic frameworks (MOFs).

EXAMPLE 2

Synthesis of Metal Organic Frameworks (HKUST-1 and Zn-HKUST-1) and Transmetallation of Zn-HKUST-1

Figure 11:
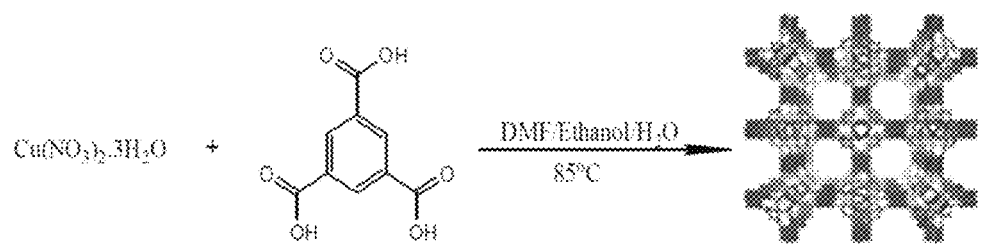
FIG. 11 is the general scheme and procedure for the synthesis of the prepared HKUST-1 metal organic framework from $Cu(NO_3)_2.3H_2O$ and 1,3,5-benzenetricarboxylic acid (BTC).

In a standard procedure, a mixture of $Cu(NO_3)_2.3H_2O$ (0.438 g, 1.81 mmol) and 1,3,5-benzenetricarboxylic acid (BTC) (0.236 g, 1.12 mmol) were completely dissolved in a solvent mixture containing N,N-dimethylformamide (2 mL), deionized water (2 mL) and ethanol (2 mL) in a tightly sealed 20 mL vial [Rowsell, J. L. C. & Yaghi, O. M *J. Am. Chem. Soc.*, 2006, 128, 1304-1315.—incorporated herein by reference in its entirety]. The tightly covered vial was placed in an isothermal oven at 85° C. for 20 hours to yield small, blue, octahedral crystals. After cooling the vial to room temperature, the mother liquor was decanted and the tiny crystals were rinsed with DMF three times. The crystals were then activated by soaking in 5 mL of dichloromethane (DCM) for 3 days at room temperature during which DCM was decanted and freshly replenished three times. The crystals were dried under vacuum at 160° C. for 4 hours yielding 0.3 g of HKUST-1 in the form of deep blue crystals. FIG. 11 is a typical schematic representation for the synthesis of HKUST-1.

Figure 12:
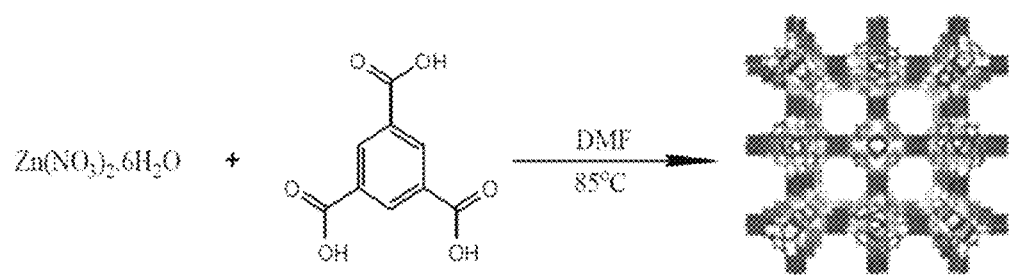
FIG. 12 is the general scheme and procedure for the synthesis of the prepared Zn-HKUST-1 metal organic framework from $Zn(NO_3)_2.6H_2O$ and 1,3,5-benzenetricarboxylic acid (BTC).

Using a modified procedure, a homogeneous mixture of $Zn(NO_3)_2.6H_2O$ (0.04 g, 0.188 mmol) and 1,3,5-benzenetricarboxylic acid (BTC) (0.171 g, 1.12 mmol) was dissolved in 10 mL N,N-dimethylformamide in a tightly sealed 20 mL scintillation vial [Bhunia, M. K, Hughes, J. T. Fettinger , J. C. and Navrotsky, A. *Langmuir* 2013, 29, 8140-8145.—incorporated herein by reference in its entirety]. The tightly covered vial was placed in an isothermal oven at 85° C. for 16 hours to form colorless cubic crystals. After cooling the vial to room temperature, the mother liquor was decanted and the tiny crystals were rinsed with DMF three times. The crystals were then activated by soaking in methanol for 3 days at room temperature during which methanol was decanted and freshly replenished three times. The crystals were dried under vacuum at 170° C. for 4 hours. FIG. 12 is a typical schematic representation for the synthesis of Zn-HKUST-1.

Pure samples of HKUST-1 and Zn-HKUST-1 metal organic frameworks (MOFs) were obtained as blue and colorless crystals, respectively. The crystals were dried under vacuum at 120° C. and stored in air tight vials to prevent moisture. The dried samples were characterized using Fourier transform infrared spectrophotometry (FT-IR), scanning electron microscopy (SEM) and powder X-ray diffraction (PXRD).

Portions of the as-synthesized Zn-HKUST-1 crystals were soaked in 0.5 M methanolic solutions of $Cu(NO_3)_2.3H_2O$, $Co(NO_3)_2.6H_2O$, and $FeCl_2.6H_2O$ for 72 hours at 40° C. At the end of the incubation, the remaining solution of metal ions were decanted, and the transmetallated crystals harvested by filtration. The crystals were washed thoroughly with methanol and then soaked in methanol for complete removal of residual metal ions. The resulting cation exchanged MOFs were dried under reduced pressure at room temperature.

EXAMPLE 3

Fourier Transform Infrared (FT-IR) Spectroscopy Analysis of Prepared Metal Organic Frameworks (MOFs)

Figure 13:
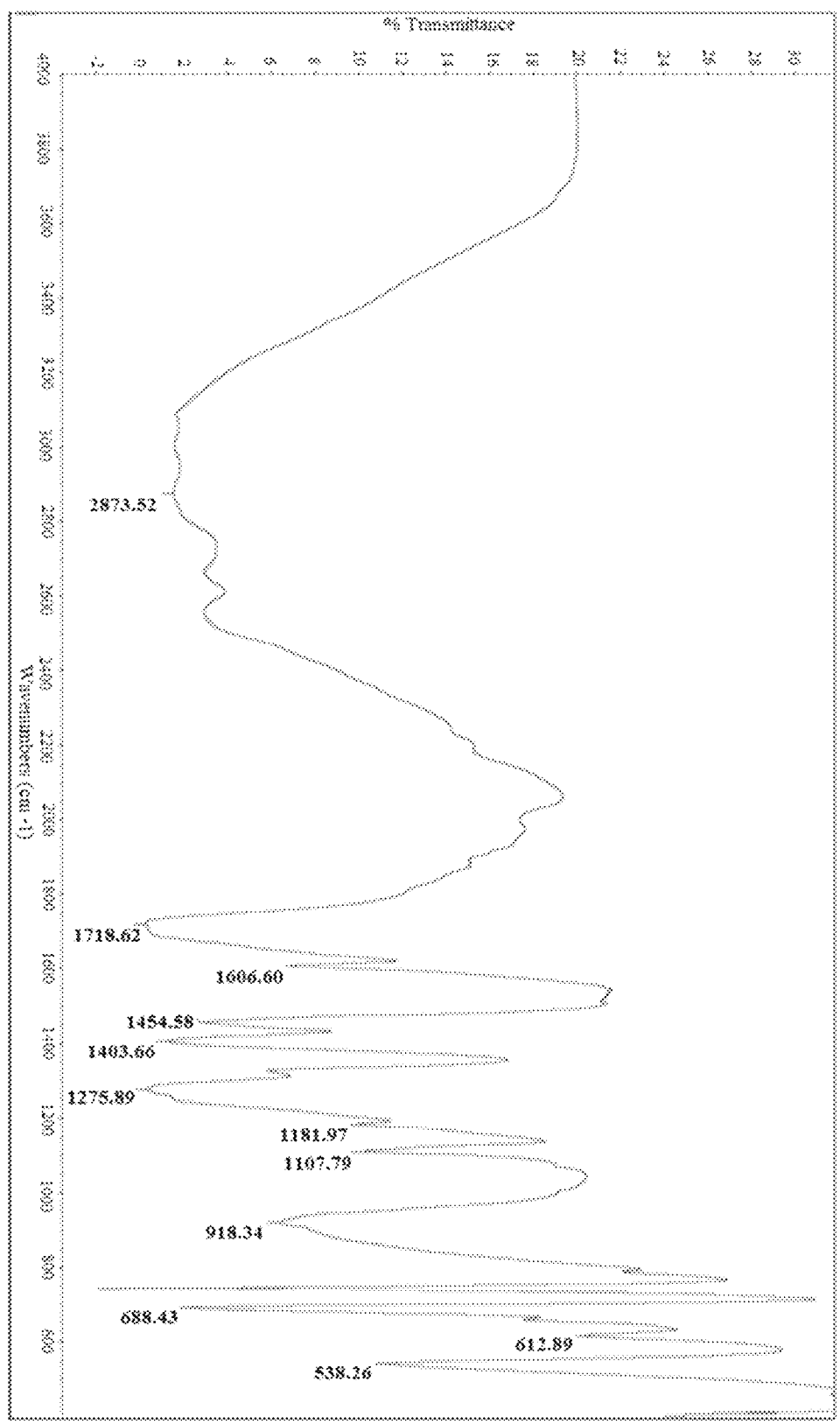
FIG. 13 is a Fourier transform infrared (FT-IR) spectrum of 1,3,5-benzenetricarboxylic acid (BTC).
Figure 14:
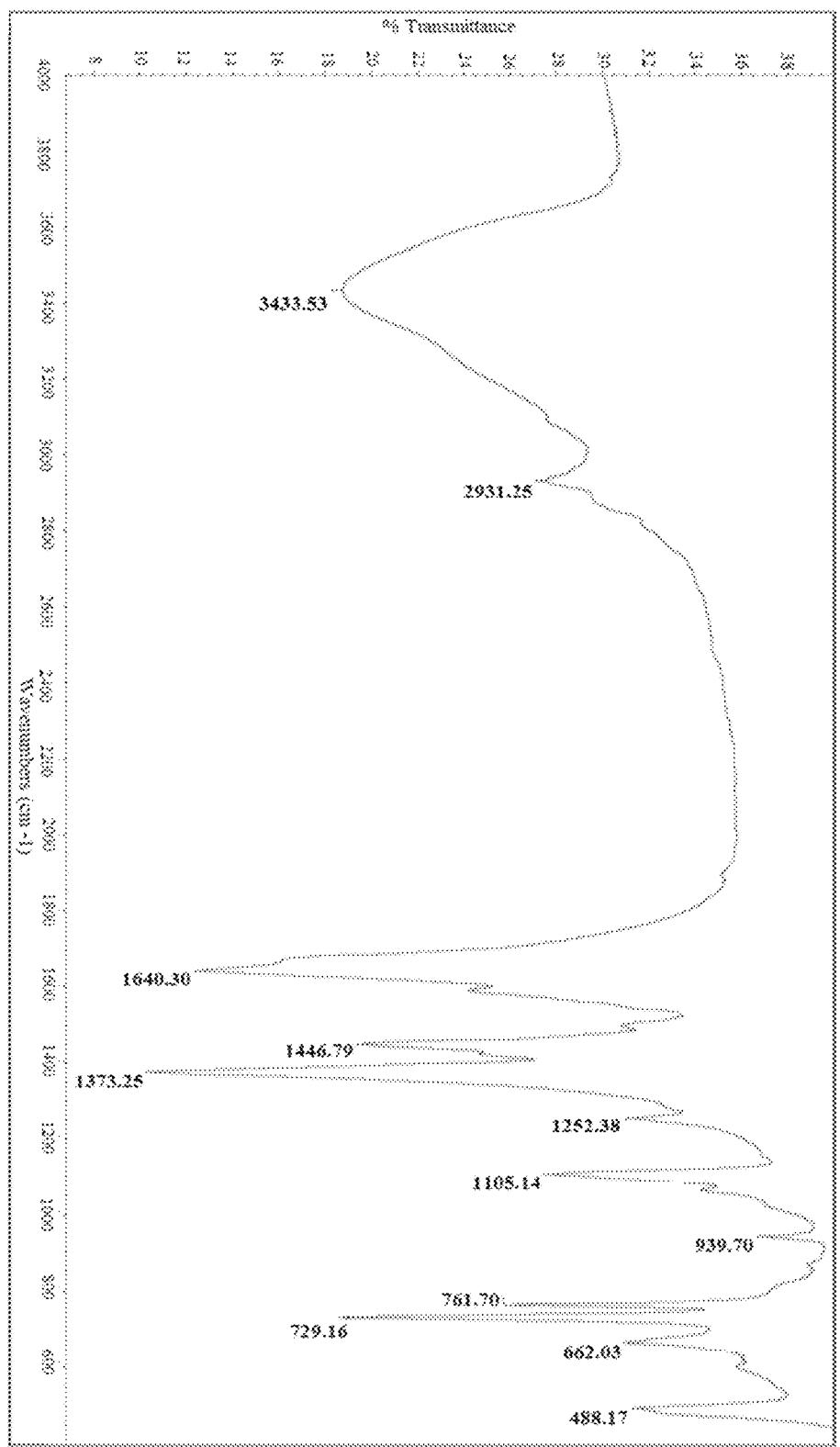
FIG. 14 is a FT-IR spectrum of the prepared HKUST-1 metal organic framework.
Figure 15:
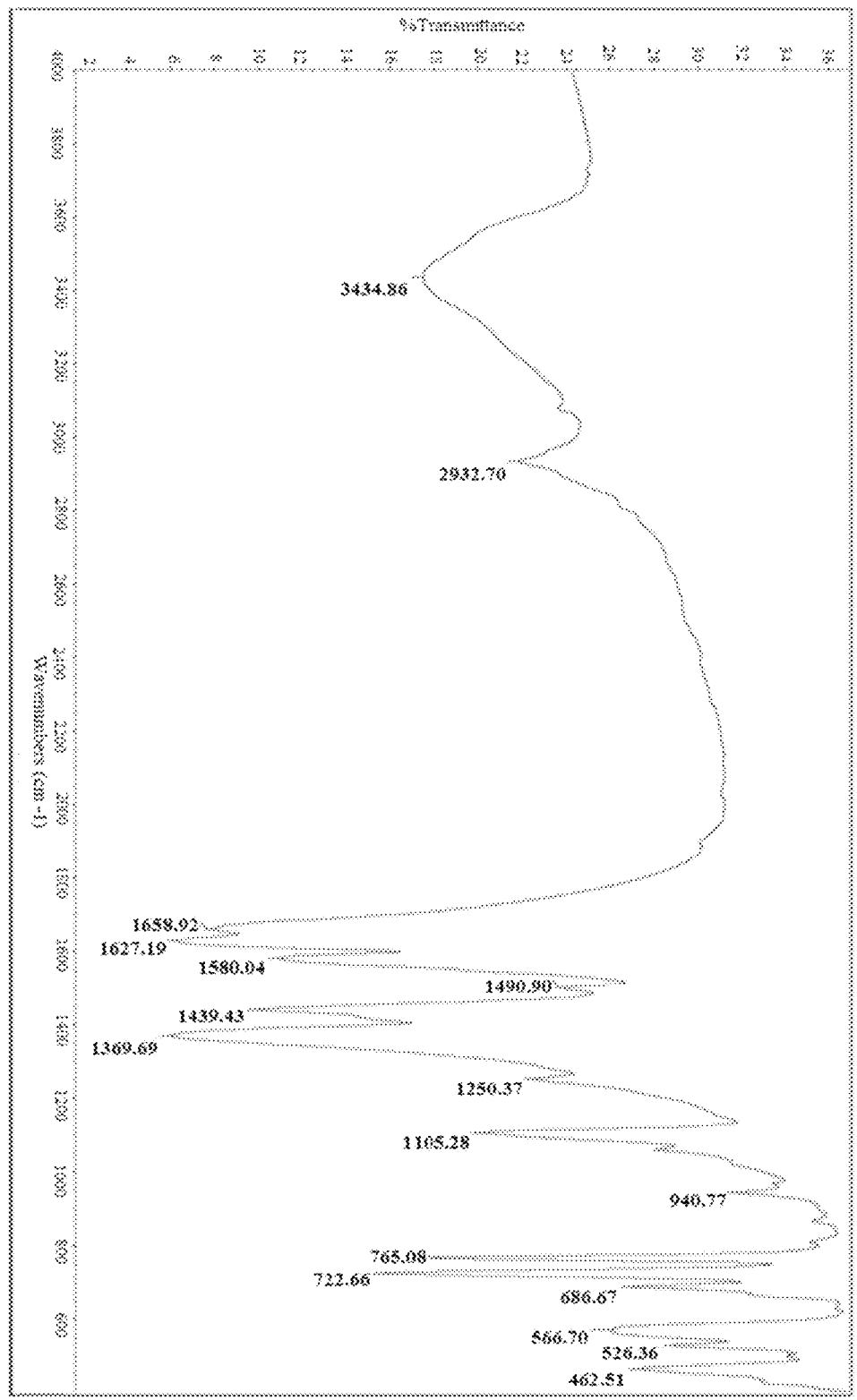
FIG. 15 is a FT-IR spectrum of the prepared Zn-HKUST-1 metal organic framework.
Figure 16:
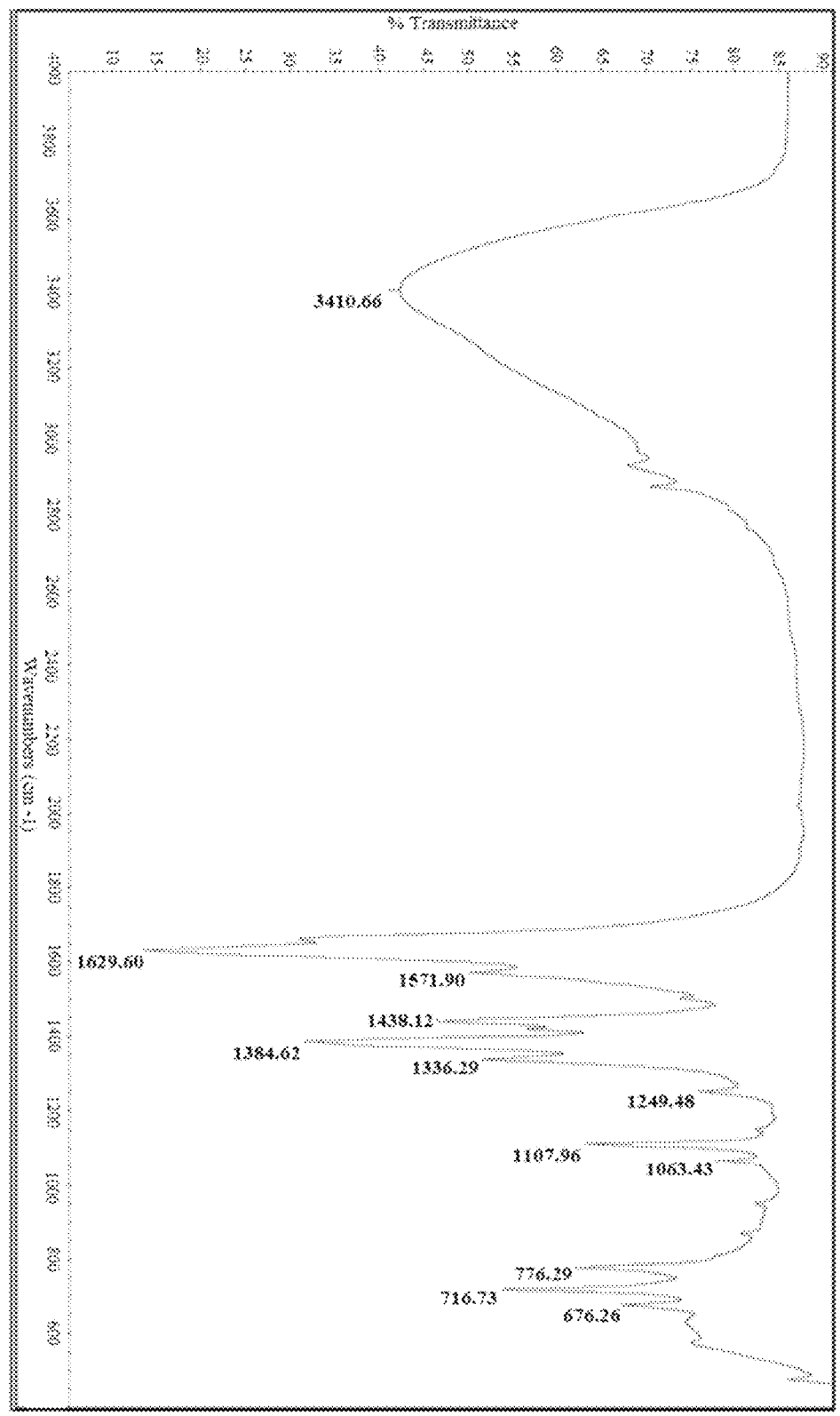
FIG. 16 is a FT-IR spectrum of the prepared Fe—Zn-HKUST-1 metal organic framework after transmetallation.
Figure 17:
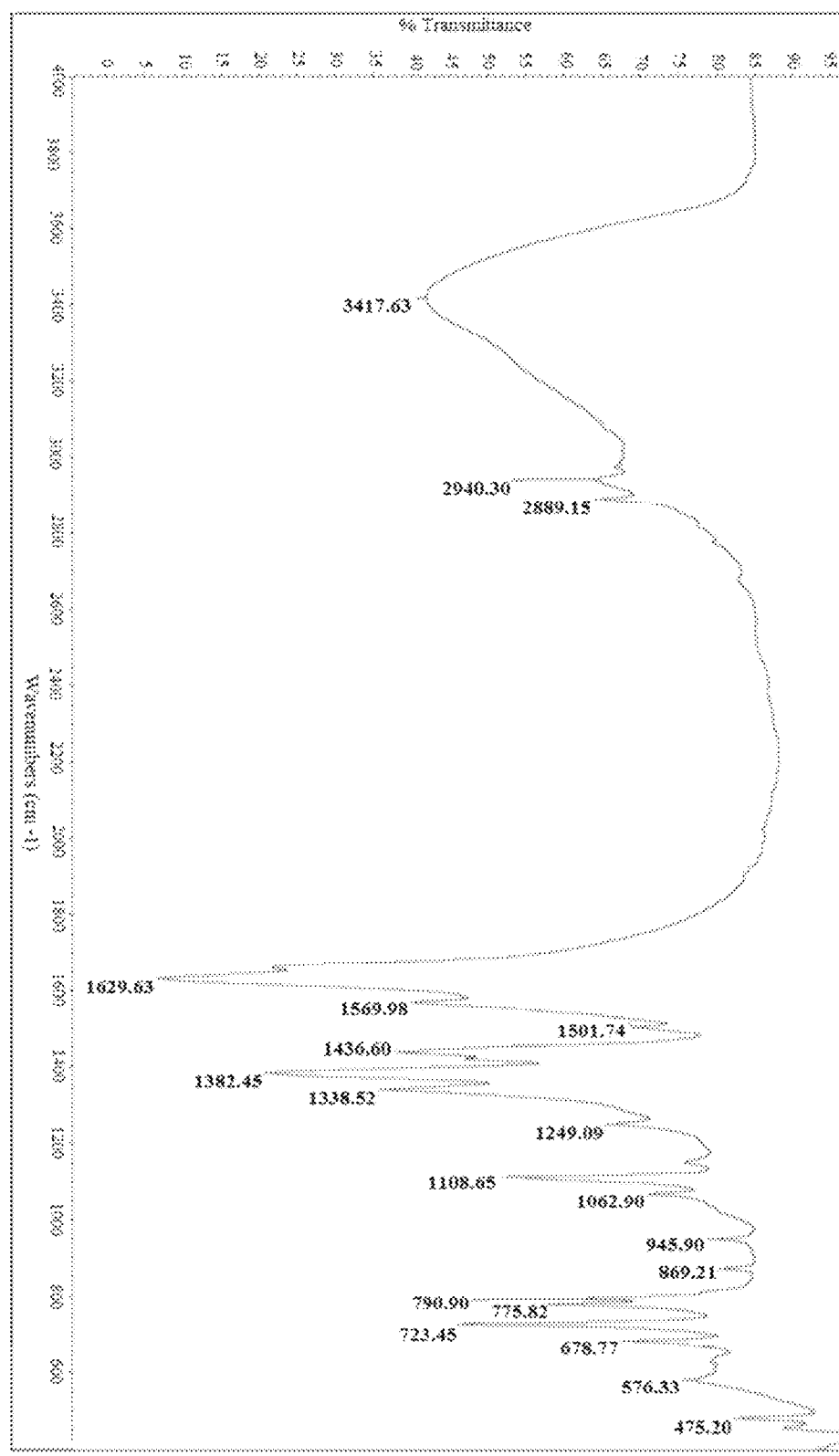
FIG. 17 is a FT-IR spectrum of the prepared Co—Zn-HKUST-1 metal organic framework after transmetallation.
Figure 18:
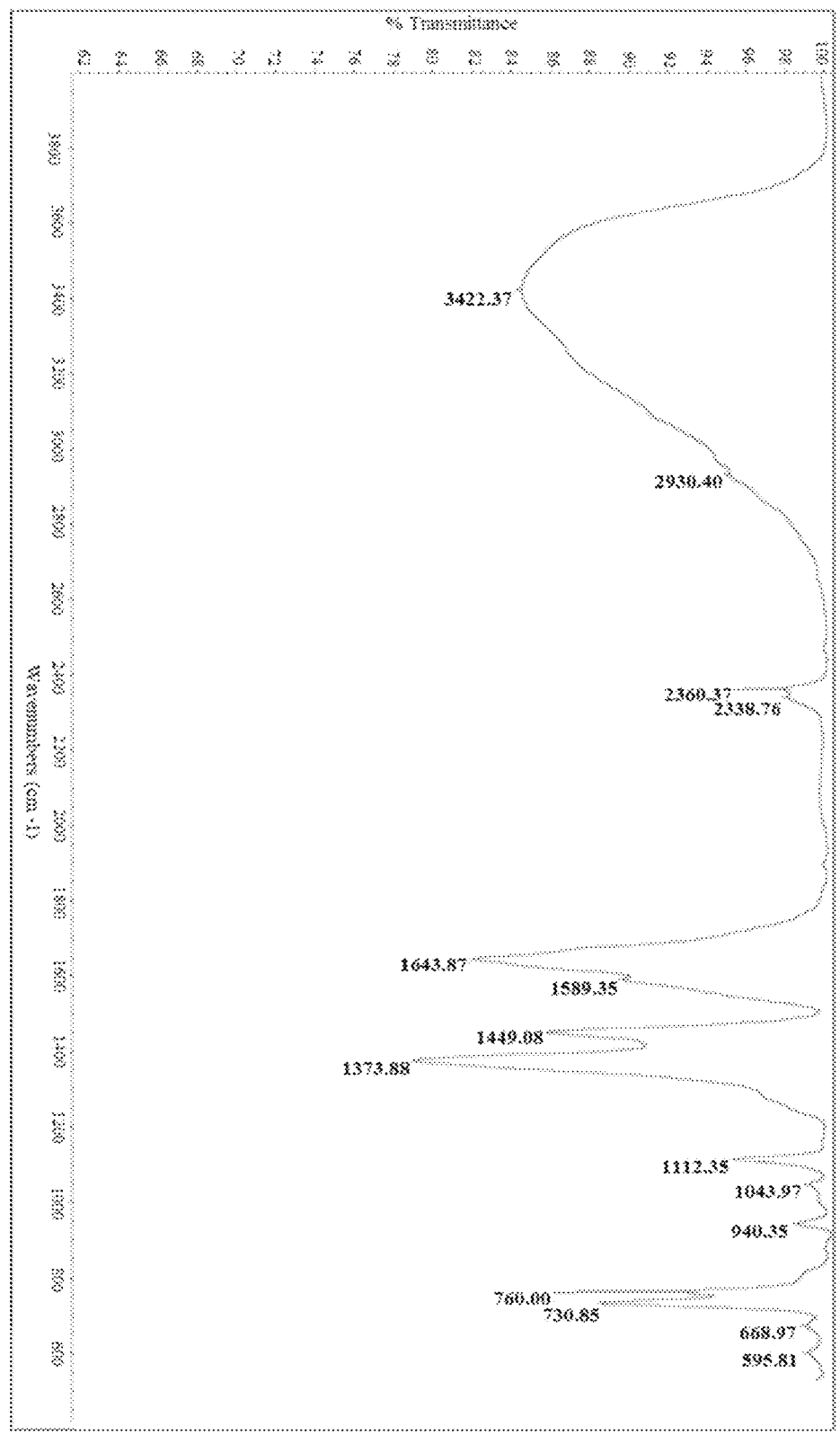
FIG. 18 is a FT-IR spectrum of the prepared Cu—Zn-HKUST-1 metal organic framework after transmetallation.

Fourier transform infrared (FT-IR) spectra were taken on a Nicolet spectrophotometer using KBr within the standard range of 400-4000 $cm^{-1}$. This method was used to confirm the formation of HKUST-1, Zn-HKUST-1, as well as the transmetallated Zn-HKUST-1 isostructural metal organic frameworks (MOFs). 1,3,5-benzenetricarboxylic acid (BTC) as a ligand shows the C=O stretching frequency of carboxylic acid around 1718 $cm^{-1}$ and also a broad O—H peak at about 2933 $cm^{-1}$ which corresponds to the hydrogen bonding. FIG. 13 is the FT-IR spectrum of 1,3,5-benzentricarboxylic acid (BTC). The FT-IR analysis of HKUST-1 (FIG. 14) and Zn-HKUST-1 (FIG. 15) indicates that there was a significant shift in the C=O stretching frequency of the BTC ligand. The disappearance of the broad acidic O—H peak of BTC at 2933 $cm^{-1}$ was the result of deprotonation that leads to coordination. The band for the O—C—O asymmetric stretching of HKUST-1 and Zn-HKUST-1 appeared at 1658 $cm^{-1}$ and 1640 $cm^{-1}$ respectively, due to the binding of the carbonyl oxygen with metal atoms. The sharp peaks at 3433 $cm^{-1}$ for HKUST-1 (FIGS. 14) and 3434 $cm^{-1}$ for Zn-HKUST-1 (FIG. 15) are due to the axial $H_2O$ ligands that are coordinated to the dimeric Cu atoms forming an octahedral unit. Similarly, FT-IR spectra of Fe—Zn-HKUST-1 (FIG. 16), Co—Zn-HKUST-1 (FIG. 17) and Cu—Zn-HKUST-1 (FIG. 18) show great similarity to that of Zn-HKUST-1 which indicates that there was substantial retention of the MOF framework after transmetallaion.

EXAMPLE 4

Field Emission Scanning Electron Microscopy (FESEM) Analysis of Prepared Metal Organic Frameworks (MOFs)

Figure 19:
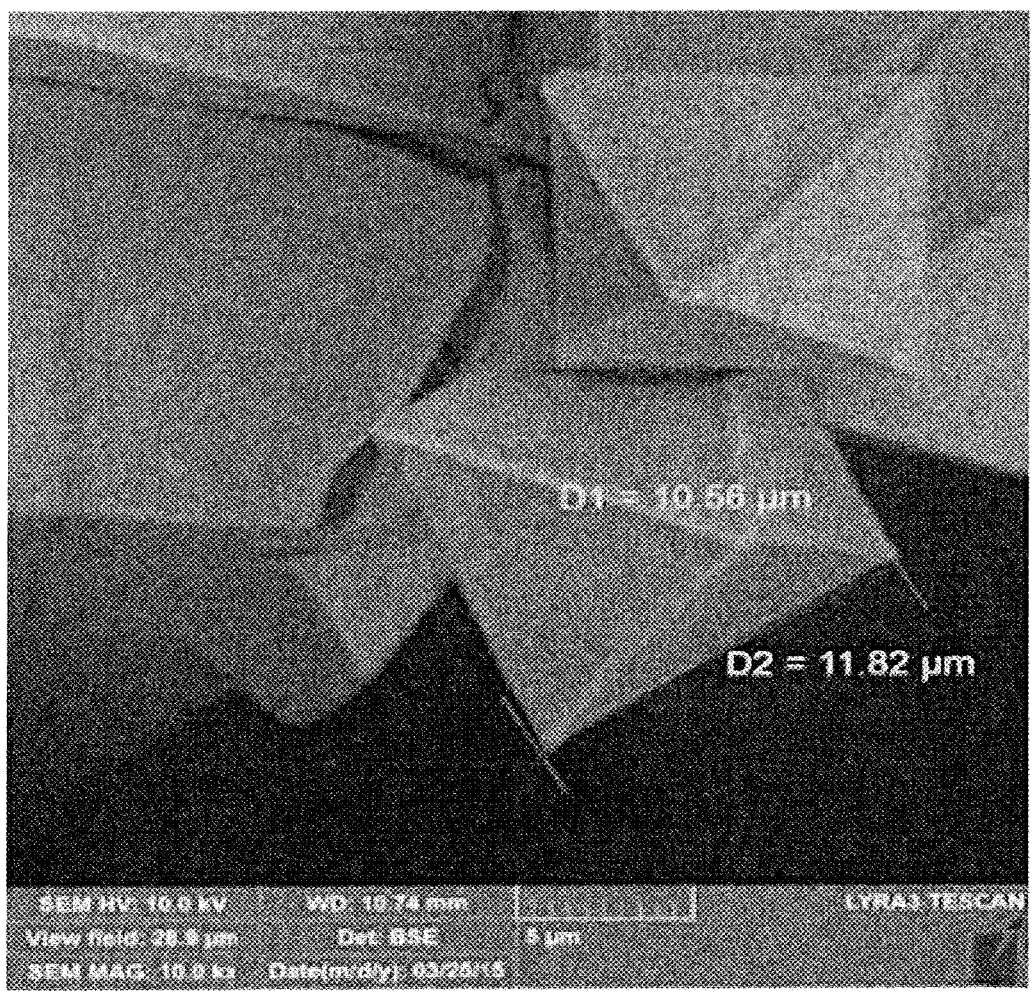
FIG. 19 is a scanning electron microscopy (SEM) image of the prepared HKUST-1 metal organic framework at a magnified view.
Figure 20:
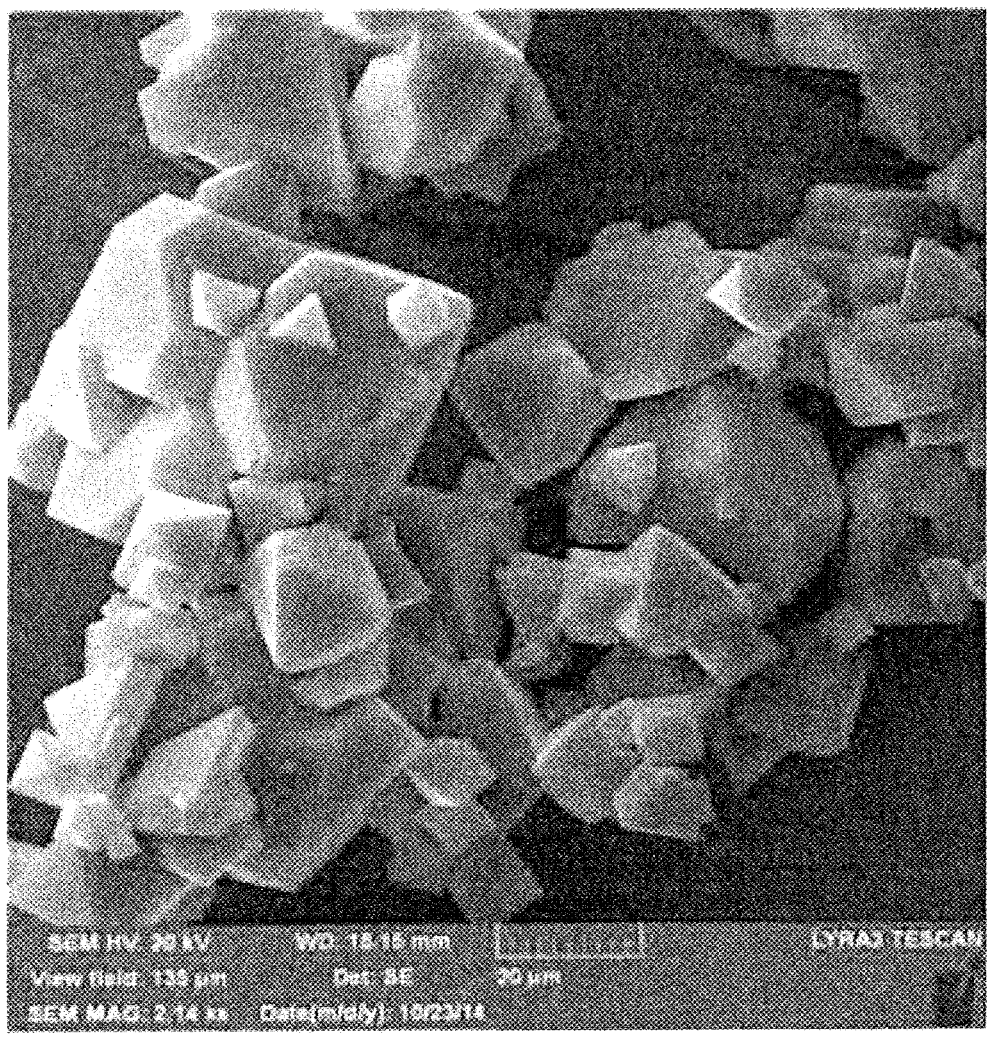
FIG. 20 is a SEM image of the prepared HKUST-1 metal organic framework.
Figure 21:
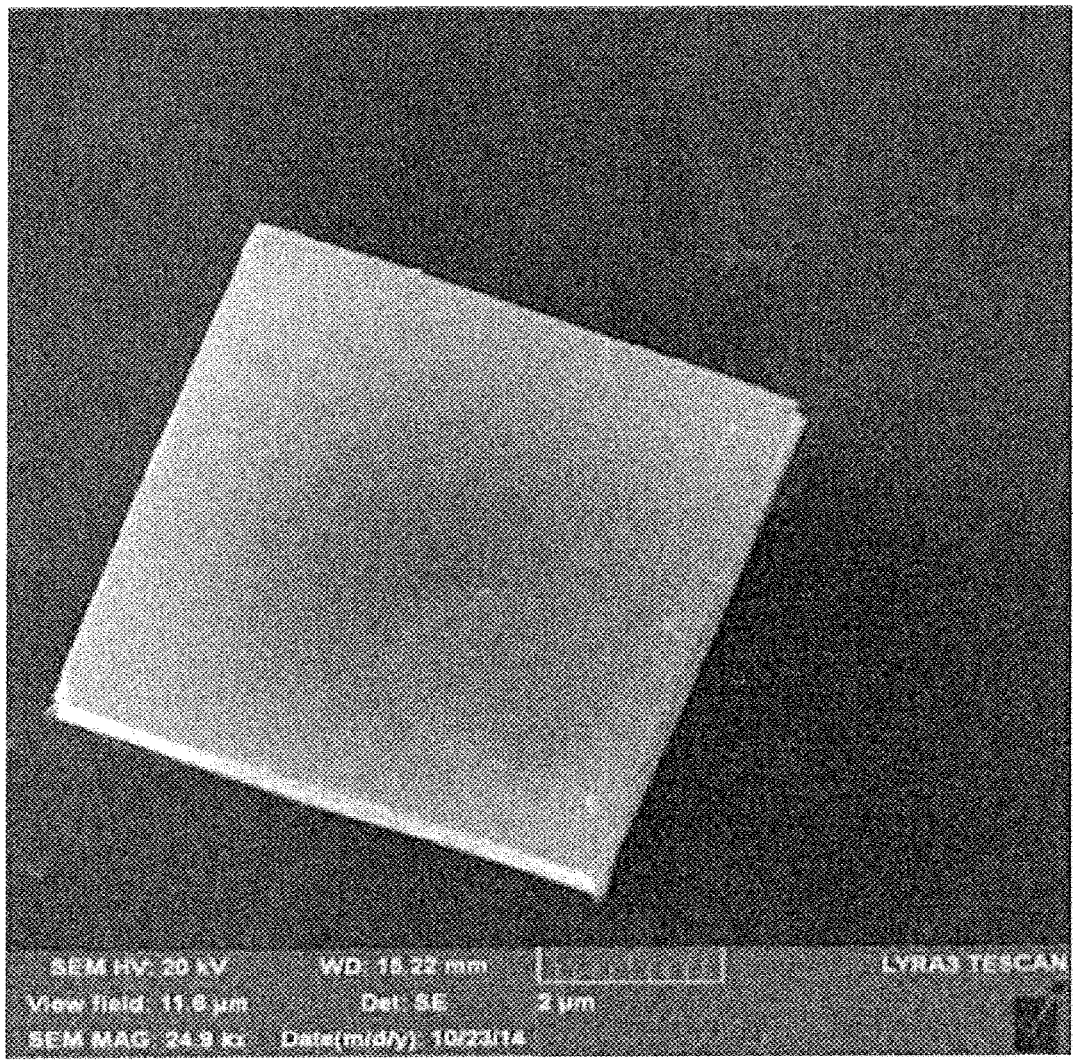
FIG. 21 is a SEM image of the prepared Zn-HKUST-1 metal organic framework at a magnified view.
Figure 22:
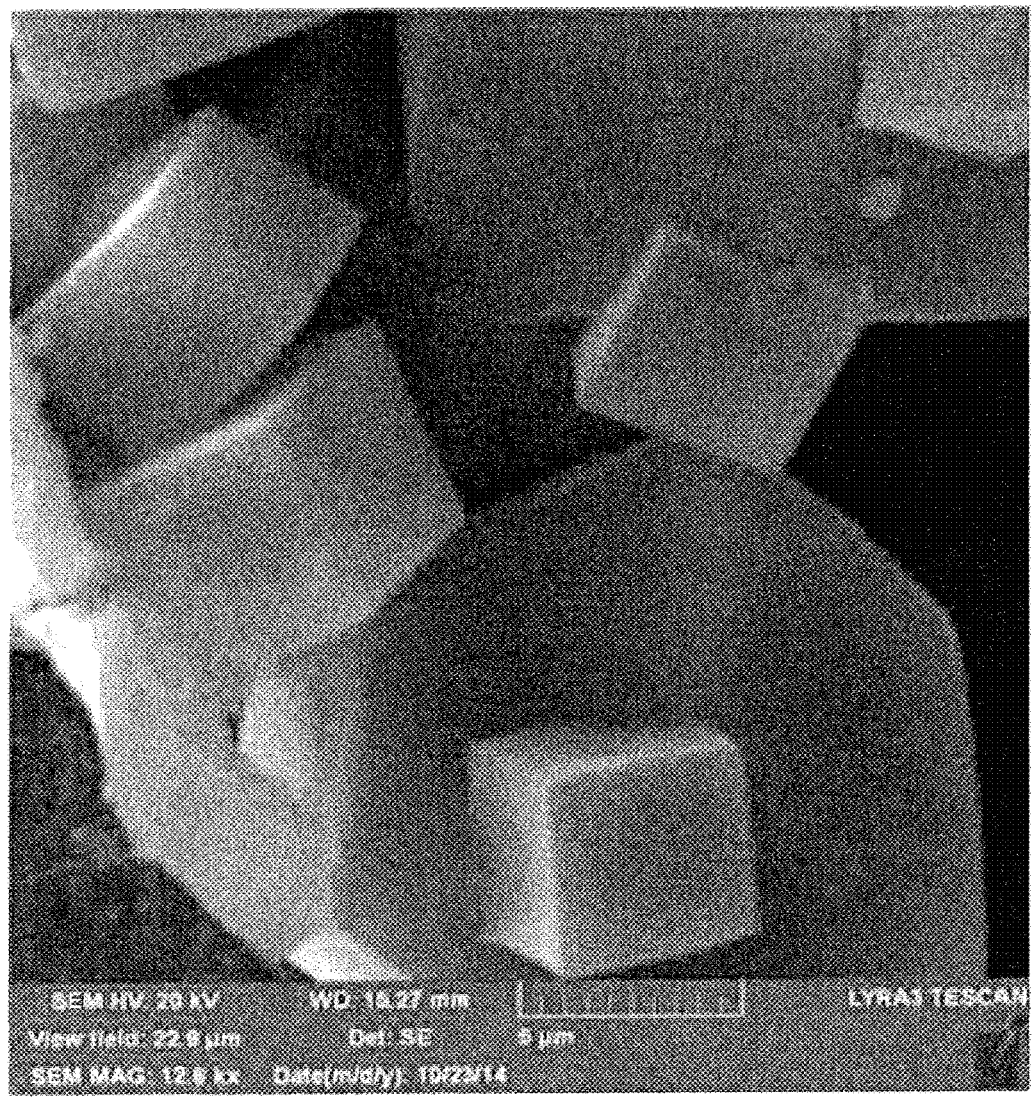
FIG. 22 is a SEM image of the prepared Zn-HKUST-1 metal organic framework.

Field emission scanning electron microscopy (FESEM, Tescan-Lyra-3) was used to provide images of the synthesized catalysts. Scanning electron microscopy (SEM) uses a focused beam of high energy electrons to generate a variety of signals at the surface of solid specimens. The signals that are derived from electron-sample interactions reveal information about the sample including external morphology (texture), chemical composition, and crystalline structure as well as the orientation of materials making up the sample. Accelerated electron in a SEM carry significant amounts of kinetic energy, and this energy is dissipated as a variety of signals produced by electron-sample interactions when the incident electrons are decelerated in the solid samples. These signals include secondary electrons (that produce SEM images), backscattered electrons (BSE), and diffracted backscattered electrons (DBSE) that are used to determine crystal structures and orientations. Secondary electrons are most valuable for showing morphology and topography of samples and backscattered electrons are most valuable for illustrating contrasts in the composition of a multiphase sample (i.e. for rapid phase discrimination). FIG. 19 and FIG. 20 show the SEM images of the synthesized HKUST-1 catalyst at different magnifications. FIG. 21 and FIG. 22 show the SEM images of the synthesize Zn-HKUST-1 catalyst at different magnifications. The SEM images of the synthesized catalysts are shown with the same magnification of 2-20 μm scale bar. The micrograph images show the formation of crystalline materials as expected. HKUST-1 was observed to occur in the form of a polyhedral (octahedral) crystal (FIG. 19 and FIG. 20) with sizes of a few microns. The micrograph images of Zn-HKUST-1 show the formation of polyhedral (cubic) crystals (FIG. 21 and FIG. 22) with sizes of a few microns.

EXAMPLE 5

Powder X-Ray Diffraction (P-XRD) Analysis of Prepared Metal Organic Frameworks (MOFs)

Figure 23:
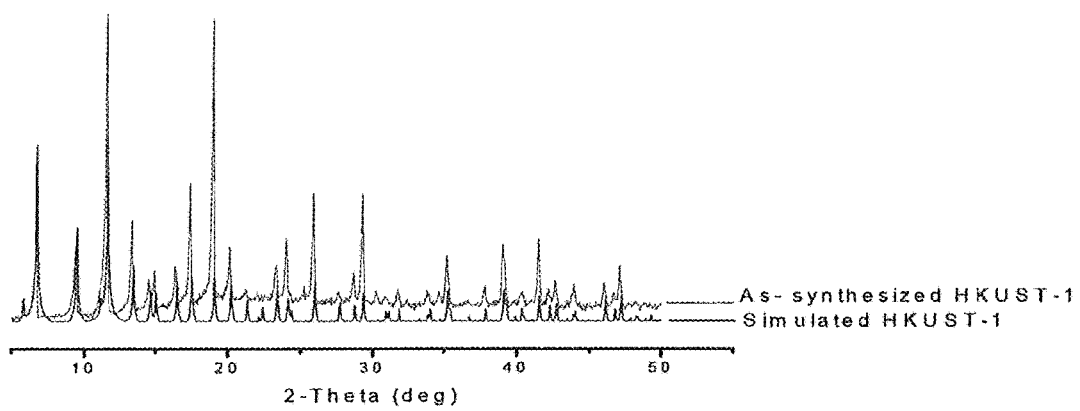
FIG. 23 is a powder X-ray diffraction (PXRD) pattern for the simulated HKUST-1 metal organic framework and the prepared experimental HKUST-1 metal organic framework.
Figure 24:
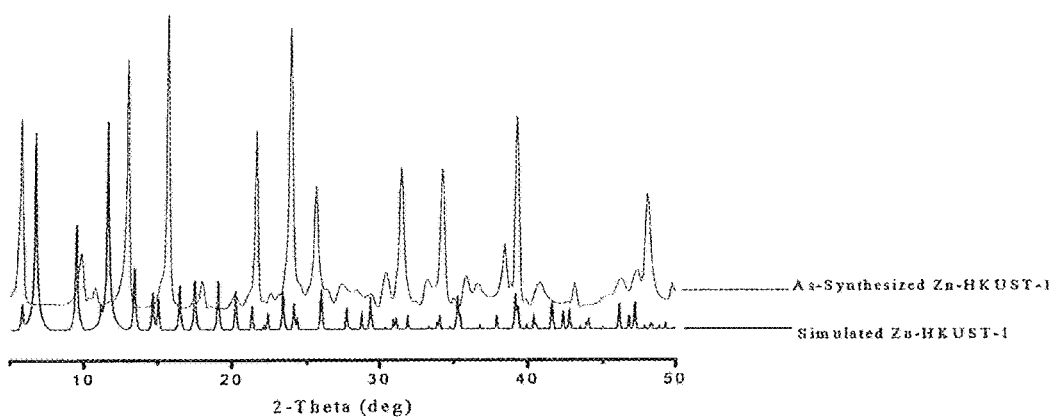
FIG. 24 is a PXRD pattern for the simulated Zn-HKUST-1 metal organic framework and the prepared experimental Zn-HKUST-1 metal organic framework.
Figure 25:
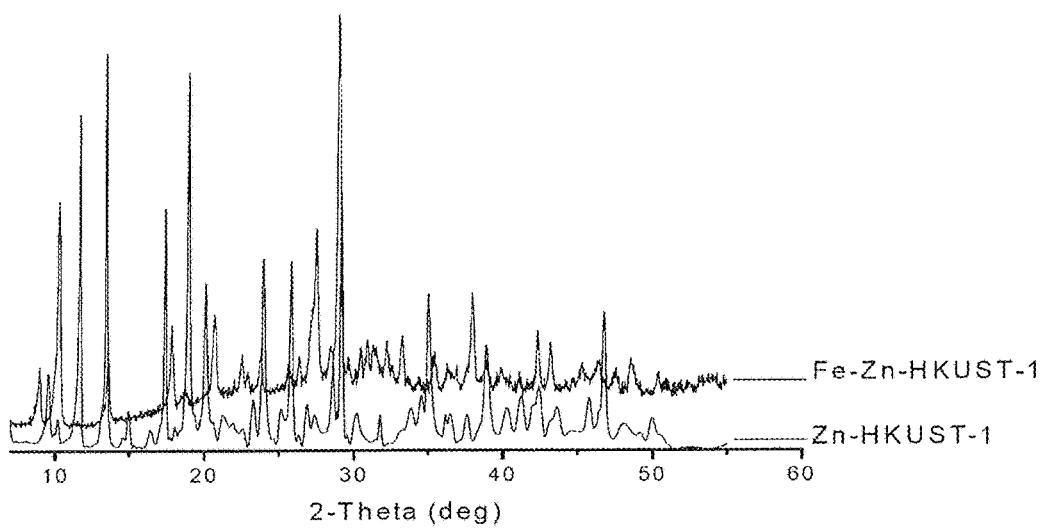
FIG. 25 is a comparative PXRD analysis showing PXRD patterns of the prepared Fe—Zn-HKUST-1 metal organic framework after transmetallation and the prepared Zn-HKUST-1 metal organic framework.
Figure 26:
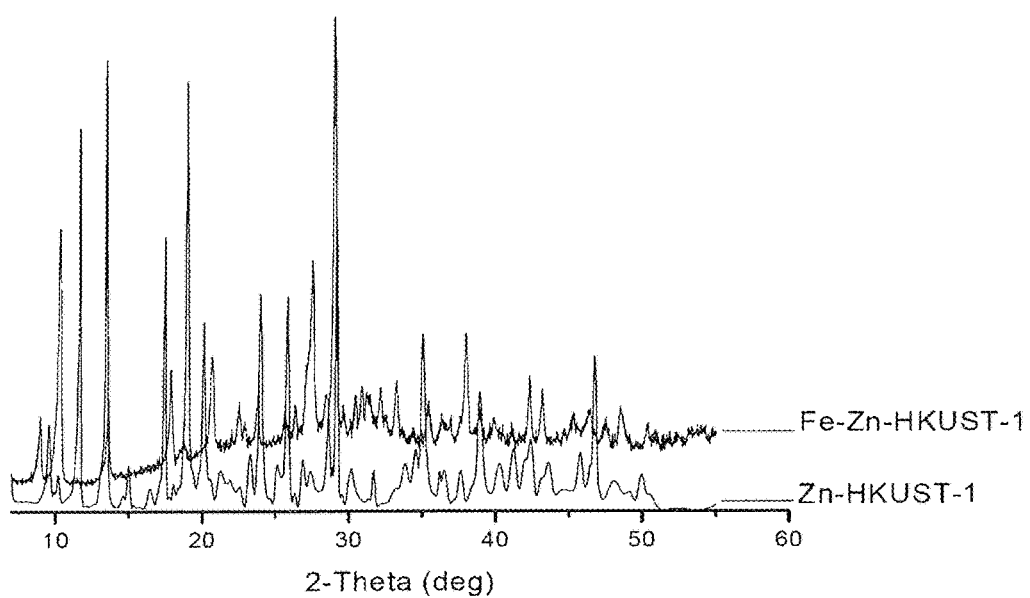
FIG. 26 is a comparative PXRD analysis showing PXRD patterns of the prepared Co—Zn-HKUST-1 metal organic framework after transmetallation and the prepared Zn-HKUST-1 metal organic framework.
Figure 27:
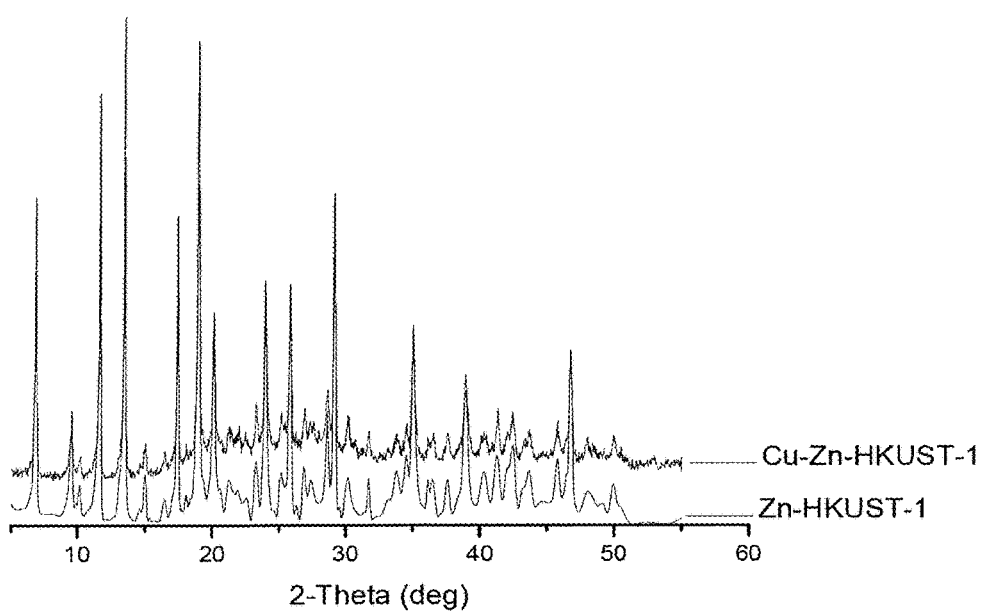
FIG. 27 is a comparative PXRD analysis showing PXRD patterns of the prepared Cu—Zn-HKUST-1 metal organic framework after transmetallation and the prepared Zn-HKUST-1 metal organic framework.

Powder X-ray diffraction (P-XRD) patterns were collected using a Rigaku Miniflex II instrument with a monochromator of CuKα1 (1.5406 Å) at 30 kV and 15 mA. The PXRD patterns were recorded in the static scanning mode from 5° to 60° (2θ) at a detector angular speed of 2° θ min-1 and step size of 0.02°. The wavelength of X-rays is approximately the same as the distance between the particles in the lattice. If the beam of X-rays strikes a crystal, the X-rays are deflected by the crystal and are detected by a photographic plate. This technique was used to examine the morphological structure of the synthesized catalyst. The crystallinity of HKUST-1 and Zn-HKUST-1 was probed by PXRD after solvent evacuation under reduced pressure at elevated temperatures. The diffraction patterns show that HKUST-1 (FIG. 23) appears isostructural to Zn-HKUST-1 (FIG. 24) with a slightly larger unit cell (HKUST-1, a=26.343 (0.005 Å) and Zn-HKUST-1, a=26.520 (0.001 Å)). The respective patterns were compared to those found in the Cambridge Structural Database (CSD). The CSD reference patterns were simulated using Mercury V. 3.3 and are shown in FIG. 23 and FIG. 24. Differences in peak intensities between simulated and experimental diffractograms can be attributed to pore occlusion by coordinated guest molecules. The powder patterns of Fe—Zn-HKUST-1 (FIG. 25), Co—Zn-HKUST-1 (FIG. 26) and Cu—Zn-HKUST-1 (FIG. 27) show that the modified MOFs are isostructural to Zn-HKUST-1. This can be confirmed as the XRD pattern of each of the modified MOF catalysts shows a reasonable level of similarity to the confirmed Zn-HKUST-1 pattern as overlaid in FIG. 25, FIG. 26, and FIG. 27.

EXAMPLE 6

Inductively Coupled Plasma Mass Spectrometry (ICP-MS) Analysis of Prepared Metal Organic Frameworks (MOFs)

Inductively coupled plasma mass spectrometry (ICP-MS) is an analytical technique which is capable of detecting metals and several non-metals at concentrations as low as one part in $10^{15}$ (part per quadrillion, ppq). The working principle is based on the ionization of the sample with an inductively coupled plasma followed by the accurate separation and quantification of those ions with a mass spectrometer. Compared to atomic absorption spectroscopy, ICP-MS has better sensitivity, precision and speed. Prior to ICP-MS analysis, the Fe—Zn-HKUST-1, Co—Zn-HKUST-1, and Cu—Zn-HKUST-1 metal organic frameworks were digested using a 30% HNO3 solution and the samples were further diluted to 10 ppm. The ICP-MS analysis of Fe—Zn-HKUST-1 revealed that 34% of the $Zn^{2+}$ in Zn-HKUST-1 was replaced by $Fe^{2+}$ indicating that the transmetallation was incomplete. Similarly, 34% of the $Zn^{2+}$ in Zn-HKUST-1 was replaced by $Co^{2+}$ ions in the Co—Zn-HKUST-1 catalyst. On the other hand, the analysis of metal ions in Cu—Zn-HKUST-1 showed that 90% of the $Zn^{2+}$ ions were replaced by $Cu^{2+}$.

EXAMPLE 7

Catalytic Toluene Oxidation Reactions and Analysis

Figure 28:
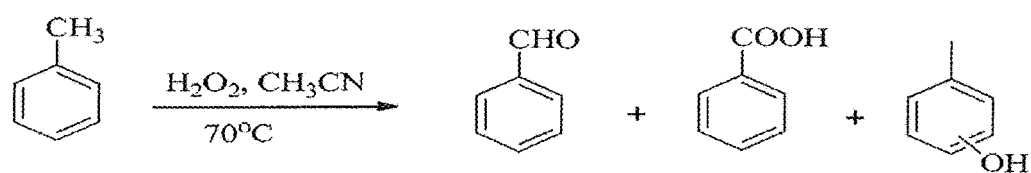
FIG. 28 is the chemical equation and general scheme for the oxidation of toluene.

The catalytic oxidation of toluene in the presence of hydrogen peroxide as an oxidizing agent was performed at 70° C. using a 10-point electrothermal reactor. 2 mL of toluene and 0.03 g of an activated HKUST type MOF catalyst was added into the reaction tube followed by the addition of 4 mL of acetonitrile and 2 mL of $H_2O_2$. FIG. 28 shows the chemical equation and scheme for the oxidation of toluene. The reaction mixture was stirred and an aliquot of the samples was collected after 6, 12, 18, and 24 hours for gas chromatography mass spectrometer (GC-MS) and gas chromatography-flame ionization detector (GC-FID) analysis.

The oxidation of toluene proceeded in the presence of $H_2O_2$ as an oxidizing agent using acetonitrile as solvent to give a mixture of oxygenated products as expected. The formation of a mixture of products was the first test of the catalytic activity of the metal organic frameworks (MOFs). The blank experiment, in the absence of an MOF did not lead to any significant toluene conversion even after 24 hours. The outcome of the blank experiment was similar to what had already been previously reported in the literature [Bin Du, Song-Il Kim, Lan-Lan, Lou Aizhong, Jia, Gaixia Liu, Ben Qi, Shuangxi Liu *Applied Catalysis A: General*, 2012 425, 191-198.—incorporated herein by reference in its entirety]. HKUST-1 showed a good activity for title oxidation of toluene reaction affording a conversion of 51% after 6 hours. Table 1 summarizes the results of toluene oxidation with HKUST-1.

TABLE 1

Results of toluene oxidation with HKUST-1

| Time (hr) | % Converision | Benzaldehyde (%) | Benzoic Acid (%) | Beznyl Alcohol (%) | O, M, P-Cresols (%) |
|---|---|---|---|---|---|
| 6 | 51 | 18 | 17 | trace | 65 |
| 12 | 60 | 19 | 20 | trace | 61 |
| 18 | 77 | 17 | 25 | trace | 58 |
| 24 | 80 | 16 | 26 | trace | 58 |

Cresols were the major products and their amounts in the product mixture decreased from 65% after 6 hours to 58% after 24 hours due to the formation of benzoic acids as by-product. The formation of cresols in this reaction is not surprising as this could be as a result of the hydroxylation of the aromatic ring in the presence of peroxide. The selectivity in benzaldehyde was also significantly decreasing from 18% in 6 hours to 16% after 24 hours as the selectivity of benzoic acid has increased with time. This suggests that the rate of benzoic acid formation from benzaldehyde is faster than the rate of toluene oxidation. Despite the fact that Zn is not a good oxidation metal, Zn-HKUST-1 pushed the oxidation of toluene to 22% after 24 hours with 22% selectivity. Table 2 summarizes the results of toluene oxidation with Zn-HKUST-1. This could be attributed to the electronic structure of the metal organic framework (MOF) resulting from the coordination of the BTC ligand. The effect of time can also be easily observed by considering the significant differences in conversion and benzaldehyde selectivity with the progress of the reaction. It should be noted that the Zn-HKUST-1 catalyst did not favor further oxidation of benzaldehyde to benzoic acid.

TABLE 2

Results of toluene oxidation with Zn-HKUST-1

| Time (hr) | % Converision | Benzaldehyde (%) | Benzoic Acid (%) | O, M, P-Cresols (%) |
|---|---|---|---|---|
| 6 | 1.7 | 0 | 0 | 100 |
| 12 | 10 | 8 | 0 | 92 |
| 18 | 19 | 18 | 0 | 82 |
| 24 | 22 | 22 | 0 | 78 |

The incorporation of Fe into the Zn-HKUST-1 framework gave a significant improvement to the catalytic activity. Table 3 summarizes the results of toluene oxidation with Fe—Zn-HKUST-1. Apart from the gradual initial increase in the conversion that can be attributed to the presence of Fe, Fe—Zn-HKUST-1, clearly exemplified the unique performance of Fe in oxidation reactions, especially in terms of selectivity with the catalyst giving the highest benzaldehyde selectivity of 61% at 6 hours. Unlike Fe—Zn-HKUST-1, Co—Zn-HKUST-1 gave similar performance to Zn-HKUST-1. Table 4 summarizes the results of toluene oxidation with Co—Zn-HKUST-1. Table 5 summarizes the results of toluene oxidation with Cu—Zn-HKUST-1. The catalytic activity of Cu modified Zn-HKUST-1 (Cu—Zn-HKUST-1) for toluene oxidation demonstrated that Cu greatly improves the conversion of toluene relative to Zn-HKUST-1. After 6 hours Cu—Zn-HKUST-1 gave a conversion of 34% with 16% benzaldehyde selectivity, while Zn-HKUST on the other hand gave very low conversion without benzaldehyde over the same time period.

TABLE 3

Results of toluene oxidation with Fe—Zn-HKUST-1

| Time (hr) | % Converision | Benzaldehyde (%) | Benzoic Acid (%) | O, M, P-Cresols (%) |
|---|---|---|---|---|
| 6 | 17 | 61 | 6 | 33 |
| 12 | 20 | 60 | 6 | 34 |
| 18 | 28 | 60 | 7 | 33 |
| 24 | 30 | 57 | 8 | 35 |

TABLE 4

Results of toluene oxidation with Co—Zn-HKUST-1

| Time (hr) | % Converision | Benzaldehyde (%) | Benzoic Acid (%) | O, M, P-Cresols (%) |
|---|---|---|---|---|
| 6 | 1 | 6 | 0 | 84 |
| 12 | 16 | 25 | 0 | 75 |
| 18 | 20 | 28 | 0 | 72 |
| 24 | 38 | 32 | 0 | 68 |

TABLE 5

Results of toluene oxidation with Cu—Zn-HKUST-1

| Time (hr) | % Converision | Benzaldehyde (%) | Benzoic Acid (%) | O, M, P-Cresols (%) |
|---|---|---|---|---|
| 6 | 34 | 16 | 13 | 71 |
| 12 | 56 | 14 | 14 | 72 |
| 18 | 65 | 17 | 17 | 66 |
| 24 | 70 | 18 | 15 | 67 |

EXAMPLE 8

Catalytic Cycloalkane Oxidation Reactions and Analysis

Figure 29:
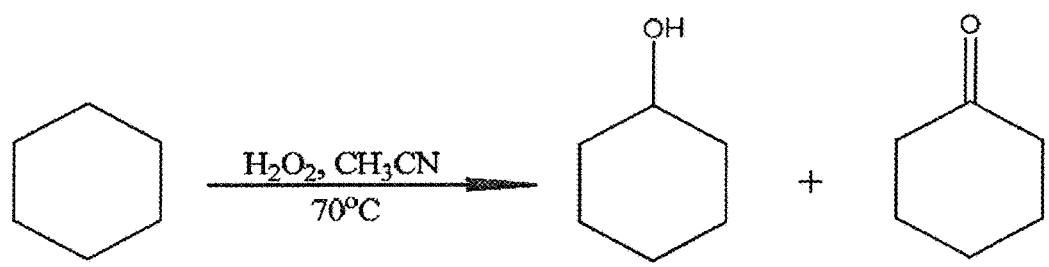
FIG. 29 is the chemical equation and general scheme for the oxidation of cyclohexane.
Figure 30:
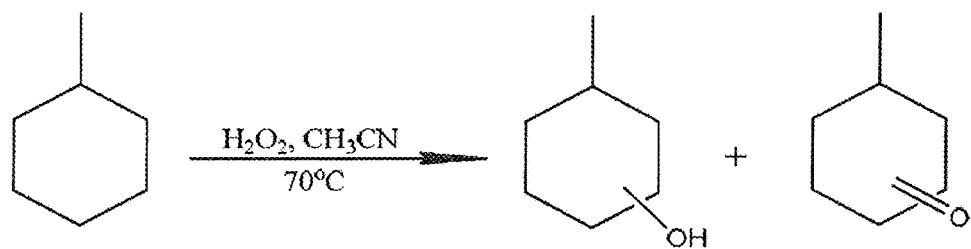
FIG. 30 is the chemical equation and general scheme for the oxidation of methylcyclohexane.

For the oxidation of cycloalkanes, the 10-point electrothermal reactor and stirrer was charged with a mixture containing the activated HKUST type MOF catalyst (0.03 g), acetonitrile (4 mL), cyclohexane or methylcyclohexane (0.5 mL), and 2 mL of 30% $H_2O_2$. The mixture was vigorously stirred and heated at 70° c. Aliquots of the reaction mixtures were taken after 6, 12, 18, and 24 hours for GC-MS and GC-FID analysis. FIG. 29 shows the chemical equation and scheme for the oxidation of cyclohexane. FIG. 30 shows the chemical equation and scheme for the oxidation of methylcyclohexane.

The isostructural HKUST-1 metal organic frameworks (MOFs) acted as catalysts for the oxidation of cyclohexane with $H_2O_2$ at 70° C. forming cyclohexanol and cyclohexanone as major products. Table 6 summarizes the results of cyclohexane oxidation with HKUST-1. HKUST-1 was observed to be the most active catalyst, achieving the highest conversion of 52% which is better than those of well-known catalytic materials previously reported in the literature and comparable to that of modified zeolite [Gobema-Ferrón S., Lillo V., and Galán-Mascarós, R. *Catal. Comm.* 2012, 23, 30-33.; and Bagherzadeh, M, Amini, F., Ellern, A., Woo, L. *Inorg. Chem. Comm.* 2012, 15, 52-55.; and Alavi, S, Hosseini-Monfared, H., Siczek, M. *Journal of Molecular Catalysis A*, 2013, 377, 16-28.—each incorporated herein by reference in its entirety]. The catalyst gave an initial low conversion of 9% but this value increased steadily as the reaction progresses to 24 hours. The great activity of HKUST-1 could be largely attributed to the heavy presence of vacant Cu sites in the framework. In contrast, Zn-HKUST-1 did not show any significant activity for this reaction even after 24 hours. This inactivity of Zn-HKUST-1 could be due to the $d^{10}$ electronic configuration of the Zn metal which is unfavorable for alkane oxidation.

TABLE 6

Results of cyclohexane oxidation with HKUST-1

| Time (hr) | % Converision | Cyclohexanone (%) | Cyclohexanol (%) |
|---|---|---|---|
| 6 | 9 | 100 | — |
| 12 | 29 | 77 | 23 |

TABLE 6-continued

Results of cyclohexane oxidation with HKUST-1

| Time (hr) | % Converision | Cyclohexanone (%) | Cyclohexanol (%) |
|---|---|---|---|
| 18 | 39 | 60 | 40 |
| 24 | 52 | 60 | 40 |

Drastic improvement in activity was observed when Fe was incorporated into the framework of Zn-HKUST-1. Table 7 summarizes the results of cyclohexane oxidation with Fe—Zn-HKUST-1. Fe—Zn-HKUST-1 gave the high conversion of 20% after 24 hours. Similarly, Co—Zn-HKUST-1 gave high conversion of 27% with reasonable selectivity in cyclohexanol and cyclohexanone. Table 8 summarizes the results of cyclohexane oxidation with Co—Zn-HKUST-1. Table 9 summarizes the results of cyclohexane oxidation with Cu—Zn-HKUST-1. Cu—Zn-HKUST-1 gave a conversion of 40% after 24 hours with an equal ratio of cyclohexanol and cyclohexanone. The activity of Cu—Zn-HKUST-1 is similar to what was observed for HKUST-1 in terms of the conversion and this could be attributed to the Cu atoms which are probably responsible for the relatively high conversion.

TABLE 7

Results of cyclohexane oxidation with Fe—Zn-HKUST-1

| Time (hr) | % Converision | Cyclohexanone (%) | Cyclohexanol (%) | 4-hydroxy cyclohexanone (%) | 1,4-cyclohexadione (%) |
|---|---|---|---|---|---|
| 6 | 5 | 45 | 28 | 25 | 2 |
| 12 | 7 | 59 | 26 | 12 | 3 |
| 18 | 13 | 56 | 21 | 18 | 5 |
| 24 | 20 | 55 | 20 | 21 | 4 |

TABLE 8

Results of cyclohexane oxidation with Co—Zn-HKUST-1

| Time (hr) | % Converision | Cyclohexanone (%) | Cyclohexanol (%) |
|---|---|---|---|
| 6 | 2 | 55 | 25 |
| 12 | 9 | 60 | 40 |
| 18 | 15 | 65 | 35 |
| 24 | 27 | 65 | 35 |

TABLE 9

Results of cyclohexane oxidation with Cu—Zn-HKUST-1

| Time (hr) | % Converision | Cyclohexanone (%) | Cyclohexanol (%) |
|---|---|---|---|
| 6 | 7 | 69 | 31 |
| 12 | 15 | 56 | 44 |
| 18 | 33 | 55 | 45 |
| 24 | 40 | 51 | 49 |

Methylcyclohexane was oxidized using the isostructural metal organic frameworks (MOFs) at 70° C. in the presence of $H_2O_2$ to afford reasonable yields of oxygenated products. GC-MS analysis revealed the formation of 5 different oxygenated products with methylcyclohexanol and methylcyclohexanone being the major products. HKUST-1 gave the highest conversion of 48% for this reaction after 24 hours with methylcyclohexanol as the major product while it afforded only 18% conversion after 6 hours. Table 10 summarizes the results of methylcyclohexane oxidation with HKUST-1. The difference in reaction time largely affects the conversion but has little effect on the methylcyclohexanol selectivity.

TABLE 10

Results of methylcyclohexane oxidation with HKUST-1

| Time (hr) | % Converision | Methyl-cyclohexanol (%) | Methyl-cyclohexanone (%) | Cyclohexane methanol (%) | Cyclohexanal (%) |
|---|---|---|---|---|---|
| 6 | 18 | 56 | 27 | 17 | trace |
| 12 | 31 | 64 | 11 | 25 | trace |
| 18 | 35 | 59 | 16 | 20 | 05 |
| 24 | 48 | 58 | 19 | 18 | 05 |

The modification of Zn-HKUST-1 however generally improved its activity for methylcyclohexane oxidation. Table 11 summarizes the results of methylcyclohexane oxidation in the presence of Fe—Zn-HKUST-1. With Fe—Zn-HKUST-1 35 conversion of the substrate was observed in 6 hours with approximately equal amounts of methylcyclohexanol and methylcyclohexanone produced. There was a gradual increase in the percent conversion to 15% after 24 hours. The effect of Fe incorporation into the Zn-HKUST-1 framework is noteworthy since only Zn-HKUST-1 was not active at up to 24 hours under the same reaction conditions. Similarly, Co—Zn-HKUST showed appreciable activity over Zn-HKUST-1 due to the presence of Co atoms in the metal organic framework (MOF). Table 12 summarizes the results of methylcyclohexane oxidation with Co—Zn-HKUST-1. Table 13 summarizes the results of methylcyclohexane oxidation with Cu—Zn-HKUST-1. Table 13 shows the results obtained for the liquid phase oxidation of methylcyclohexane where the highest conversion of 45% was observed after 24 hours forming a higher amount of methylcyclohexanol.

Figure 32:
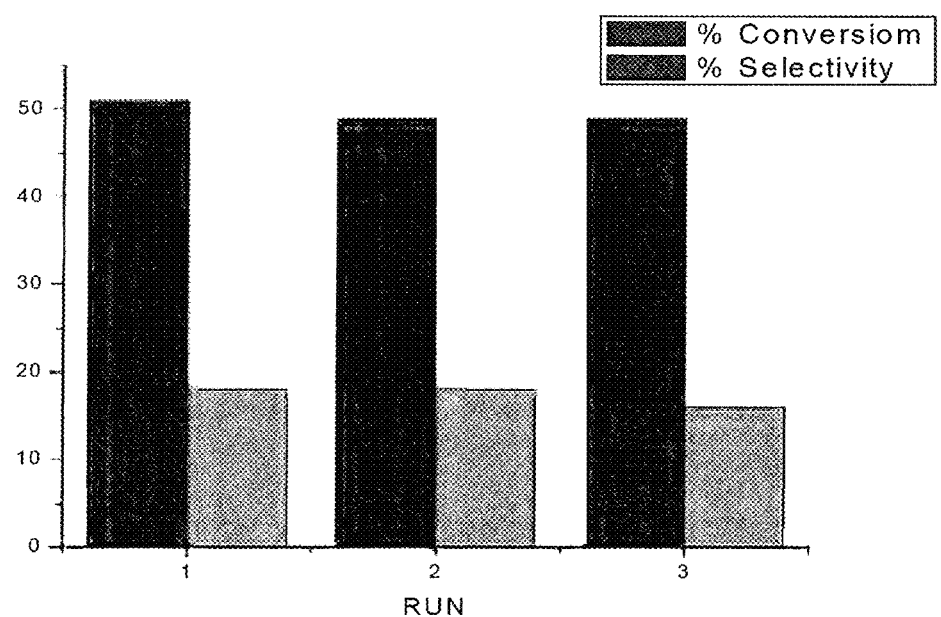
FIG. 32 is a graph showing the percent conversion and the percent benzaldehyde selectivity of the prepared HKUST-1 metal organic framework after a single and multiple runs as a catalyst in the oxidation of toluene.

HKUST-1 catalysts. Since the catalyst was found to be structurally intact, the catalytic activity was tested for toluene oxidation in two repeated runs. There was significant retention of activity in terms of conversion of toluene and selectivity for benzaldehyde. FIG. 32 is a graphical illustration of the maintained conversion and selectivity of the catalyst over three runs.

In conclusion, pure single crystals of HKUST-1 and Zn-HKUST-1 were successfully synthesized using solvothermal methods and the synthesized Zn-HKUST-1 was subjected to modification via transmetallation affording reasonable amounts of transmetallated products. Both the synthesized and modified metal organic frameworks (MOFs) were characterized using FTIR, FESEM, PXRD, and ICP-MS. Furthermore, the catalytic activity of the MOFs was tested in the oxidation of toluene, cyclohexane and methylcyclohexane. Fe—Zn-HKUST-1 gave the best activity in terms of benzaldehyde selectivity for the oxidation of toluene.

TABLE 11

Results of methylcyclohexane oxidation with Fe—Zn-HKUST-1

| Time (hr) | % Conversion | Methyl-cyclohexanol (%) | Methyl-cyclohexanone (%) | Cyclohexane methanol (%) | Cyclohexanal (%) |
|---|---|---|---|---|---|
| 6 | 3 | 42 | 51 | trace | 7 |
| 12 | 10 | 53 | 39 | trace | 8 |
| 18 | 12 | 49 | 35 | 3 | 13 |
| 24 | 15 | 45 | 37 | 8 | 10 |

TABLE 12

Results of methylcyclohexane oxidation with Co—Zn-HKUST-1

| Time (hr) | % Conversion | Methyl-cyclohexanol (%) | Methyl-cyclohexanone (%) | Cyclohexane methanol (%) | Cyclohexanal (%) |
|---|---|---|---|---|---|
| 6 | 6 | 43 | 57 | — | trace |
| 12 | 7 | 61 | 33 | — | 6 |
| 18 | 10 | 45 | 51 | — | 4 |
| 24 | 14 | 44 | 39 | 4 | 13 |

TABLE 13

Results of methylcyclohexane oxidation with Cu—Zn-HKUST-1

| Time (hr) | % Conversion | Methyl-cyclohexanol (%) | Methyl-cyclohexanone (%) | Cyclohexane methanol (%) | Cyclohexanal (%) |
|---|---|---|---|---|---|
| 6 | 18 | 55 | 27 | 18 | — |
| 12 | 29 | 65 | 15 | 20 | — |
| 18 | 40 | 60 | 16 | 20 | 4 |
| 24 | 45 | 66 | 14 | 17 | 3 |

Figure 31:
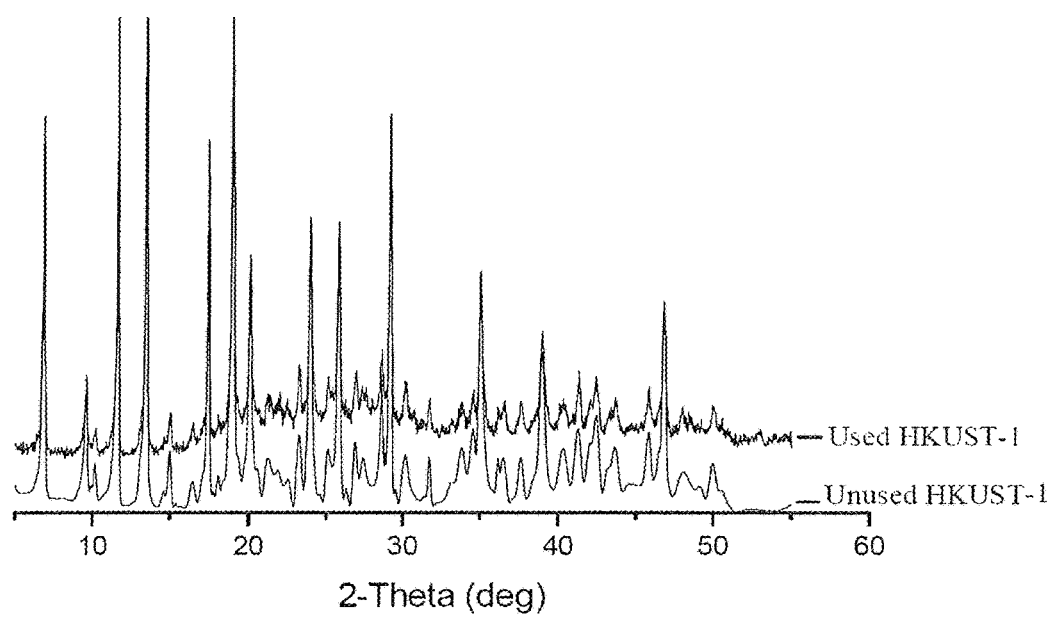
FIG. 31 is a comparative PXRD analysis showing PXRD patterns of the unused prepared HKUST-1 metal organic framework and the used prepared HKUST-1 metal organic framework after use as a catalyst in the oxidation of a cyclic hydrocarbon.

The reusability of the catalysts was also examined. The HKUST-1 metal organic framework was recovered, washed, and reactivated for two more runs after 6 hours. The dried HKUST-1 was subjected to powder X-ray diffraction (PXRD) to ascertain if the metal organic framework (MOF) was able to withstand the reaction conditions. The PXRD analysis revealed that there was no collapse in the metal organic framework (MOF) after 6 hours. FIG. 31 shows the great match between the patterns for the unused and used Thus, the foregoing discussion discloses and describes merely exemplary embodiments of the present invention. As will be understood by those skilled in the art, the present invention may be embodied in other specific forms without departing from the spirit or essential characteristics thereof. Accordingly, the disclosure of the present invention is intended to be illustrative, but not limiting of the scope of the invention, as well as other claims. The disclosure, including any readily discernible variants of the teachings herein, defines, in part, the scope of the foregoing claim terminology such that no inventive subject matter is dedicated to the public.

The invention claimed is:

1. A transmetallated metal organic framework catalyst, comprising:
   zinc (II) ions;
   second metal ions selected from the group consisting of cobalt (II) ions, iron (II) ions, copper (II) ions and mixtures thereof; and
   benzene-1,3,5-tricarboxylic acid ligands;
   wherein the benzene-1,3,5-tricarboxylic acid ligands comprise carboxylate groups, each carboxylate group forming a coordinative bond to the zinc (II) ions or the second metal ions to form a coordination network in the form of porous polyhedral crystals that are isostructural to an HKUST-1 metal organic framework,
   wherein the metal organic framework catalyst does not comprise a coordinated solvent and a ratio of the Zn (II) ions to the second metal ions is in the range of 1.0 to 3.0.

2. The transmetallated metal organic framework catalyst of claim 1, wherein the porous polyhedral crystals have pores with an average diameter of 0.2-2.0 nm and a BET surface area in a range of 500-3000 $m^2/g$.

3. The transmetallated metal organic framework catalyst of claim 1, wherein the porous polyhedral crystals are octahedral or cubic with an average longest linear dimension in a range of 2-20 μm.

4. The transmetallated metal organic framework catalyst of claim 1, which has a larger unit cell dimension a than the HKUST-1 metal organic framework.

5. The transmetallated metal organic framework catalyst of claim 1, wherein the second metal ions are copper (II) ions and the ratio of zinc (II) ions to copper (II) ions is in a range of 0.01 to 1.0.

6. The transmetallated metal organic framework catalyst of claim 1, wherein the ratio of zinc (II) ions to the second metal ions is in a range of 0.5 to 5.0.

* * * * *